(12) United States Patent
Tobia et al.

(10) Patent No.: US 9,604,020 B2
(45) Date of Patent: Mar. 28, 2017

(54) INTEGRATED, EXTENDABLE ANESTHESIA SYSTEM

(71) Applicant: Spacelabs Healthcare LLC, Issaquah, WA (US)

(72) Inventors: Ronald Tobia, Sun Prairie, WI (US); Andrew Levi, Madison, WI (US); Gary Choncholas, Madison, WI (US); Bruce Dammann, Middleton, WI (US); Erik J. Bluemner, Verona, WI (US); Ben Schoepke, Madison, WI (US); Patrick Flanagan, Colgate, WI (US); Lee Dalgety, Middleton, WI (US); Cory Boudreau, Madison, WI (US); Sheldon Roberts, Sun Prairie, WI (US); Dorian Lust, McFarland, WI (US)

(73) Assignee: Spacelabs Healthcare LLC, Snoqualmie, WA (US)

(*) Notice: Subject to any disclaimer, the term of this patent is extended or adjusted under 35 U.S.C. 154(b) by 673 days.

(21) Appl. No.: 13/651,337

(22) Filed: Oct. 12, 2012

(65) Prior Publication Data
US 2013/0276780 A1 Oct. 24, 2013

Related U.S. Application Data

(63) Continuation-in-part of application No. 13/329,186, filed on Dec. 16, 2011, which is a
(Continued)

(51) Int. Cl.
*A61M 15/00* (2006.01)
*A61M 16/10* (2006.01)
(Continued)

(52) U.S. Cl.
CPC ........ *A61M 16/0051* (2013.01); *A61M 16/01* (2013.01); *A61M 16/104* (2013.01);
(Continued)

(58) Field of Classification Search
None
See application file for complete search history.

(56) References Cited

U.S. PATENT DOCUMENTS

| 2,820,651 A | 1/1958 | Phillips |
| 2,912,858 A | 11/1959 | Fuller |

(Continued)

FOREIGN PATENT DOCUMENTS

| CN | 1688256 | 10/2005 |
| CN | 1943505 A | 4/2007 |

(Continued)

OTHER PUBLICATIONS

First Office Action, Chinese Patent Application No. 2012800351488, Jun. 13, 2015.
(Continued)

*Primary Examiner* — Bradley Philips
*Assistant Examiner* — Eric Bryant
(74) *Attorney, Agent, or Firm* — Novel IP

(57) ABSTRACT

The anesthesia systems have an integrated, extendable clinical center and clinician/anesthesia office that accommodates for a physical separation of clinical and clerical functions. The anesthesia system includes an alarm reversion system which enables a predefined alarm limit to be set and then to be automatically reverted back to an alarm limit existing just before the predefined alarm limit was set.

6 Claims, 44 Drawing Sheets

Related U.S. Application Data continuation-in-part of application No. 13/329,219, filed on Dec. 17, 2011, now abandoned, application No. 13/651,337, which is a continuation-in-part of application No. 13/329,259, filed on Dec. 17, 2011, now Pat. No. 9,022,492, application No. 13/651,337, which is a continuation-in-part of application No. 12/906,081, filed on Oct. 16, 2010, now Pat. No. 9,086,313.

(60) Provisional application No. 61/546,930, filed on Oct. 13, 2011, provisional application No. 61/559,433, filed on Nov. 14, 2011, provisional application No. 61/424,312, filed on Dec. 17, 2010, provisional application No. 61/424,306, filed on Dec. 17, 2010, provisional application No. 61/424,298, filed on Dec. 17, 2010, provisional application No. 61/252,269, filed on Oct. 16, 2009.

(51) Int. Cl.
*F16K 31/00* (2006.01)
*A61M 16/00* (2006.01)
*A61M 16/01* (2006.01)
*A61M 16/20* (2006.01)
A61M 16/08 (2006.01)
A61M 16/22 (2006.01)

(52) U.S. Cl.
CPC ........ *A61M 16/1015* (2014.02); *A61M 16/20* (2013.01); *A61M 16/009* (2013.01); *A61M 16/0816* (2013.01); *A61M 16/208* (2013.01); *A61M 16/22* (2013.01); *A61M 2016/0027* (2013.01); *A61M 2016/0039* (2013.01); *A61M 2016/0042* (2013.01); *A61M 2016/1035* (2013.01); *A61M 2202/0208* (2013.01); *A61M 2202/0283* (2013.01); *A61M 2205/3375* (2013.01); *A61M 2205/3569* (2013.01); *A61M 2205/3592* (2013.01); *A61M 2205/3606* (2013.01); *A61M 2205/502* (2013.01); *A61M 2205/8206* (2013.01); *A61M 2205/8212* (2013.01); *A61M 2205/8237* (2013.01); *A61M 2209/082* (2013.01); *A61M 2209/084* (2013.01)

(56) References Cited

U.S. PATENT DOCUMENTS

| | | |
|---|---|---|
| 2,944,547 A | 7/1960 | Ziherl |
| 3,517,639 A | 6/1970 | Whitsel |
| 3,608,545 A | 9/1971 | Novack |
| 3,618,592 A | 11/1971 | Stewart |
| 3,673,863 A | 7/1972 | Spacek |
| 3,897,606 A | 8/1975 | Schleining |
| 3,938,551 A | 2/1976 | Henkin |
| 3,981,329 A | 9/1976 | Wohlwend |
| 4,064,826 A | 12/1977 | Pauli |
| 4,148,312 A | 4/1979 | Bird |
| 4,167,115 A | 9/1979 | Stoever |
| 4,513,294 A | 4/1985 | Anderson |
| 4,557,216 A | 12/1985 | Demyon |
| 4,625,731 A | 12/1986 | Quedens |
| 4,630,486 A | 12/1986 | Miles |
| 4,697,450 A | 10/1987 | Bachman |
| 4,869,253 A | 9/1989 | Craig |
| 4,879,997 A * | 11/1989 | Bickford ............... 128/200.21 |
| 4,903,222 A | 2/1990 | Carter |
| 4,944,305 A | 7/1990 | Takatsu |
| 4,989,791 A * | 2/1991 | Ridenour ............. B05B 1/3026 239/579 |
| 4,991,576 A * | 2/1991 | Henkin et al. .......... 128/203.28 |
| 5,087,906 A | 2/1992 | Eaton |
| 5,101,851 A | 4/1992 | Abadi |
| 5,144,898 A | 9/1992 | Posly |
| 5,174,163 A * | 12/1992 | Gussman ................. G01N 1/22 251/352 |
| 5,197,480 A | 3/1993 | Gebhardt |
| 5,213,108 A | 5/1993 | Bredesen |
| 5,222,486 A | 6/1993 | Vaughn |
| 5,231,981 A | 8/1993 | Schreiber |
| 5,233,975 A | 8/1993 | Choate |
| 5,262,944 A | 11/1993 | Weisner |
| 5,291,182 A | 3/1994 | Wiseman |
| 5,311,908 A | 5/1994 | Barone |
| 5,319,363 A | 6/1994 | Welch |
| 5,322,069 A | 6/1994 | Gallant |
| 5,331,549 A | 7/1994 | Crawford, Jr. |
| 5,333,106 A | 7/1994 | Lanpher |
| 5,339,826 A | 8/1994 | Schmidt |
| 5,348,008 A | 9/1994 | Bornn |
| 5,372,389 A | 12/1994 | Tam |
| 5,373,746 A | 12/1994 | Bloss |
| 5,419,332 A | 5/1995 | Sabbah |
| 5,438,983 A | 8/1995 | Falcone |
| 5,467,954 A | 11/1995 | Wekell |
| 5,473,536 A | 12/1995 | Wimmer |
| 5,482,050 A | 1/1996 | Smokoff |
| 5,497,766 A | 3/1996 | Foster |
| 5,502,853 A | 4/1996 | Singleton |
| 5,515,083 A | 5/1996 | Casebolt |
| 5,553,296 A | 9/1996 | Forrest |
| 5,558,418 A | 9/1996 | Lambright |
| 5,563,495 A | 10/1996 | Tomiyori |
| 5,584,291 A | 12/1996 | Vapola |
| 5,586,909 A | 12/1996 | Saba |
| 5,633,457 A | 5/1997 | Kilar |
| 5,682,526 A | 10/1997 | Smokoff |
| 5,684,504 A * | 11/1997 | Verhulst et al. ................. 345/97 |
| 5,687,717 A | 11/1997 | Halpern |
| 5,692,494 A * | 12/1997 | Pernetti et al. .......... 128/200.24 |
| 5,715,813 A * | 2/1998 | Guevrekian ............ 128/205.12 |
| 5,718,235 A | 2/1998 | Golosarsky |
| 5,724,025 A | 3/1998 | Tavori |
| 5,724,985 A | 3/1998 | Snell |
| 5,749,367 A | 5/1998 | Gamlyn |
| 5,765,842 A | 6/1998 | Phaneuf |
| 5,779,305 A | 7/1998 | Hocking |
| 5,787,298 A | 7/1998 | Broedner |
| 5,800,360 A | 9/1998 | Kisner |
| 5,819,741 A | 10/1998 | Karlsson |
| 5,855,550 A | 1/1999 | Lai |
| 5,868,133 A * | 2/1999 | DeVries et al. ......... 128/204.21 |
| 5,904,328 A | 5/1999 | Leveridge |
| 5,956,013 A | 9/1999 | Raj |
| 5,975,081 A | 11/1999 | Hood |
| 6,005,767 A | 12/1999 | Ku |
| 6,024,089 A | 2/2000 | Wallace |
| 6,042,548 A | 3/2000 | Giuffre |
| 6,048,044 A | 4/2000 | Biggel |
| 6,050,940 A | 4/2000 | Braun |
| 6,063,028 A | 5/2000 | Luciano |
| 6,096,025 A | 8/2000 | Borders |
| 6,099,093 A | 8/2000 | Spence |
| 6,131,571 A | 10/2000 | Lampotang |
| 6,134,537 A | 10/2000 | Pao |
| 6,146,523 A | 11/2000 | Kenley |
| 6,155,255 A | 12/2000 | Lambert |
| 6,269,813 B1 * | 8/2001 | Fitzgerald et al. ...... 128/207.16 |
| 6,322,502 B1 | 11/2001 | Schoenberg |
| 6,338,823 B1 | 1/2002 | Furukawa |
| 6,339,732 B1 | 1/2002 | Phoon |
| 6,347,310 B1 | 2/2002 | Passera |
| 6,383,136 B1 | 5/2002 | Jordan |
| 6,396,583 B1 | 5/2002 | Clare |
| 6,424,860 B1 | 7/2002 | Karlsson |
| 6,435,690 B1 | 8/2002 | Till |
| 6,443,889 B1 | 9/2002 | Groth |
| D467,001 S | 12/2002 | Buczek |
| 6,488,029 B1 | 12/2002 | Toth |
| 6,536,430 B1 | 3/2003 | Smith |

(56) References Cited

U.S. PATENT DOCUMENTS

| | | |
|---|---|---|
| 6,554,238 B1 | 4/2003 | Hibberd |
| 6,571,227 B1 | 5/2003 | Agrafiotis |
| 6,571,792 B1 | 6/2003 | Hendrickson |
| 6,591,694 B2 | 7/2003 | Tsai |
| 6,600,662 B1 | 7/2003 | Emmert |
| 6,647,341 B1 | 11/2003 | Golub |
| 6,650,779 B2 | 11/2003 | Vachtesvanos |
| 6,674,837 B1 | 1/2004 | Taskar |
| 6,692,258 B1 | 2/2004 | Kurzweil |
| 6,692,436 B1 | 2/2004 | Bluth |
| 6,699,187 B2 | 3/2004 | Webb |
| 6,702,754 B2 | 3/2004 | Ogura |
| 6,715,722 B2 | 4/2004 | Roberts |
| 6,735,648 B2 | 5/2004 | Onishi |
| 6,771,172 B1 | 8/2004 | Robinson |
| 6,804,656 B1 | 10/2004 | Rosenfeld |
| 6,824,539 B2 | 11/2004 | Novak |
| 6,829,501 B2 | 12/2004 | Nielsen |
| 6,896,241 B2 * | 5/2005 | Chen ................ E03C 1/0404 137/801 |
| 6,931,795 B1 | 8/2005 | Baloga |
| 6,933,931 B2 | 8/2005 | Lubarsky, Jr. |
| 6,985,762 B2 | 1/2006 | Brashears |
| 7,006,865 B1 | 2/2006 | Cohen |
| 7,013,833 B2 | 3/2006 | Lemberger |
| 7,024,569 B1 | 4/2006 | Wright |
| 7,031,857 B2 | 4/2006 | Tarassenko |
| 7,038,588 B2 | 5/2006 | Boone |
| 7,076,435 B1 | 7/2006 | McKeag |
| 7,081,091 B2 | 7/2006 | Merrett |
| RE39,233 E | 8/2006 | McGrath |
| 7,096,864 B1 | 8/2006 | Mayer |
| 7,111,852 B2 | 9/2006 | Woods |
| 7,117,438 B2 | 10/2006 | Wallace |
| 7,128,709 B2 | 10/2006 | Saruya |
| 7,137,951 B2 | 11/2006 | Pilarski |
| 7,193,233 B2 | 3/2007 | Smith |
| 7,216,802 B1 | 5/2007 | De La Huerga |
| 7,223,007 B1 | 5/2007 | Fredley |
| 7,234,944 B2 | 6/2007 | Nordin |
| 7,256,708 B2 | 8/2007 | Rosenfeld |
| 7,267,666 B1 | 9/2007 | Duchon |
| 7,282,029 B1 | 10/2007 | Poulsen |
| 7,315,825 B2 | 1/2008 | Rosenfeld |
| 7,336,980 B1 | 2/2008 | Kaikuranta |
| 7,360,454 B2 | 4/2008 | Kawashima |
| 7,371,214 B2 | 5/2008 | Kouchi |
| 7,386,340 B2 | 6/2008 | Schlegel |
| 7,468,032 B2 | 12/2008 | Stahmann |
| 7,469,601 B2 | 12/2008 | Sugi |
| D589,959 S | 4/2009 | Han |
| 7,516,924 B2 | 4/2009 | White |
| 7,523,040 B2 | 4/2009 | Kirchhoff |
| 7,529,083 B2 | 5/2009 | Jeong |
| 7,540,187 B1 | 6/2009 | Dillon |
| 7,566,307 B2 | 7/2009 | Inukai |
| 7,621,500 B2 | 11/2009 | Ishizaki |
| 7,751,878 B1 | 7/2010 | Merkle |
| 7,756,722 B2 | 7/2010 | Levine |
| 7,836,882 B1 * | 11/2010 | Rumph et al. ............ 128/203.12 |
| 7,945,452 B2 | 5/2011 | Fathallah |
| 8,027,846 B2 | 9/2011 | Schoenberg |
| 8,033,686 B2 | 10/2011 | Recker |
| 8,147,419 B2 | 4/2012 | Krauss |
| 8,233,272 B2 | 7/2012 | Fidacaro |
| 8,344,847 B2 | 1/2013 | Moberg |
| 8,398,408 B1 | 3/2013 | Hansen |
| 8,413,271 B2 | 4/2013 | Blanchard |
| 8,704,666 B2 | 4/2014 | Baker, Jr. |
| 8,931,702 B2 | 1/2015 | Wekell |
| 8,940,147 B1 | 1/2015 | Bartsch |
| 2001/0001179 A1 | 5/2001 | Healy |
| 2001/0018332 A1 | 8/2001 | Lustila |
| 2001/0027791 A1 | 10/2001 | Wallace |
| 2001/0034475 A1 | 10/2001 | Flach |
| 2002/0026941 A1 | 3/2002 | Biondi |
| 2002/0032386 A1 | 3/2002 | Sackner |
| 2002/0060247 A1 | 5/2002 | Krishnaswamy |
| 2002/0108011 A1 | 8/2002 | Tanha |
| 2002/0161291 A1 | 10/2002 | Kianl |
| 2002/0193679 A1 | 12/2002 | Malave |
| 2002/0196141 A1 | 12/2002 | Boone |
| 2002/0196234 A1 | 12/2002 | Gray |
| 2003/0028118 A1 | 2/2003 | Dupree |
| 2003/0029451 A1 | 2/2003 | Blair |
| 2003/0037786 A1 | 2/2003 | Biondi |
| 2003/0065536 A1 | 4/2003 | Hansen |
| 2003/0076015 A1 | 4/2003 | Ehrenreich |
| 2003/0114836 A1 | 6/2003 | Estes |
| 2003/0117296 A1 | 6/2003 | Seely |
| 2003/0120164 A1 | 6/2003 | Nielsen |
| 2003/0130590 A1 | 7/2003 | Bui |
| 2003/0135087 A1 | 7/2003 | Hickle |
| 2003/0145854 A1 | 8/2003 | Hickle |
| 2003/0171898 A1 | 9/2003 | Tarassenko |
| 2003/0191373 A1 | 10/2003 | Blike |
| 2003/0197614 A1 | 10/2003 | Smith |
| 2003/0209246 A1 | 11/2003 | Schroeder |
| 2003/0210780 A1 | 11/2003 | Pratt |
| 2003/0216621 A1 | 11/2003 | Alpert |
| 2003/0231460 A1 | 12/2003 | Moscovitch |
| 2003/0233129 A1 | 12/2003 | Matos |
| 2004/0011938 A1 | 1/2004 | Oddsen |
| 2004/0015079 A1 | 1/2004 | Berger |
| 2004/0021705 A1 | 2/2004 | Baker |
| 2004/0024303 A1 | 2/2004 | Banks |
| 2004/0032426 A1 | 2/2004 | Rutledge |
| 2004/0054261 A1 | 3/2004 | Kamataki |
| 2004/0054295 A1 | 3/2004 | Ramseth |
| 2004/0102687 A1 | 5/2004 | Brashears |
| 2004/0103001 A1 | 5/2004 | Mazar |
| 2004/0116813 A1 | 6/2004 | Selzer |
| 2004/0117209 A1 | 6/2004 | Brown |
| 2004/0118404 A1 | 6/2004 | Wallace |
| 2004/0147818 A1 | 7/2004 | Levy |
| 2004/0149892 A1 | 8/2004 | Akitt |
| 2004/0153257 A1 | 8/2004 | Munk |
| 2004/0158132 A1 | 8/2004 | Zaleski |
| 2004/0172222 A1 | 9/2004 | Simpson |
| 2004/0186357 A1 | 9/2004 | Soderberg |
| 2004/0220629 A1 | 11/2004 | Kamath |
| 2004/0221077 A1 | 11/2004 | Yen |
| 2004/0236192 A1 | 11/2004 | NecolaShehada |
| 2004/0249298 A1 | 12/2004 | Selevan |
| 2004/0249673 A1 | 12/2004 | Smith |
| 2005/0005932 A1 | 1/2005 | Berman |
| 2005/0010165 A1 | 1/2005 | Hickle |
| 2005/0033124 A1 | 2/2005 | Kelly |
| 2005/0033188 A1 | 2/2005 | Whitaker |
| 2005/0038332 A1 | 2/2005 | Saidara |
| 2005/0038821 A1 | 2/2005 | Wallen |
| 2005/0054920 A1 | 3/2005 | Washburn |
| 2005/0059924 A1 | 3/2005 | Katz |
| 2005/0065417 A1 | 3/2005 | Ali |
| 2005/0113650 A1 | 5/2005 | Pacione |
| 2005/0124866 A1 | 6/2005 | Elaz |
| 2005/0139213 A1 | 6/2005 | Blike |
| 2005/0146431 A1 | 7/2005 | Hastings |
| 2005/0151640 A1 | 7/2005 | Hastings |
| 2005/0177096 A1 | 8/2005 | Bollish |
| 2005/0229110 A1 | 10/2005 | Gegner |
| 2005/0251232 A1 | 11/2005 | Hartley |
| 2006/0004475 A1 | 1/2006 | Brackett |
| 2006/0022096 A1 | 2/2006 | Chan |
| 2006/0042635 A1 | 3/2006 | Niklewski |
| 2006/0058591 A1 | 3/2006 | Garboski |
| 2006/0094970 A1 | 5/2006 | Drew |
| 2006/0142808 A1 | 6/2006 | Pearce |
| 2006/0155206 A1 | 7/2006 | Lynn |
| 2006/0155589 A1 | 7/2006 | Lane |
| 2006/0199618 A1 | 9/2006 | Steer |
| 2006/0226992 A1 | 10/2006 | Al-Ali |
| 2006/0258926 A1 | 11/2006 | Ali |
| 2006/0280621 A1 | 12/2006 | Kinugawa |

(56) References Cited

U.S. PATENT DOCUMENTS

| | | |
|---|---|---|
| 2007/0007418 A1 | 1/2007 | Lubbers |
| 2007/0028921 A1 | 2/2007 | Banner |
| 2007/0032749 A1 | 2/2007 | Overall |
| 2007/0044578 A1 | 3/2007 | Jones |
| 2007/0050715 A1 | 3/2007 | Behar |
| 2007/0051861 A1 | 3/2007 | Teramachi |
| 2007/0060869 A1 | 3/2007 | Tolle |
| 2007/0093784 A1 | 4/2007 | Leonard |
| 2007/0100213 A1 | 5/2007 | Dossas |
| 2007/0107728 A1 | 5/2007 | Ricciardelli |
| 2007/0108291 A1 | 5/2007 | Bhatia |
| 2007/0120763 A1 | 5/2007 | De Paepe |
| 2007/0176931 A1 | 8/2007 | Tivig |
| 2007/0180140 A1 | 8/2007 | Welch |
| 2007/0199388 A1 | 8/2007 | Furkert |
| 2007/0199566 A1 | 8/2007 | Beeri |
| 2007/0255116 A1 | 11/2007 | Mehta |
| 2007/0265533 A1 | 11/2007 | Tran |
| 2007/0276277 A1 | 11/2007 | Booth |
| 2008/0033254 A1 | 2/2008 | Kamath |
| 2008/0039701 A1 | 2/2008 | Ali |
| 2008/0039735 A1 | 2/2008 | Hickerson |
| 2008/0051667 A1 | 2/2008 | Goldreich |
| 2008/0103375 A1* | 5/2008 | Kiani ............................ 600/323 |
| 2008/0154909 A1 | 6/2008 | Dam |
| 2008/0167569 A1 | 7/2008 | Ermes |
| 2008/0170287 A1 | 7/2008 | Champion |
| 2008/0177160 A1 | 7/2008 | Al Ali |
| 2008/0177397 A1 | 7/2008 | Davlin |
| 2008/0181465 A1 | 7/2008 | Sauerwein |
| 2008/0221418 A1 | 9/2008 | Al-Ali |
| 2008/0221495 A1 | 9/2008 | Steffens |
| 2008/0228089 A1 | 9/2008 | Cho |
| 2008/0249376 A1 | 10/2008 | Zaleski |
| 2008/0251003 A1 | 10/2008 | Boston |
| 2008/0267790 A1 | 10/2008 | Gaudet |
| 2008/0271736 A1 | 11/2008 | Leonard |
| 2008/0275309 A1 | 11/2008 | Stivoric |
| 2008/0281168 A1 | 11/2008 | Gibson |
| 2008/0281170 A1 | 11/2008 | Eshelman |
| 2008/0287763 A1 | 11/2008 | Hayter |
| 2008/0294057 A1 | 11/2008 | Parlikar |
| 2008/0310600 A1 | 12/2008 | Clawson |
| 2008/0319331 A1 | 12/2008 | Zizzo |
| 2009/0005703 A1 | 1/2009 | Fasciano |
| 2009/0015116 A1 | 1/2009 | Arceta |
| 2009/0024008 A1 | 1/2009 | Brunner |
| 2009/0054743 A1 | 2/2009 | Stewart |
| 2009/0055735 A1 | 2/2009 | Zaleski |
| 2009/0069642 A1 | 3/2009 | Gao |
| 2009/0076345 A1 | 3/2009 | Manicka |
| 2009/0099480 A1 | 4/2009 | Salgo |
| 2009/0117784 A1 | 5/2009 | Wu |
| 2009/0124239 A1 | 5/2009 | Tsuei |
| 2009/0131805 A1 | 5/2009 | OBrien |
| 2009/0133609 A1 | 5/2009 | Nethken |
| 2009/0149901 A1 | 6/2009 | Jayne |
| 2009/0151720 A1* | 6/2009 | Inoue et al. ............. 128/203.12 |
| 2009/0182204 A1 | 7/2009 | Semler |
| 2009/0192541 A1 | 7/2009 | Ortiz |
| 2009/0193315 A1 | 7/2009 | Gower |
| 2009/0200902 A1 | 8/2009 | McKay |
| 2009/0206713 A1* | 8/2009 | Vilkas ............................ 312/209 |
| 2009/0209849 A1 | 8/2009 | Rowe |
| 2009/0237264 A1 | 9/2009 | Bobey |
| 2010/0004539 A1 | 1/2010 | Chen |
| 2010/0007588 A1 | 1/2010 | Zygmunt |
| 2010/0014229 A1 | 1/2010 | Horie |
| 2010/0056875 A1 | 3/2010 | Schoenberg |
| 2010/0070417 A1 | 3/2010 | Flynn |
| 2010/0073915 A1 | 3/2010 | Nittou |
| 2010/0094096 A1 | 4/2010 | Petruzzelli |
| 2010/0110019 A1 | 5/2010 | Ozias |
| 2010/0137729 A1 | 6/2010 | Pierry |
| 2010/0156655 A1* | 6/2010 | Bullemer ............. G05B 19/406 340/691.6 |
| 2010/0164452 A1 | 7/2010 | Ruan |
| 2010/0175695 A1 | 7/2010 | Jamison |
| 2010/0179400 A1 | 7/2010 | Brauker |
| 2010/0233891 A1 | 9/2010 | Broeksteeg |
| 2010/0238138 A1 | 9/2010 | Goertz |
| 2010/0259881 A1 | 10/2010 | Choi |
| 2010/0261979 A1 | 10/2010 | Kiani |
| 2010/0285771 A1 | 11/2010 | Peabody |
| 2010/0294405 A1 | 11/2010 | Longinotti-Buitoni |
| 2010/0298656 A1 | 11/2010 | McCombie |
| 2010/0298718 A1 | 11/2010 | Gilham |
| 2010/0324380 A1 | 12/2010 | Perkins |
| 2010/0324384 A1 | 12/2010 | Moon |
| 2011/0004071 A1 | 1/2011 | Faiola |
| 2011/0071420 A1 | 3/2011 | St.Pierre |
| 2011/0088694 A1 | 4/2011 | Tobia |
| 2011/0130798 A1 | 6/2011 | Elghazzawi |
| 2011/0138323 A1 | 6/2011 | Skidmore |
| 2011/0152629 A1 | 6/2011 | Eaton |
| 2011/0164074 A1 | 7/2011 | Frank |
| 2011/0190643 A1 | 8/2011 | Zhang |
| 2011/0225771 A1 | 9/2011 | Bartnick |
| 2011/0245579 A1 | 10/2011 | Bruggeman |
| 2011/0257489 A1 | 10/2011 | Banet |
| 2011/0279383 A1 | 11/2011 | Wilson |
| 2011/0279958 A1 | 11/2011 | Clark |
| 2012/0030610 A1 | 2/2012 | DiPerna |
| 2012/0075327 A1 | 3/2012 | Mackenzie |
| 2012/0095778 A1 | 4/2012 | Gross |
| 2012/0105233 A1 | 5/2012 | Bobey |
| 2012/0105774 A1 | 5/2012 | Fletcher |
| 2012/0127103 A1 | 5/2012 | Qualey |
| 2012/0209984 A1 | 8/2012 | Gonzalez-Banos |
| 2012/0232398 A1 | 9/2012 | Roham |
| 2013/0267861 A1 | 10/2013 | Vassallo |

FOREIGN PATENT DOCUMENTS

| | | |
|---|---|---|
| CN | 1983258 A | 6/2007 |
| CN | 101194278 | 6/2008 |
| DE | 9415672 | 11/1994 |
| DE | 102006011151 | 9/2007 |
| EP | 0686900 A2 | 12/1995 |
| EP | 1054338 | 11/2000 |
| EP | 1227752 A1 | 8/2002 |
| EP | 1852060 | 11/2007 |
| GB | 191214095 | 0/1912 |
| GB | 568212 | 3/1945 |
| GB | 2389290 A | 12/2003 |
| JP | 07163527 | 6/1995 |
| JP | 2003210422 | 7/2003 |
| WO | 9415523 | 7/1994 |
| WO | 9918705 | 4/1999 |
| WO | 03091841 | 11/2003 |
| WO | 03102850 | 12/2003 |
| WO | 2006094055 A2 | 9/2006 |
| WO | 2010126916 | 11/2010 |
| WO | 2010126916 A1 | 11/2010 |
| WO | 2011001302 A1 | 1/2011 |
| WO | 2011046636 A1 | 4/2011 |
| WO | 2011047363 A1 | 4/2011 |
| WO | 2011119512 A1 | 9/2011 |
| WO | 2012068564 A2 | 5/2012 |
| WO | 2012068565 A2 | 5/2012 |
| WO | 2012068567 | 5/2012 |
| WO | 2012068568 A2 | 5/2012 |
| WO | 2012083276 A2 | 6/2012 |
| WO | 2012083281 A1 | 6/2012 |
| WO | 2012125135 A1 | 9/2012 |
| WO | 2012128808 A2 | 9/2012 |
| WO | 2012158720 A1 | 11/2012 |
| WO | 2013056171 A2 | 4/2013 |
| WO | 2013173520 A2 | 11/2013 |
| WO | 2013173521 A2 | 11/2013 |

(56) References Cited

FOREIGN PATENT DOCUMENTS

| WO | 2014055660 A1 | 4/2014 |
|---|---|---|
| WO | 2014194193 | 12/2014 |

OTHER PUBLICATIONS

Second Office Action, Chinese Patent Application No. 201180025170X, Issued Jun. 7, 2015.
International Search Report, PCT/US2011/028007, Jul. 11, 2011, International Search Authority.
International Preliminary Report on Patentability, PCT/US2011/028007, Sep. 17, 2013, International Search Authority.
Office Action dated Nov. 21, 2014 for U.S. Appl. No. 13/045,539.
Office Action dated Aug. 6, 2015 for U.S. Appl. No. 13/045,539.
International Search Report for PCT/US2011/065678, Jun. 29, 2012.
International Preliminary Report on Patentability, PCT/US2011/065678, Jun. 18, 2013, International Search Authority.
International Search Report, PCT/US2011/065685, May 8, 2012, International Search Authority.
International Preliminary Report on Patentability, PCT/US2011/065685, Jun. 18, 2013.
Office Action dated Aug. 4, 2015 for U.S. Appl. No. 13/329,219.
Office Action dated Apr. 16, 2015 for U.S. Appl. No. 14/557,135.
Notice of Allowance dated Sep. 3, 2014 for U.S. Appl. No. 13/973,862.
Office Action dated Aug. 28, 2009 for U.S. Appl. No. 11/716,513.
Office Action dated Mar. 23, 2010 for U.S. Appl. No. 11/716,513.
Office Action dated Aug. 1, 2011 for U.S. Appl. No. 11/716,513.
Office Action dated Jul. 2, 2012 for U.S. Appl. No. 11/716,513.
International Search Report for PCT/US2013/063087, Mar. 6, 2014.
Supplementary European Search Report, Nov. 25, 2009, Spacelabs Medical, PCT/US2006/007269.
Schoenberg, Roy, MD; Sands, Daniel Z., MD MPH; Safran Charles, MD; Center for Clinical Computing, Beth Israel Deaconess Medical Center, Harvard Medical School, "Making ICU Alarms Meaningful: a comparison of traditional vs. trend-based algorithms" (AMIA '99 Annual Symposium), 1999, pp. 1-5.
International Search Report for PCT/US06/07269, Aug. 28, 2006.
International Preliminary Report on Patentability, PCT/US2006/007269, Sep. 11, 2007, Spacelabs Medical.
Notice of Allowance dated Oct. 31, 2014 for U.S. Appl. No. 12/114,689.
International Search Report for PCT/US10/32635, Jul. 23, 2010.
Office Action dated Feb. 26, 2015 for U.S. Appl. No. 12/768,714.
Office Action dated Aug. 14, 2014 for U.S. Appl. No. 12/768,714.
Office Action dated Nov. 21, 2013 for U.S. Appl. No. 12/768,714.
Office Action dated Jun. 18, 2012 for U.S. Appl. No. 12/768,714.
Office Action dated Jan. 17, 2013 for U.S. Appl. No. 12/768,714.
Office Action dated Dec. 10, 2014 for U.S. Appl. No. 14/165,193.
Office Action Dated May 31, 2013 for U.S. Appl. No. 13/052,883.
International Search Report for PCT/US2011/029278, Aug. 2, 2011.
International Search Report for PCT/US2011/61557, Apr. 23, 2012.
International Search Report for PCT/US2011/061554, Feb. 14, 2014.
International Search Report for PCT/US2011/061555, Apr. 17, 2012.
International Search Report for PCT/US2011/061558, Aug. 10, 2012.
International Preliminary Report on Patentability for PCT/US2011/061554, Feb. 25, 2014.
IntelliVue Patient Monitor; MP20/30, MP40/50, MP60/70/80/90, Release G.0 with Software Revision G.0x.xx (PHILIPS) Sep. 2008; pp. 4, 10, 19, 20, 46-49, 82, 326, 348, 420, 422, 424, 452; Accessed on Sep. 30, 2013 <http://www.mc.vanderbilt.edu/documents/nursingeducationresources/files/MP20-MP90%20Instructions%20for%20Use%20Manual%20Rev_G_0%20%20English%20M8000-9001K.pdf>.
Office Action dated Nov. 12, 2014 for U.S. Appl. No. 13/300,462.
Notice of Allowance dated Jan. 28, 2015 for U.S. Appl. No. 13/300,478.
International Preliminary Report on Patentability, PCT/US12/38000, Nov. 13, 2013.
International Search Report for PCT/US12/38000, Oct. 23, 2012.
International Search Report for PCT/US10/34025, Aug. 9, 2010.
Notice of Allowance dated Mar. 13, 2015 for U.S. Appl. No. 12/906,081.
International Search Report for PCT/US2012/060125, Apr. 19, 2013.
International Search Report for PCT/US2010/052977, Mar. 18, 2011.
International Search Report for PCT/US2011/065676, Sep. 20, 2012.
Office Action dated Sep. 22, 2014 for U.S. Appl. No. 13/329,186.
Notice of Allowance dated Jan. 8, 2015 for U.S. Appl. No. 13/329,259.
International Search Report for PCT/US2014/040225, Nov. 5, 2014.
Notice of Allowance dated May 27, 2015 for U.S. Appl. No. 14/165,193.
Supplemental Notice of Allowance dated Apr. 20, 2015 for U.S. Appl. No. 12/906,081.
Notice of Allowance dated May 11, 2015 for U.S. Appl. No. 13/300,462.
Office Action dated May 21, 2015 for U.S. Appl. No. 13/300,526.
Office Action dated Jun. 18, 2015 for U.S. Appl. No. 13/329,186.
Office Action dated Jul. 2, 2015 for U.S. Appl. No. 13/895,527.
European Search Report for EP12786443.7, Apr. 15, 2015.
Office Action dated Apr. 7, 2015 for U.S. Appl. No. 13/472,332.
Partial European Search Report for EP 12839321.2, May 26, 2015.

\* cited by examiner

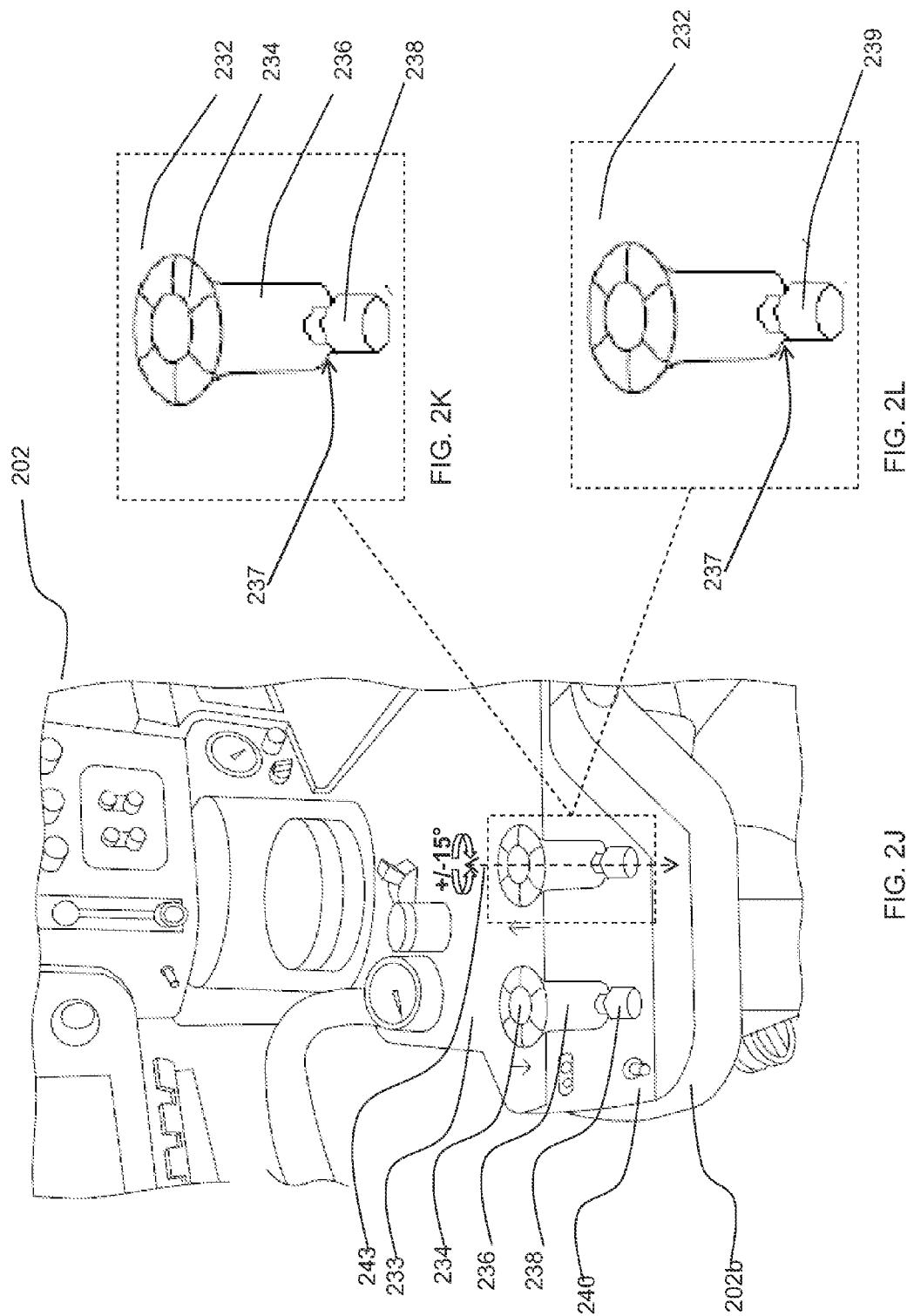

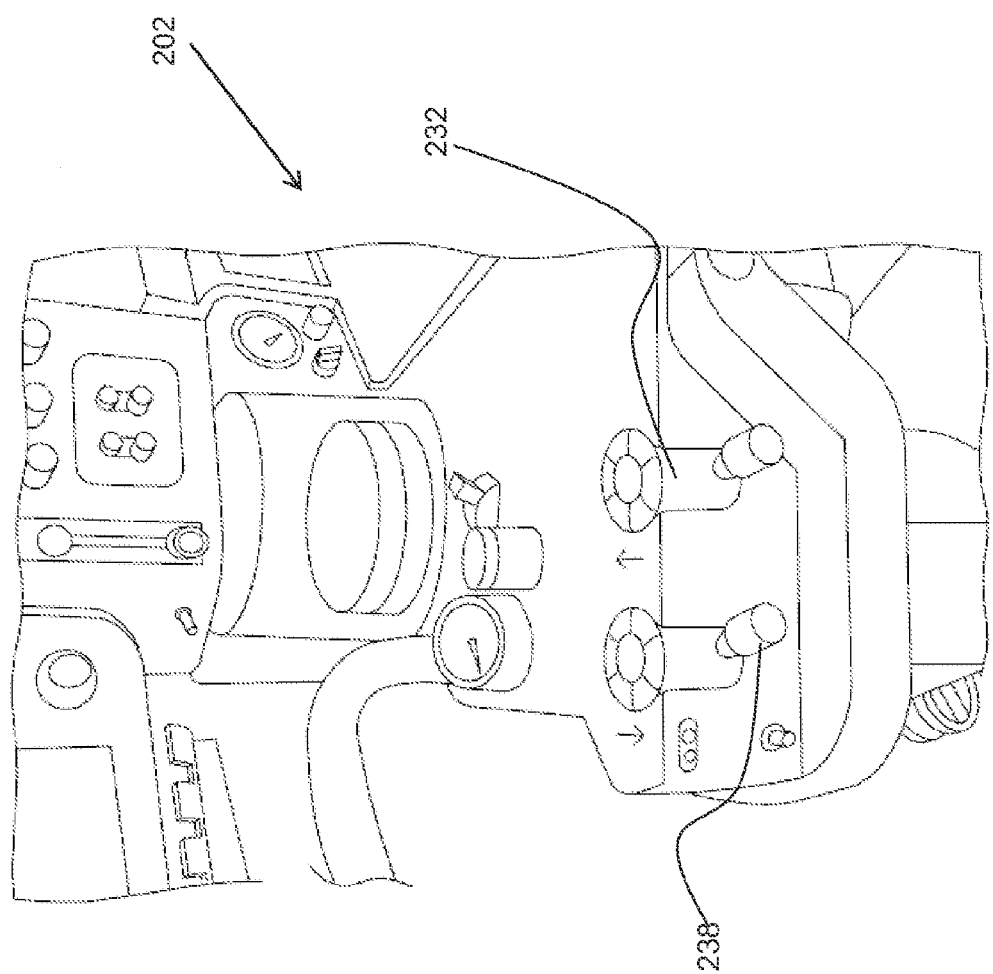

INTEGRATED, EXTENDABLE ANESTHESIA SYSTEM

CROSS-REFERENCE TO RELATED APPLICATIONS

The present application claims priority from U.S. Provisional Patent Application No. 61/546,930, entitled "Integrated, Extendable Anesthesia System", and filed on Oct. 13, 2011, which is hereby incorporated by reference in its entirety.

In addition, the present application claims priority from U.S. Provisional Patent Application No. 61/559,433, entitled "Integrated, Extendable Anesthesia System", and filed on Nov. 14, 2011, which is hereby incorporated by reference in its entirety.

The present application is also a continuation-in-part of U.S. patent application Ser. No. 13/329,186, entitled "Integrated, Extendable Anesthesia System", filed on Dec. 16, 2011 and assigned to the applicant of the present invention, which, in turn, claims priority from U.S. Provisional Patent Application No. 61/424,312, entitled "Integrated, Extendable Anesthesia System", and filed on Dec. 17, 2010 and assigned to the applicant of the present invention, both of which are hereby incorporated by reference in their entirety.

The present application is also a continuation-in-part of U.S. patent application Ser. No. 13/329,219, entitled "Dynamic Graphic Respiratory Communication System", filed on Dec. 17, 2011 and assigned to the applicant of the present invention, which, in turn, relies on U.S. Provisional Patent Application No. 61/424,306, entitled "Animated Display Icons for Use in Anesthesia Systems", filed on Dec. 17, 2010 and assigned to the applicant of the present invention, both of which are hereby incorporated by reference in their entirety.

The present application is also a continuation-in-part of U.S. patent application Ser. No. 13/329,259, entitled "Sliding Track and Pivot Mounting System for Display on Anesthesia Machines", filed on Dec. 17, 2011 and assigned to the applicant of the present invention, which, in turn, relies on U.S. Provisional Patent Application No. 61/424,298, entitled "Sliding Track and Pivot Mounting System for Display on Anesthesia Machines", filed on Dec. 17, 2010 and assigned to the applicant of the present invention, both of which are hereby incorporated by reference in their entirety.

The present application is also a continuation-in-part of U.S. patent application Ser. No. 12/906,081, entitled "Integrated, Extendable Anesthesia System", filed on Oct. 16, 2010 and assigned to the applicant of the present invention, which, in turn, relies on United States Provisional Patent Application No. 61/252,269, entitled "Integrated Anesthesia System", filed on Oct. 16, 2009 and assigned to the applicant of the present invention, both of which are hereby incorporated by reference in their entirety.

Further, PCT/US2010/52977, entitled "Integrated, Extendable Anesthesia System", and filed on Oct. 16, 2010 is herein incorporated by reference in its entirety.

Further, PCT/US2011/65676, entitled "Integrated, Extendable Anesthesia System", and filed on Dec. 16, 2011 is herein incorporated by reference in its entirety.

Further, PCT/US2011/65678, entitled "Dynamic Graphic Respiratory Communication System", and filed on Dec. 17, 2011 is herein incorporated by reference in its entirety.

Further, PCT/US2011/65685, entitled "Sliding Track and Pivot Mounting System for Display on Anesthesia Machines", and filed on Dec. 17, 2011 is herein incorporated by reference in its entirety.

FIELD

The present specification relates to medical systems. More particularly, the present specification relates to an anesthesia system, having an integrated, extendable clinical center and clinician/anesthesia office.

BACKGROUND

Anesthesiologists spend many hours in relatively straightforward cases requiring their vigilance, but little direct clinical action. They are often required to perform various paperwork and documentation activities with only an anesthesia system's tabletop as a work surface. Further, there are typically no storage areas for their documents, files, and personal items, such as cell phones, keys, computers, glasses, wallets, purses, etc. Still further, the clinical usage area of a conventional anesthesia system provides no convenient location for syringes, laryngoscopes and other clinical equipment. Conventional designs of anesthesia systems do not accommodate separation of clinical and clerical functions. Most systems provide only modest amounts of space for the anesthesiologist to conduct their work and that must be shared with space used for clinical setup of drugs and instruments.

Further, most current anesthesia system designs provide no articulation of the breathing circuit connections in order to provide a closer pneumatic and sensor link to a patient. Since most current breathing system designs are completely integrated into the anesthesia system, the entire system must be brought in close proximity to the patient in order to have access to the necessary clinical controls while attending to the patient and their airway. Physical constraints in the operating room (OR), due to, but not limited to, surgery type, OR layout, equipment in use, number of personnel required in room, location of personnel, among other variables, add demands to the positioning and structure of the anesthesia system, particularly with regard to the breathing tube port attachments. Breathing tube port attachments often limit the movement of a system, and if twisted or torqued in the wrong direction, there is a risk of disconnect. This physical architecture drives the need for very small footprint systems, which further limit the space available for the anesthesiologist to work on.

While some conventional prior art anesthesia systems allow for the breathing circuit to be articulated away from the system and be placed in close proximity to the patient, these systems still have most of their clinical controls located on the main body of the system, thus making use quite cumbersome.

For example, a typical, conventional anesthesia system employs a breathing circuit on a double-hinged tubular arm that can be moved away from the anesthesia system trolley. This requires draping of the hoses from the breathing system to the trolley, including fresh gas hoses, ventilator drive gas and scavenging gas—all with the possibility of leakage and disconnection. Further, the ventilation, fresh gas flow (FGF), and vaporizer controls on this system are located back on the trolley and away from the user's direct clinical interaction with the patient. This is disadvantageous in that the user constantly needs to turn away from the patient to observe monitoring or make adjustments. Also, the tubular arm is prone to damage by excessive applied forces from beds, people etc. when in the extended position.

Some newer conventional anesthesia systems have fixed the breathing circuit and the controls on the trolley frame, requiring the user to bring the entire system closer to the patient. This has forced a reduction in system size, thereby reducing the "workspace" available to the anesthesiologists. In addition, the anesthesiologist's work area for documentation and storage is also brought proximate to the patient and the clinical field which is undesirable from a clinical and space management standpoint. In the alternative, a user can position the system further away from the patient, but then must constantly turn back and forth from the patient to observe the monitoring and make setting changes.

Hence, currently available anesthesia systems do not provide the necessary storage area, types, or connectivity required by a modern day anesthesiologist. These include power attachments and storage for personal electronic products such as computers, personal digital assistants (PDAs), data/mobile phone devices, personal music devices, wireless headsets etc. Considering that many anesthesiologists do not have offices within the hospitals in which they work, there is a need to satisfy the user of the anesthesia system with enhanced provisions for conducting their daily activities, including case documentation. Some of the features required such as tape dispensers, lined garbage bins and documentation storage areas, etc., are commonly found in office environments, but nevertheless have not been integrated onto currently available anesthesia systems.

What is therefore needed is an anesthesia system which accommodates separation of clinical and clerical functions. What is also needed is an anesthesia system that allows for a portion of the system to be brought closer to the patient such that clinical controls can be accessed while tending to the patient airway, without compromising office space available to the clinician or crowding the patient area. Further, enhanced flexibility is needed on anesthesia systems at the point of attachment of breathing tubes to increase positioning options.

In addition, conventional anesthesia systems are equipped with alarms designed to alert a user to potential technical problems occurring with the system's behavior. These alarms are typically short text strings that fit within a limited space for display on a video screen provided on the anesthesia system and thus cannot provide detailed information describing the technical issue causing the alarm. Also, these alarm strings may be required to be translated into various localized languages that may not reflect the error as unambiguously as the designers may have envisioned in the English language. Some prior art product designs include posting of additional descriptive text or graphic representations on the video screen describing the potential problem being reflected by the alarm. However, these require more focused attention of the clinical user to read or try to correlate the graphic to the actual system that they are using. Oftentimes, the alarms for anesthesia systems occur during a medical emergency situation, creating a confusing and tense situation for the user. In addition, many users are not familiar with the intricate details of the system's function and cannot easily correlate an alarm message to the necessary corrective actions. Further, many users utilize various manufacturer's systems that may use identical or similar alarm messages to define differing equipment failures, problems or behaviors. Also, the shortened text strings and/or translations used for alarm messages do not present sufficient information to allow the user to adequately diagnose the problem. Hence, an improved alarm display system is required.

Some conventional anesthesia machines are currently fitted with "alarm silence" buttons that can be pressed to silence the audible portion of the system's alarms for periods of up to two minutes. This function ensures that the alarm is specifically acknowledged and directly silenced by the user. However, requiring that the alarm silence button be physically pressed can be frustrating to users who have their hands occupied with the care of the patient (e.g. suctioning, re-intubating, administering drugs). Consequently, what is needed is a method for silencing the alarms in a non-contact, yet still reliable manner. This is especially true when the user is being barraged by a series of alarms all related to a single event or clinical condition. For example, alarms that sound during suction of a patient, low pressure alarms, leakage alarms, low minute volume alarms, and low tidal volume alarms may all be activated at different times.

Further, most conventional anesthesia systems have a function referred to as "$O_2$ Flush". The flush is used principally for refilling the bellows in the presence or upon correction of a leak and for flushing anesthetic agent out of a circle system. Upon activation of the $O_2$ flush for the purposes of refilling the bellows, the bellows fills up with gas that does not contain anesthetic agent. Consequently, the anesthesiologist is required to rebalance the amount of anesthetic agent present in the circuit in order to ensure correct treatment of the patient. Hence, it is desirable to have a single action function in order to provide a high flow similar to that of the $O_2$ flush, while employing levels of mixed gas and anesthetic agent that have been user predefined, in order to enable the bellows to be refilled while preserving the previously set gas mixtures and anesthetic agent levels.

As is commonly known in the art, anesthesia systems with electronic mixing control usually also comprise an emergency bypass valve system that enables a user to set a flow of oxygen in the event of a mixer failure. Some prior art anesthesia systems employ dedicated needle valves to provide the bypass functionality, while others use dedicated mechanical-pneumatic switches to either turn on a bypass valve or revert to an electronic mixer control.

Precise monitoring of the volumes and pressures delivered to ventilated patients is extremely important, especially when presented with pulmonary complications. Measuring these flows and pressures at the patient's airway provides substantial advantages as compared to measuring these parameters inside the anesthesia machine. Current proximal sensors utilize pneumatic or electrical connections back to the anesthesia system. This connection creates significant bulk and weight at the patient's airway that can lead to disconnections and physical pulling on the patient's endotracheal tube. Consequently, many users perceive this to be a significant disadvantage of proximal sensors and choose to perform patient monitoring and delivery control at a less desirable location closer to the anesthesia system. Further, the use of differential pressure type flow sensors and proximal airway pressure sensors require the use of pneumatic tubes to be attached to the anesthesia system. These tubes can be kinked or occluded by wheels of equipment being moved in the OR, causing data loss on the sensor channel. Pneumatic tubes can also be a source of gas leakage from the breathing circuit and their length can result in flow measurement errors due to pneumatic signal transit, common mode errors. Hence, a single, small sensor solution for proximal placement without tubes or connections back to the anesthesia system is therefore needed.

Contemporary anesthetic vaporizer systems contain valves and/or wick systems for transitioning liquid anesthetic agent into a gaseous form. Typically, these systems provide an agent concentration level of 0-10% (although sometimes higher for Suprane) of the gas being used as "fresh gas" or "make up" gas in a circle breathing system. Contemporary devices are rather complex and require precision mechanical components or flow control systems to operate, creating a relatively high cost device. For example, U.S. Pat. No. 6,155,255, assigned to Louis Gibeck AB and herein incorporated by reference in its entirety, proposes a "vaporizer, comprising a vaporizing chamber which includes a gas inlet and a gas outlet and which accommodates a porous liquid delivery device adapted to expose a liquid to the vaporizing chamber for vaporization of said liquid, wherein said porous liquid delivery device is connected to a liquid supplier that communicates with an external liquid source, wherein said porous liquid delivery device is adapted to expose said liquid exclusively through pores in said porous liquid delivery device; and wherein said liquid supplier includes a liquid quantity regulator." and a "method of vaporizing a liquid, which comprises the steps of: delivering a liquid from an external liquid source to a liquid delivery device; and exposing said liquid in said liquid delivery device to a flowing gas for vaporization of the liquid in contact with the gas, including, conducting said liquid to pores in said liquid delivery device exposing said liquid to the gas exclusively through said pores in said liquid delivery device, and regulating the supply of liquid delivered to said liquid delivery device."

It is desirable to know the amount of gas flow being moved through the evaporator and have direct means for determining the concentration of anesthetic in the breathable gases that is being produced. It is also desirable to precisely measure the amount of liquid flow into the evaporator for the purposes of computing agent concentrations. Hence, means of incorporating a known vaporizer system into an anesthesia system are required.

SUMMARY

In one embodiment, the present specification is directed toward an anesthesia system having an integrated, extendable clinical center and clinician/anesthesia office that accommodates physical separation of clinical and clerical functions. In another embodiment, the present specification is directed toward an anesthesia system that allows for a portion of the system to be brought closer to the patient such that clinical controls can be accessed while tending to the patient airway, without compromising office space available to the clinician or crowding the patient area.

In one embodiment, the present specification is directed toward an anesthesia delivery system comprising a first section comprising support for at least one clinical control and at least one patient connection for providing therapy to a patient, wherein said at least one patient connection includes a breathing circuit connection, comprising at least one limb, wherein the at least one limb may be inspiratory, expiratory or a combination thereof and a second section, comprising a base portion for supporting and housing the first section and further comprising supports for pneumatic and electrical connections and wherein the first section is extendable relative to the second section, exposing at least one workspace when extended, and wherein the second section is pneumatically connected to the first section via a suction supply and at least one anesthesia gas supply.

In one embodiment, the first section of the present specification further comprises a clinical center section which includes at least one of: a ventilator display; a physiological monitor; a physiologic monitor display; respiratory gas analysis and connections; patient suction controls; auxiliary oxygen controls and connections; fresh gas flow mixing and controls; vaporizers and attachment back bar; syringe pump mounts; expandable clinical workspace; and wireless sensor docking.

In one embodiment, the second section of the present specification further comprises an anesthesia office section which includes at least one of: space for an anesthesiologist's documentation, storage and personal effects; work surfaces to support both the standing and sitting behavior of the anesthesiologist; pull-out trays that allow for a computer keyboard; personal electrical equipment connectors on the front of the anesthesia office section; foot rest with angled front to allow knee room; and, lighting of work areas for operation in low light conditions.

In one embodiment of the present specification, the second section further comprises a base portion which includes a sliding track upon which the first section is rotatably extendable from a fully integrated position into a first extended position relative to the second section.

In one embodiment, the first section is rotatably extendable from the second section at an angle ranging from 0 degrees to 45 degrees and optionally, rotatably extendable in angular increments.

In another embodiment of the anesthesia delivery system of the present specification, the first section is linearly extendable from the second section, in a range of 0 to 14.5 inches, into a second extended position relative to the second section.

In yet another embodiment of the anesthesia delivery system of the present specification, the first section is, from a fully integrated position, both rotatably and linearly extendable away from the second section such that it is in a third and fully extended position. In one embodiment, the anesthesia delivery system of the present specification further comprises at least one floor contact point providing load-bearing support. In one embodiment, the at least one floor contact point is a rotating trackball. In another embodiment, the at least one floor contact point is a rotating caster wheel having multiple rollers for both inline and side to side movement. In yet another embodiment, the at least one floor contact point is configured with appropriate geometry to move obstructions on the floor as the first section is extended away from the second section. In one embodiment of the anesthesia delivery system of the present specification, a user-initiated actuation results in a motorized movement of the first section relative to the second section. In another embodiment, the motorized movement of the first section is automatically stopped if an obstruction to the movement is detected. In one embodiment, the obstruction is detected by detecting a change in electric current drawn by a movement motor contained within the system. In yet another embodiment, an audio, visual, or audio-visual alarm is provided if an obstruction to the movement is detected.

In one embodiment, the present specification is directed towards an anesthesia delivery system having a first section comprising a housing including a planar surface above a ground level, wherein the planar surface is provided on a bottom portion of the first section; a second section, comprising a base portion including a planar surface having a height in a range of two to five feet for providing a workspace surface, at least one pneumatic connection, and at least one electrical connection, wherein the second section is pneumatically connected to the first section by a suction supply line and at least one anesthesia gas supply line, and wherein the first section is movable relative to the second section; and at least one breathing circuit attachment port, wherein said breathing circuit attachment port is a rotating body comprising a rotating cap embedded within the planar surface of the housing of the first section, a port housing extending downward from the rotating cap and embedded within the housing of the first section, and at least one limb, wherein the at least one limb may be inspiratory, expiratory, or a combination thereof.

In one embodiment, the port housing is cylindrical in shape and defines a space for receiving a gas. In embodiment, the external diameter of the cylindrical port housing is in the range of 17 mm to 27 mm while the inner diameter of the cylindrical port housing is in the range of 10 mm to 20 mm. In one embodiment, the cylindrical port housing is radially sealed using at least one O-ring.

In one embodiment, the at least one limb on the breathing circuit attachment port is an inlet connected to an anesthesia gas supply line for receiving gas and an outlet for connecting a proximal end of a breathing tube wherein a distal end of the breathing tube is connected to a patient.

In one embodiment, the at least one breathing circuit attachment port is rotated in a range of −15 degrees to +15 degrees about an axis perpendicular to the planar surface of the bottom portion of the first section and extending through a center point of the breathing circuit attachment port.

In one embodiment, the at least one breathing circuit attachment port is removable for cleaning.

In one embodiment, the rotating cap of the breathing circuit attachment port embedded within the planar surface of the housing of the first section is translucent so that action of the breathing circuit check valves can be monitored by a user. In another embodiment, the rotating cap of the breathing circuit attachment port embedded within the planar surface of the housing of the first section is translucent and further equipped with information projection lighting to indicate when flow is moving through the port.

In an optional embodiment of the anesthesia delivery system of the present specification, the patient is connected to the system via a circle-less breathing circuit which comprises an inspiratory and an expiratory valve, wherein fresh gas is injected through the inspiratory valve, mixed with an injected agent, delivered to a patient and then led out via the expiratory valve and wherein the inspiratory valve further comprises a plurality of control valves to blend at least two of oxygen, air and nitrous oxide directly into the breathing circuit.

In one embodiment, the anesthesia system of the present specification further comprises an information projection lighting system for indicating the status of a control of the system by directly illuminating the controlled function.

In one embodiment, the present specification is an anesthesia delivery system comprising: a first section comprising support for at least one clinical control and at least one patient connection for providing therapy to a patient, wherein said at least one patient connection includes a breathing circuit connection, comprising at least one limb, wherein the at least one limb may be inspiratory, expiratory or a combination thereof; a second section comprising a base portion for supporting and housing the first section and further comprising supports for pneumatic and electrical connections, wherein the first section is linearly and rotatably extendable relative to the second section, and wherein the second section is pneumatically connected to the first section via a suction supply and at least one anesthesia gas supply; and an information projection lighting system for indicating the status of at least one function of the system by direct illumination.

In one embodiment, the information projection lighting system further comprises adjustable lighting, wherein the lighting can be adjusted by color, intensity or flash rate.

In another embodiment, the information projection lighting system of the present specification indicates an anomalous operational condition of the anesthesia system by direct illumination of the portion of the anesthesia delivery apparatus suspected of causing the anomalous operating condition.

In another embodiment, the information projection lighting system indicates when a ventilator within the anesthesia system is in an active state by illuminating a bellows of the ventilator.

In yet another embodiment, the information projection lighting system indicates when a ventilator within the anesthesia system is in an inactive state by illuminating an adjustable pressure-limiting (APL) valve of the ventilator.

In yet another embodiment, the information projection lighting system indicates when a ventilator within the anesthesia system is in an inactive state by illuminating a pressure gauge of the ventilator.

In yet another embodiment, the information projection lighting system indicates when a ventilator within the anesthesia system is in an inactive state by illuminating a bag arm of the ventilator.

In yet another embodiment, the information projection lighting system illuminates a common gas outlet port of the anesthesia system when controls are set to have gas emerge from the common gas outlet port.

In yet another embodiment, the information projection lighting system illuminates an auxiliary flow tube if auxiliary flow has been turned on.

In yet another embodiment, the information projection lighting system illuminates a $CO_2$ absorbent canister if the canister is disengaged from the breathing circuit and/or if there is an alarm for high $CO_2$ in the respiratory gas.

In yet another embodiment, the information projection lighting system illuminates a side stream respiratory gas monitor water trap if the respiratory gas monitor is alarming to indicate an obstruction.

In another embodiment, the present specification is directed toward an anesthesia delivery system comprising a first section comprising housing for at least one clinical control and at least one patient connection for providing therapy to a patient, wherein said at least one patient connection includes a breathing circuit connection, comprising at least one limb, wherein the at least one limb may be inspiratory or expiratory or a combination thereof; and a second section comprising a base portion for supporting the first section, a planar workspace surface, at least one pneumatic connection and at least one electrical connection, wherein the second section is pneumatically connected to the first section by a suction supply line and at least one anesthesia gas supply line and wherein the first section is movable relative to the second section. The planar workspace surface is of sufficient length and width to enable an anesthesiologist to comfortably take notes. In various embodiments, the planar workspace surface measures 3 in wide×3 in long, 8.5 in wide×11 in long, 11 in wide×14 in long, or, any dimensional increment therein (3 to 11 inches wide×3 inches to 14 inches long).

Optionally, in one embodiment, the second section comprises an area for housing at least one of: a storage space, a first work surface at a first elevation, a second work surface at a second elevation, wherein the first elevation is higher than the second elevation; at least one pull-out tray; at least one electrical equipment connector wherein said connector interface extends outward toward the front of said second section; an angled planar surface at said base of the second section adapted to function as a foot rest; and, lighting. The first work surface at a first elevation is preferably a planar workspace surface of sufficient length and width to enable an anesthesiologist to comfortably take notes. In various embodiments, the planar workspace surface measures 3 in wide×3 in long, 8.5 in wide×11 in long, 11 in wide×14 in long, or, any dimensional increment therein (3 to 11 inches wide×3 inches to 14 inches long). In one embodiment, the first work surface at a first elevation is of a sufficient elevation to allow an average size person to stand and write on said surface. In various embodiments, the first elevation is three feet or higher from ground level. The second work surface at a second elevation is preferably a planar workspace surface of sufficient length and width to enable an anesthesiologist to comfortably take notes. In various embodiments, the planar workspace surface measures 3 in wide×3 in long, 8.5 in wide×11 in long, 11 in wide×14 in long, or, any dimensional increment therein (3 to 11 inches wide×3 inches to 14 inches long). In one embodiment, the second work surface at a second elevation is of a sufficient elevation to allow an average size person to sit and write on said surface. In various embodiments, the second elevation is three feet or lower from ground level and preferably at least two feet from ground level Optionally, in one embodiment, the base portion of the second section comprises a sliding track upon which the first section is rotatably extendable from a first position to a second position. In the first position, the second section and the first section are integrated into each other. In various embodiments, the second and first sections integrate or pull into each other by having the second section embed itself into the first section or the first section embed itself into the second section, wherein the external housings of both the first and section sections meet to prevent any access into the internal workspace areas of the second section. In the second position, the first section extends away from said second section and provides physical access to the planar workspace surface.

Optionally, in one embodiment, the first section is rotatably extendable from the second section at an angle ranging from 0 degrees to 45 degrees. The first section is rotatably extendable in angular increments. The first section is configured to linearly extend from the second section in order to move from a first position to a second position, as described above. The first section is linearly extendable from the second section at a distance ranging from 0 to 14.5 inches.

Optionally, in one embodiment, the first section is, from a fully integrated position, both rotatably and linearly extendable away from the second section such that it is in an extended position. Optionally, in one embodiment, the delivery system comprises at least one floor contact point providing load-bearing support. In one embodiment, the at least one floor contact point is a rotating trackball. In another embodiment, the at least one floor contact point is a rotating caster wheel having multiple rollers for both inline and side to side movement. Optionally, in one embodiment, a user-initiated actuation results in a motorized movement of the first section relative to the second section. In one embodiment, the motorized movement of the first section is automatically stopped if an obstruction to the movement is detected by a controller, wherein said controller is configured to detect a change in electric current drawn by a movement motor causing said motorized movement. In one embodiment, an audio, visual, or audio-visual alarm is provided if an obstruction to the movement is detected.

Optionally, in one embodiment, the patient is connected to the system via a circle-less breathing circuit which comprises an inspiratory and an expiratory valve, wherein fresh gas is injected through the inspiratory valve, mixed with an injected agent, delivered to a patient and then led out via the expiratory valve and wherein the inspiratory valve further comprises a plurality of control valves to blend at least two of oxygen, air, or nitrous oxide directly into the breathing circuit.

Optionally, in one embodiment, the system further comprises a lighting system for indicating the status of a control of the system by directly illuminating the controlled function. In one embodiment, the lighting system only illuminates a control for which status has changed, is in an alert condition, or which otherwise requires the attention of the physician, while not illuminating any other control.

Optionally, in one embodiment, the first section and second section are in physical communication with each other only at the point(s) of the structure(s) responsible for enabling the rotating or linear movement. In another embodiment, the first section and second section are not physically connected at any point other than where the second section supports the first section for the purpose of enabling the rotating or linear movement.

In another embodiment, the anesthesia delivery system comprises a first section comprising support for at least one clinical control and at least one patient connection for providing therapy to a patient, wherein said at least one patient connection includes a breathing circuit connection, comprising at least one limb, wherein the at least one limb may be inspiratory, expiratory or a combination thereof; a second section comprising a base portion for supporting and housing the first section and at least one pneumatic or electrical connection, wherein the first section is linearly, rotatably or both linearly and rotatably extendable relative to the second section, and wherein the second section is pneumatically connected to the first section via a suction supply line or an anesthesia gas supply line; and, a lighting system for indicating the status of at least one function of the system by direct illumination.

In another embodiment, the present specification is directed toward a user interface alarm lighting feature for use in anesthesia delivery systems, comprising a lighting strip provided on a graphical user interface (GUI) of said anesthesia system to enable a user to quickly determine if an alarm is active and the priority level of said active alarm, further wherein the location and color of said lighting strip determine said priority of said alarm.

In another embodiment, the present specification is directed toward a user interface alarm limit revert feature for use in anesthesia delivery systems, said anesthesia delivery system comprising an "auto-limits" function activation that automatically adjusts said system's alarm limits around currently monitored values based on a predefined algorithm, wherein said revert feature reverts the alarm(s) and thus, alarm limits, into a pre-auto-limit activation state.

In another embodiment, the present specification is directed toward an emergency bypass valve system for use in anesthesia delivery systems, comprising a dual position knob which, in a first position, corresponds to an active electronic mixing control and, in a second position, corresponds to an active emergency bypass valve, further wherein a pre-determined amount of oxygen flow is provided when said dual position knob is moved into said second position.

In another embodiment, the present specification is directed toward a self-activating auxiliary common gas outlet (ACGO) port for use in anesthesia delivery systems, wherein said ACGO port is in an inactive state when said ACGO port is in a first vertical, downward facing position and said AGCO port is activated by rotation of said ACGO port into a second horizontal, forward facing position. In one embodiment, the auxiliary common gas outlet (AGCO) port is illuminated when said ACGO port is in said second position.

The present specification is also directed toward an anesthesia delivery system, comprising: a first section comprising housing for at least one clinical control and at least one patient connection for providing therapy to a patient, wherein said at least one patient connection includes a breathing circuit connection, comprising at least one limb, wherein the at least one limb may be inspiratory or expiratory or a combination thereof; a second section, comprising a base portion for supporting the first section, a planar workspace surface, at least one pneumatic connection and at least one electrical connection, wherein the second section is pneumatically connected to the first section by a suction supply line and at least one anesthesia gas supply line and wherein the first section is movable relative to the second section; and, wherein the first section, the second section, or both the first section and the second sections contain means for ensuring that at least one planar workspace surface remains free of contaminants.

In one embodiment, the means for ensuring at least one planar workspace surface remains free of contaminants comprises close tolerance or flexible seals at the point(s) where the first section is movable relative to the second section. In one embodiment, the close tolerance or flexible seals comprise one of the following types: bulb seals, wiper type seals, or flexible foam seals.

In another embodiment, the means for ensuring at least one planar workspace surface remains free of contaminants comprises antimicrobial treatment(s), further wherein said antimicrobial treatment(s) is applied to said at least one planar surface. In another embodiment, the means for ensuring at least one planar workspace surface remains free of contaminants comprises a removable decal affixed to said at least one planar surface, further wherein said decal is treated with an antimicrobial treatment. In one embodiment, the antimicrobial treatment comprises silver ion.

In another embodiment, the means for ensuring at least one planar workspace surface remains free of contaminants comprises a film-based solution having an intrinsic microgeometry which when applied on a surface makes said surface resistant to microbe growth, wherein said solution is applied to said at least one planar workspace.

In another embodiment, the means for ensuring at least one planar workspace surface remains free of contaminants comprises at least one ultraviolet (UV) light source. In one embodiment, the at least one ultraviolet (UV) light source is attached within or onto said anesthesia delivery system. In one embodiment, the at least one ultraviolet (UV) light source is activated when said first section is moved relative to said section and/or at predetermined intervals. In another embodiment, the at least one ultraviolet (UV) light source comprises a wand-like device and the anesthesia system further comprises access holes and/or removable covers, wherein said wand-like device can be inserted into said access holes and/or waved over components exposed by removal of said removable covers.

In another embodiment, the means for ensuring at least one planar workspace surface remains free of contaminants comprises a flexible antibacterial pad attached to the bottom of said first section, wherein said pad is conditioned with an antibacterial cleanser, and wherein sad pad rubs and thereby cleanses said at least one planar surface as said first section is moved relative to said second section. In one embodiment, the antibacterial cleanser comprises isopropyl alcohol. In one embodiment, the antibacterial pad is temporary and is periodically replaced. In another embodiment, the antibacterial pad is permanent and is periodically reconditioned with said antibacterial cleanser.

The present specification is also directed toward an anesthesia delivery system, comprising: a first section comprising housing for at least one clinical control and at least one patient connection for providing therapy to a patient, wherein said at least one patient connection includes a breathing circuit connection, comprising at least one limb, wherein the at least one limb may be inspiratory or expiratory or a combination thereof; a second section, comprising a base portion for supporting the first section, a planar workspace surface, at least one pneumatic connection and at least one electrical connection, wherein the second section is pneumatically connected to the first section by a suction supply line and at least one anesthesia gas supply line and wherein the first section is movable relative to the second section; and, a user interface alarm lighting feature, wherein a lighting strip is provided on a graphical user interface (GUI) of said anesthesia system to enable a user to quickly determine if an alarm is active and the priority level of said active alarm, further wherein the location and color of said lighting strip determine said priority of said alarm.

In one embodiment, the anesthesia delivery system further comprises a user interface alarm limit revert feature, wherein said anesthesia delivery system comprising an "auto-limits" function activation that automatically adjusts said system's alarm limits around currently monitored values based on a predefined algorithm, further wherein said revert feature reverts the alarm(s) and thus, alarm limits, into a pre-auto-limit activation state.

In one embodiment, the anesthesia delivery system further comprises an emergency bypass valve system which enables a user to set a flow of oxygen in the event of a mixer failure, wherein said emergency bypass valve system comprises a dual position knob, which, in a first position, corresponds to an active electronic mixing control and, in a second position, corresponds to an active emergency bypass valve, further wherein a pre-determined amount of oxygen flow is provided when said dual position knob is moved into said second position.

In one embodiment, the anesthesia delivery system further comprises a self-activating auxiliary common gas outlet (ACGO) port. In one embodiment, the auxiliary common gas outlet (ACGO) port measures in the range of 17 to 27 mm in external diameter. In one embodiment, the auxiliary common gas outlet (ACGO) port measures in the range of 10 to 20 mm in internal diameter. In one embodiment, the auxiliary common gas outlet (ACGO) port is in an inactive state when said ACGO port is in a first vertical, downward facing position and said AGCO port is activated by rotation of said ACGO port into a second horizontal, forward facing position. In one embodiment, the auxiliary common gas outlet (AGCO) port is illuminated when said ACGO port is in said second position.

The present specification is also directed toward a user interface alarm lighting feature for use in anesthesia delivery systems, wherein a lighting strip is provided on a graphical user interface (GUI) of said anesthesia system to enable a user to quickly determine if an alarm is active and the priority level of said active alarm, further wherein the location and color of said lighting strip determine said priority of said alarm.

The aforementioned and other embodiments of the present specification shall be described in greater depth in the drawings and detailed description provided below.

BRIEF DESCRIPTION OF THE DRAWINGS

These and other features and advantages of the present specification will be further appreciated, as they become better understood by reference to the detailed description when considered in connection with the accompanying drawings, wherein:

FIG. 2J is an illustration of one embodiment of at least one swiveling breathing circuit attachment port in a first, default configuration, having a breathing tube connection outlet positioned perpendicular to the front of the clinical center (CC);

FIG. 2K is an expanded, front view of the swiveling breathing circuit attachment port of the present invention, shown in FIG. 2J;

FIG. 2L is an expanded, back view of the swiveling breathing circuit attachment port of the present invention, shown in FIGS. 2J and 2K;

FIG. 2M is an illustration depicting one embodiment of at least one swiveling breathing circuit attachment port in a second configuration, having a breathing tube connection outlet rotated fully toward the right side of the clinical center (CC);

DETAILED DESCRIPTION

The present specification is directed toward an anesthesia system having an integrated, extendable clinical center and clinician/anesthesia office. The present specification is directed toward an anesthesia system which accommodates physical separation of clinical and clerical functions. The present specification is also directed toward an anesthesia system that allows for a portion of the system to be brought closer to the patient such that clinical controls can be accessed while tending to the patient airway, without compromising office space available to the clinician or crowding the patient area.

The present application is directed toward multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present application is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

Figure 1A:
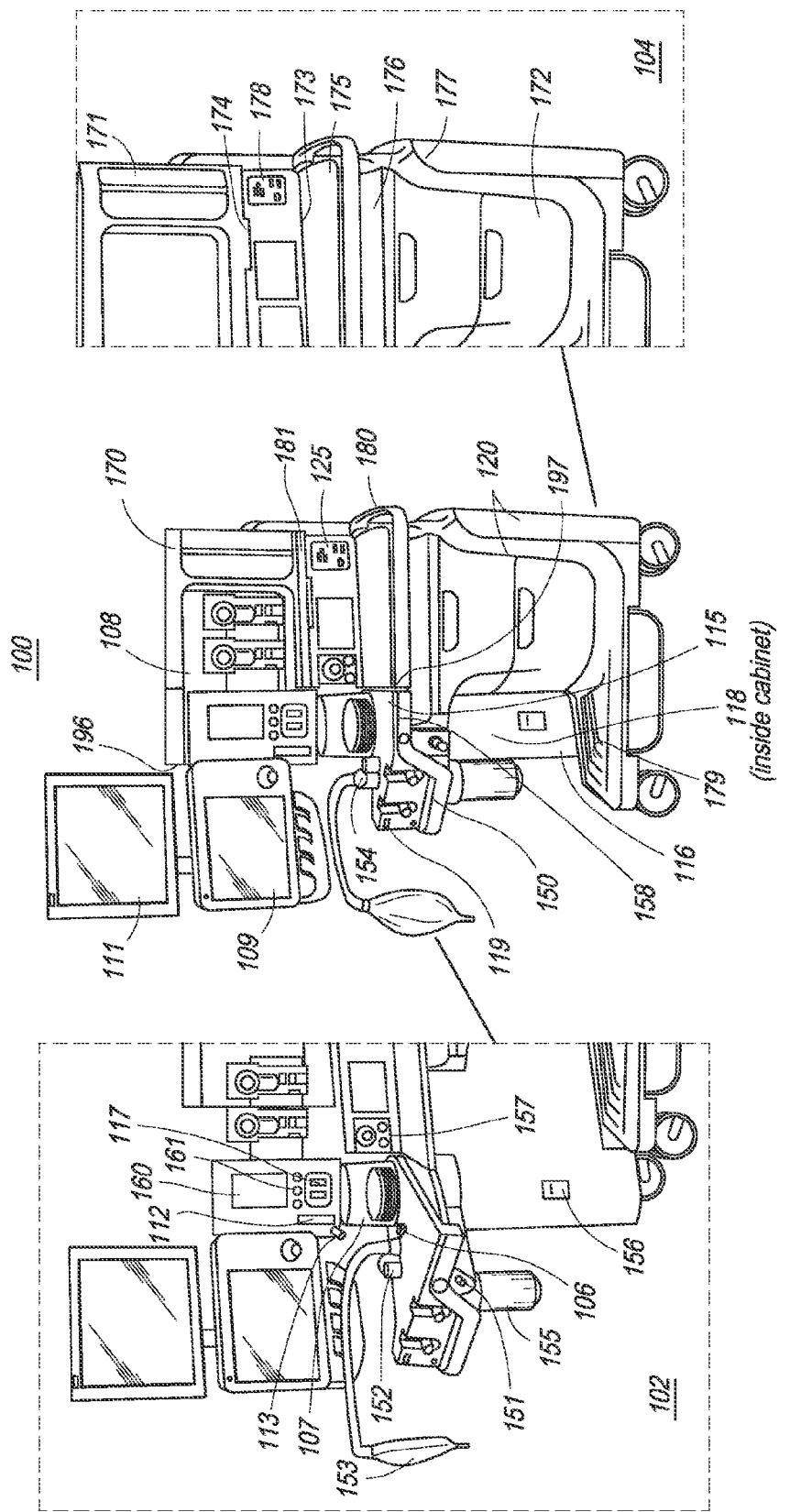
FIG. 1A is an overview illustration of the anesthesia system of the present specification, with cut-away diagrams of the clinical center (CC) and the anesthesia office (AO) sections.
Figure 1B:
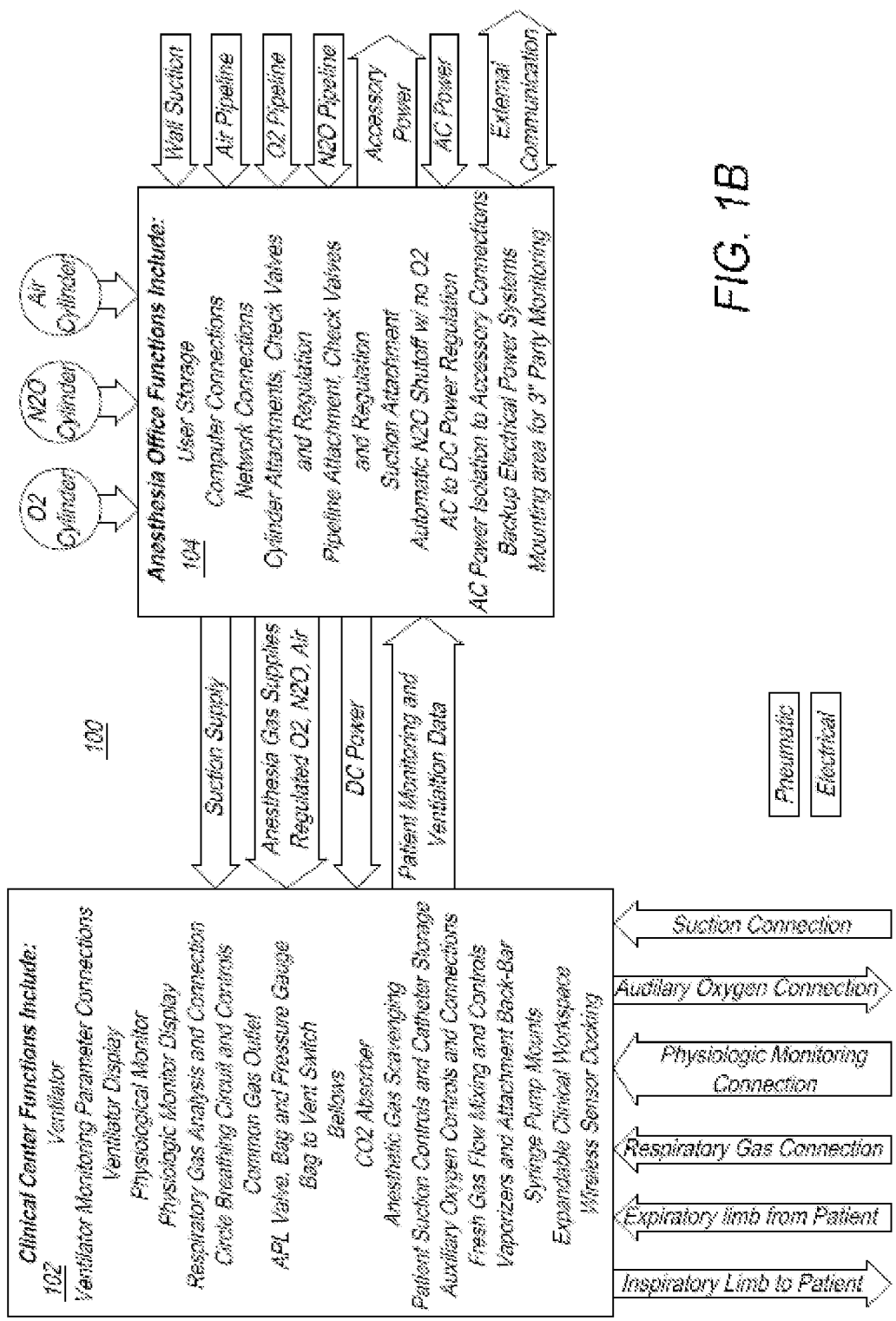
FIG. 1B is a system flow diagram of the anesthesia system of the present specification.

FIG. 1A and FIG. 1B illustrate one embodiment of the anesthesia system 100 of the present specification, which allows for proper workflow management of the anesthesiologist's work area. The anesthesia system 100 is a small, compact system configuration, and can be easily moved in close proximity to a patient's bedside. In one embodiment, the present specification provides an anesthesia system that comprises a first section 102 and a second section 104, where the first section 102 includes support for at least one clinical control and at least one patient connection for providing therapy to a patient. In one embodiment, the patient connection includes a breathing circuit. In one embodiment, the second section 104 comprises a base portion for supporting and receiving the first section 102. In addition, the second section 104 comprises pneumatic and electrical connections. In one embodiment, the second section 104 is pneumatically connected to the first section 102 via a suction supply and at least one anesthesia gas supply. In one embodiment, the first section 102 is extendable relative to the second section 104 and is capable of moving on a sliding track out from the base provided on the second section 104. In one embodiment, the track is positioned at an oblique angle, to the front face and base of the second section, allowing movement of the first section forward and left from the second section.

In one embodiment, the first section 102 comprises a clinical center (CC) section and the second section 104 comprises an anesthesia office (AO) section.

Clinical Center (CC) and Clinician/Anesthesia Office (AO)

In one embodiment, the "clinical center" (CC) section 102 of the anesthesia system 100 illustrated in FIG. 1A comprises at least one clinical control and at least one patient connection for providing therapy to a patient.

As shown in the upper level system architecture of FIG. 1B, the anesthesia system 100 comprises both pneumatic and electrical connections. The clinical center (CC) 102 is, in operation, pneumatically connected to the patient via at least one breathing circuit connection. In one embodiment, the breathing circuit comprises at least one or both of an inspiratory limb and an expiratory limb. "Inspiratory limbs" and "expiratory limbs" are standard components of most ventilation and anesthesia systems and are thus well known in the art and not further defined herein. In one embodiment, the inspiratory and expiratory portions of the circuit are coaxial and housed in one limb.

Further, the functional system architecture of the CC 102 utilizes a plurality of connections such as regulated supply pressure (e.g. 30 PSI) for $O_2$, nitrous oxide ($N_2O$) and air, wall suction, DC power, and data communications (e.g. internal system or hospital network) from the AO 104. The CC 102 provides patient monitoring and ventilation data to the AO 104.

In one embodiment, CC 102 includes a pneumatic connection for respiratory gas that is fed into the system of the present specification via a sample line. CC 102 also includes a pneumatic auxiliary oxygen connection that is directed away from CC 102. In addition, CC 102 includes a pneumatic suction connection to the anesthesia office 104 of the present specification. In one embodiment, CC 102 is electrically connected to physiologic monitoring equipment.

Figure 1C:
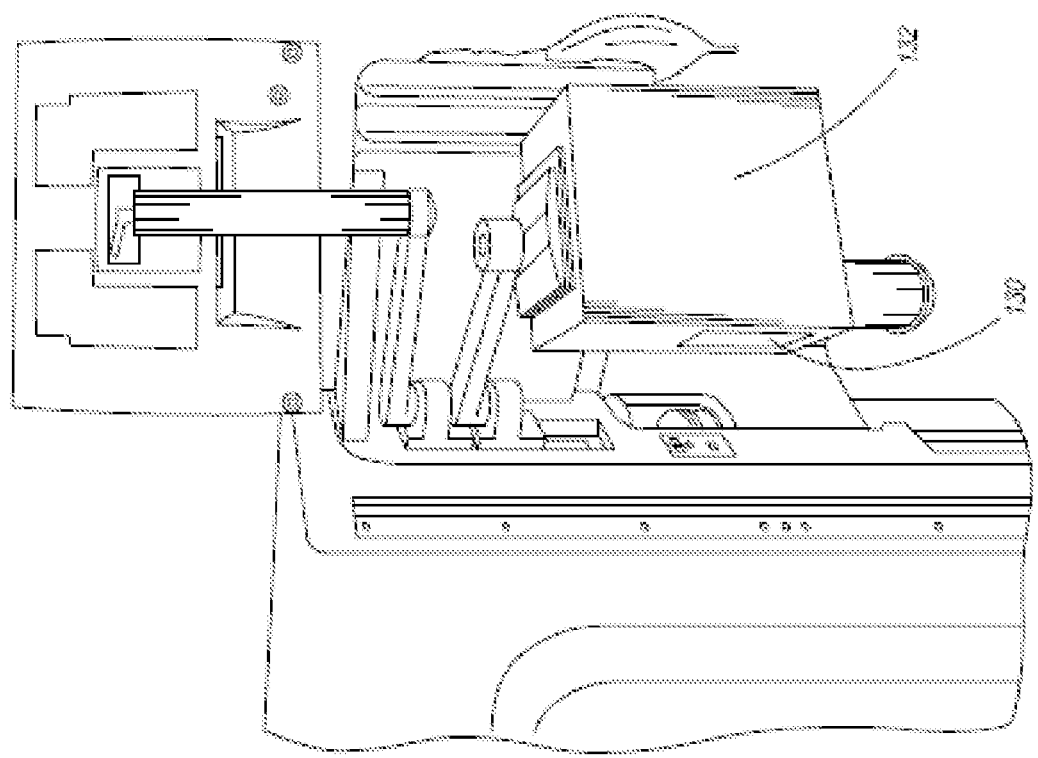
FIG. 1C is a backside illustration of the anesthesia system of the present specification.
Figure 1D:
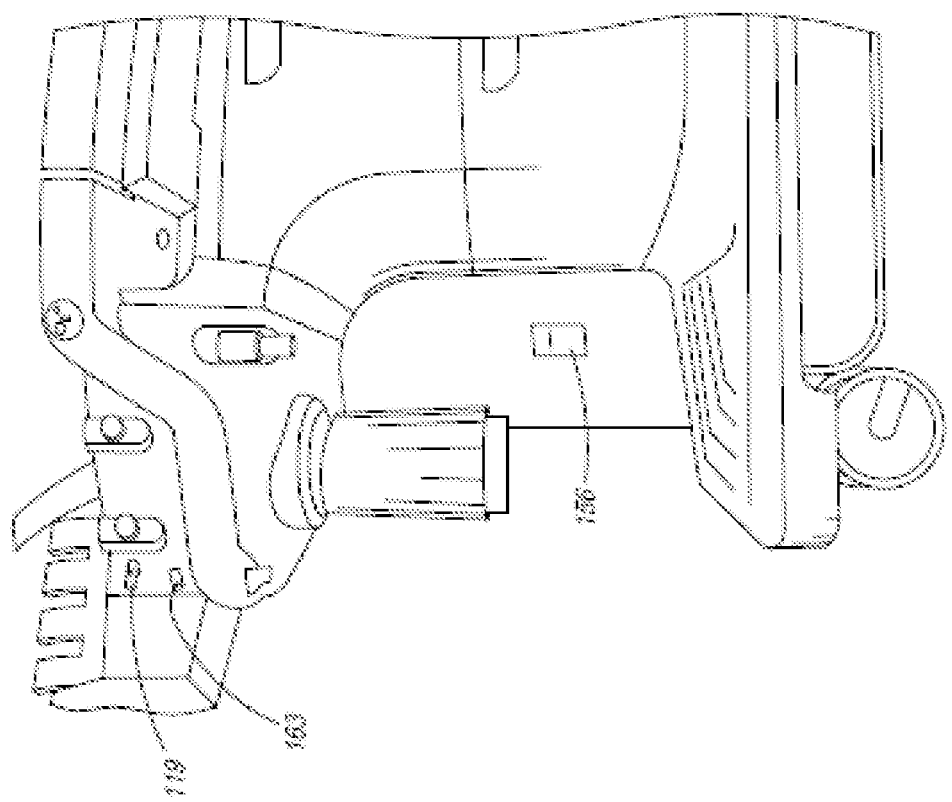
FIG. 1D is a cut-away portion of the anesthesia system of the present specification showing the ventilation monitoring connection, an exemplary interface for a respiratory gas monitor, and the anesthesia gas scavenging system.

Referring to FIGS. 1A, 1B, 1C, and 1D, CC 102 functionalities and components include a ventilator (not shown) housed in a cabinet 118; ventilator monitoring parameter connections 119; a ventilator display 109; a physiological monitor 132 (shown in FIG. 1C); at least one physiologic monitor display 111; respiratory gas analysis and connections 163 from FIG. 1D; breathing circuit (circle or circleless) and controls 150; common gas outlet (also referred to as Auxiliary Common Gas Outlet) 151; APL Valve 152, Bag 153, and Pressure Gauge 154; Bag to Vent Switch 106; Bellows 107; $CO_2$ Absorber 155; Anesthetic Gas Scavenging 156; Patient Suction Controls 157 and Catheter Storage 158; Auxiliary Oxygen Controls (also referred to as auxiliary Flow Tube) 112 and Connections 113; Fresh Gas Flow Mixing 160 and Controls 161; Vaporizers and Attachment Back Bar 108; Syringe Pump Mounts 116; Expandable Clinical Workspace 115; and Wireless Sensor Docking 117.

Referring back to both FIG. 1A and FIG. 1B, the anesthesia office (AO) 104 is pneumatically connected to CC 102 via a suction supply and anesthesia gas supplies (integrated into the system structure), which include regulated $O_2$, $N_2O$, and air. AO 104 is also pneumatically connected to a wall suction unit, an air pipeline, an $O_2$ pipeline, and an $N_2O$ pipeline. AO 104 is electrically connected to an accessory power source, AC power, and external communication means.

Anesthesia office 104 functionalities and components include user storage areas 120; computer connections and network connections area 125; cylinder attachments for an $O_2$ cylinder, $N_2O$ cylinder, and air cylinder, check valves (not shown, integrated into system) and regulation support (not shown, integrated into system); pipeline attachment (not shown, located behind system), check valves (not shown, integrated into system), and regulation (not shown, integrated into system); suction attachment (not shown, located behind system); automatic $N_2O$ shut-off with no $O_2$ (not shown, integrated into system); AC to DC power regulation (not shown, integrated); AC power isolation to accessory connections (not shown, integrated); back-up electrical power systems (not shown, integrated); and a mounting area for $3^{rd}$ party monitoring 170.

Figure 3A:
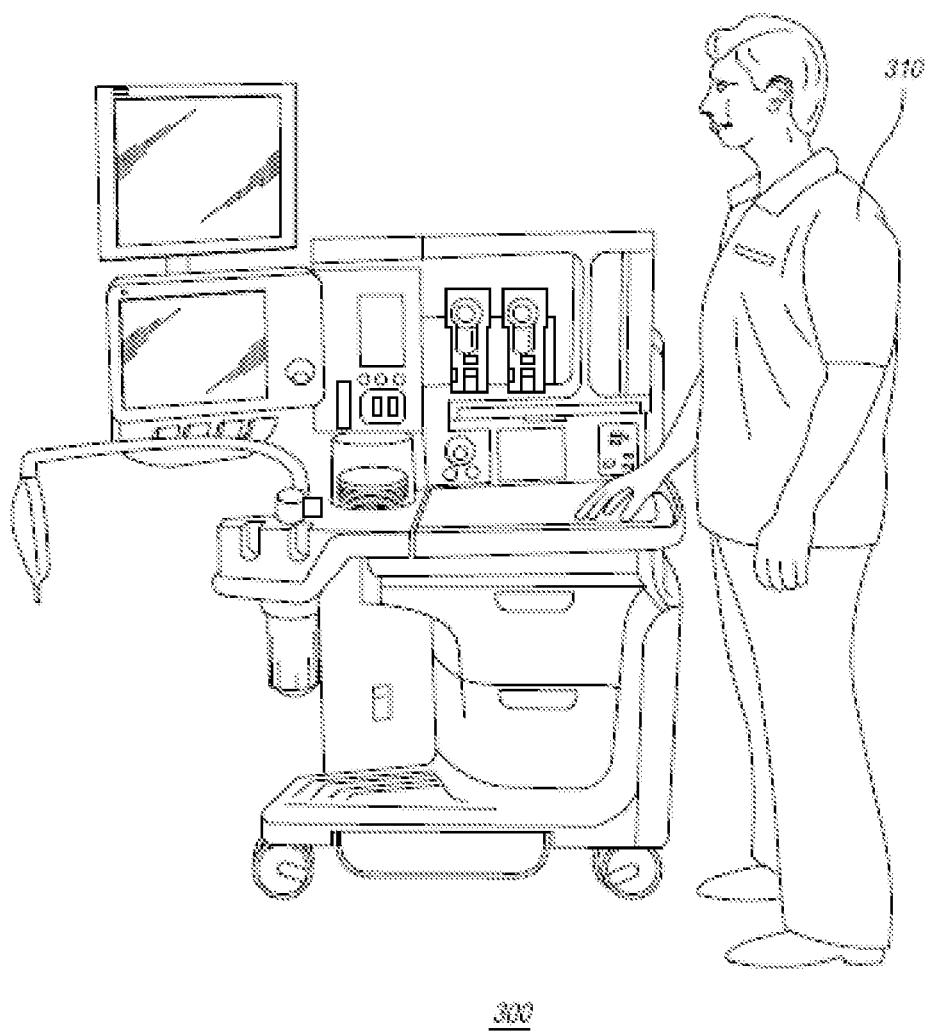
FIG. 3A is an illustration of a clinician standing at the anesthesia system of the present specification.
Figure 3B:
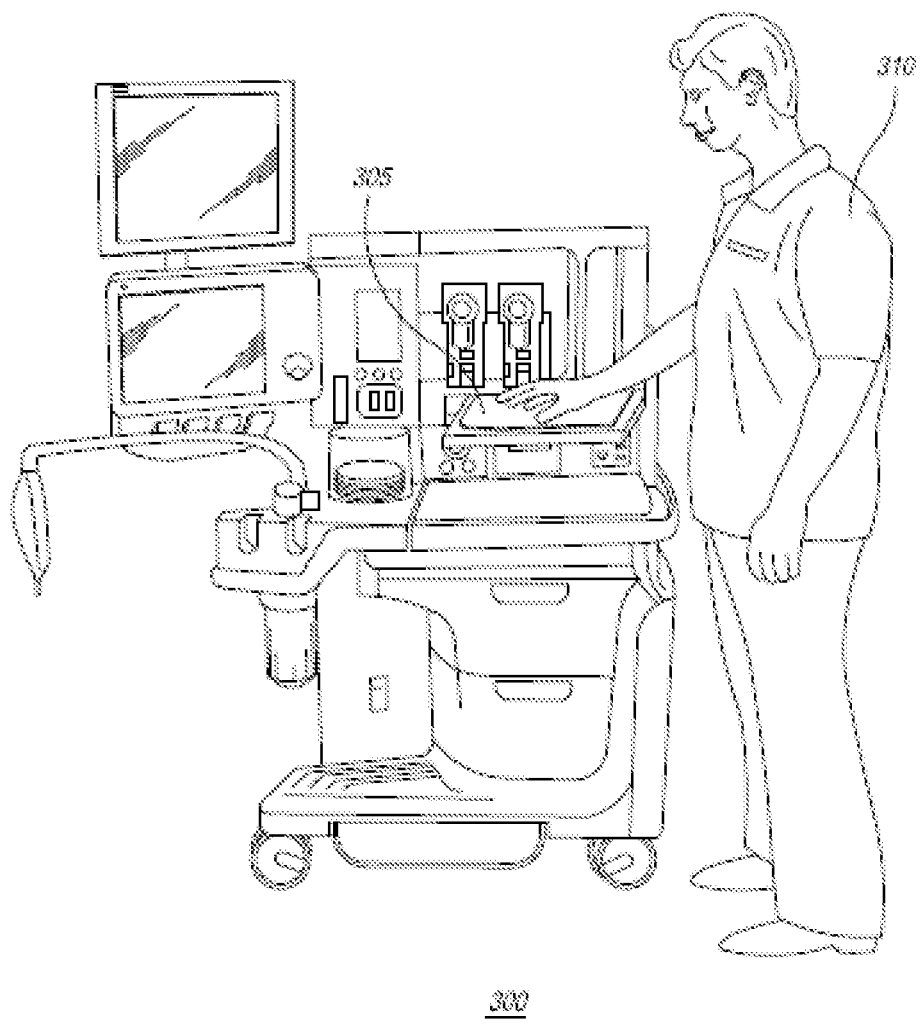
FIG. 3B is an illustration of a clinician standing at the anesthesia system of the present specification, using an upper pull-out shelf as a desk.
Figure 3C:
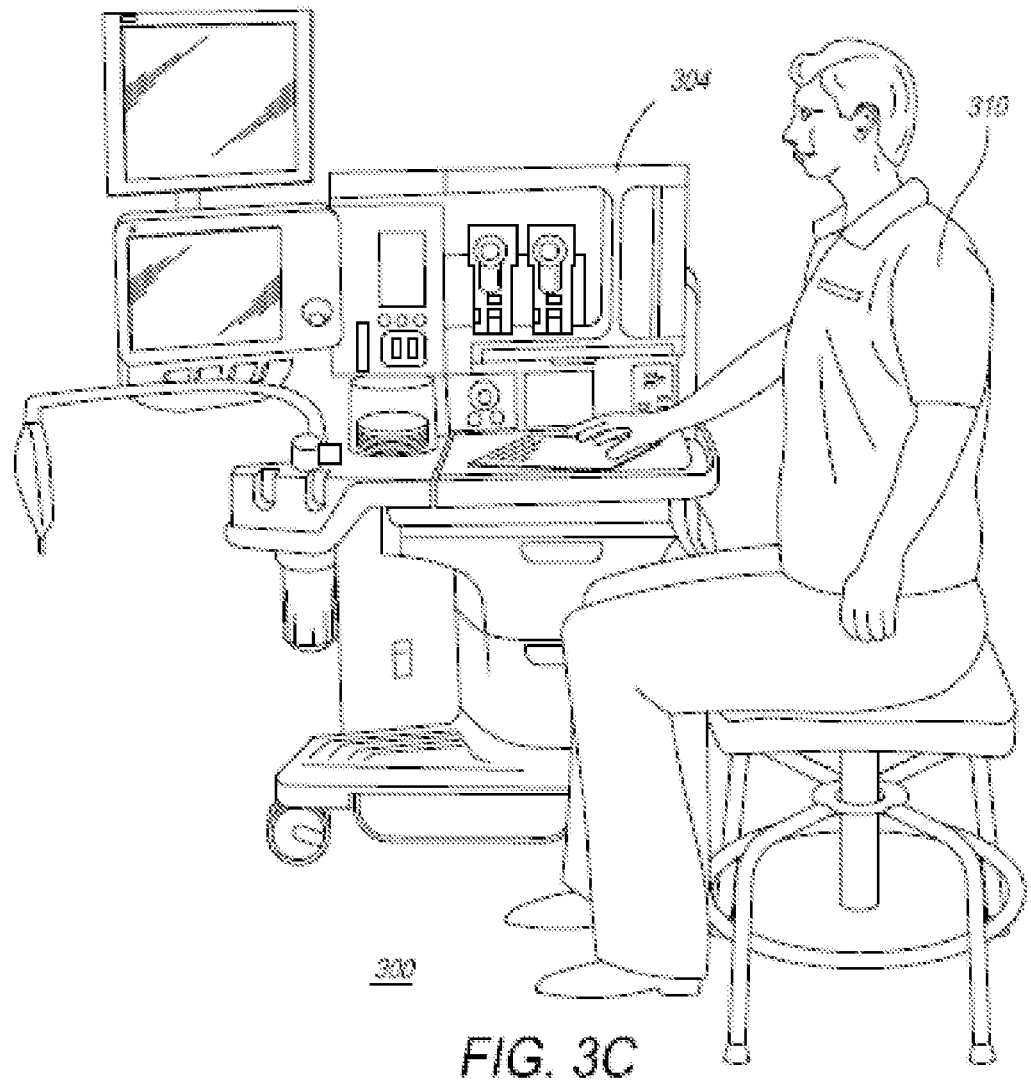
FIG. 3C is an illustration of a clinician sitting at the anesthesia system of the present specification.

In one embodiment, the AO 104 includes a support base for the anesthesia system 100 of the present specification, providing a usable space 171 for the anesthesiologist's documentation, storage 172 and personal effects 173. The AO 104 is equipped with features, such as: work surfaces 174, 175 to support both the standing and sitting behavior of the anesthesiologist (as shown in FIGS. 3A, 3B, and 3C); pull-out trays 176 that allow for a computer keyboard; personal electrical equipment connectors 178 on the front of the AO; side door storage 177, which, when opened contains easy to clean pockets and cubbies for storage of office items like pens, notes, clipboards, files, etc.; foot rest with angled front to allow knee room 179; a handle based caster unlock feature 180; and, lighting 181 of work areas for operation in low light conditions.

In one embodiment, the AO 104 houses all pneumatic supplies, AC electrical support and data communication connections for the anesthesia system, and supplies the CC 102 with the necessary inputs for its function. In one embodiment, the AO 104 may be considered the "hub" of the anesthesia system 100 and provides the functions of: AC to DC power conversion for the anesthesia system components, including the CC; AC power isolation for accessory outlets; backup power supply (i.e. battery, UPS); pneumatic protection of pipeline sources (i.e. filters, check valves); cylinder attachment and mounting locations; primary regulation of cylinder supplies with automatic pipeline loss cross-over; a system status screen; and, hospital network data connections.

FIG. 1C illustrates the backside of one embodiment of the anesthesia system of the present specification, showing a connections area 130 where electrical connections are made to monitoring equipment. Further, as described above, FIG. 1C also shows physiological monitor 132.

FIG. 1D illustrates ventilation monitoring parameter connections area 119 in greater detail. Further, FIG. 1D also shows anesthesia gas scavenging system 156 in enlarged detail. And finally, the figure also shows a sample attachment interface 163 for a respiratory gas monitor.

Referring back to FIG. 1A, several types of movements are available to position the CC 102 relative to the AO 104 in the anesthesia system of the present specification. First, a rotational movement can be used to rotate the breathing circuit 150 (or the CC 102) away from or towards AO 104 at junction 197, in incremental angles up to 45 degrees, such that CC 102 is in a first extended position relative to AO 104.

In one embodiment, the CC 102 is moved on a sliding track (not shown), located on the base support on the AO 104 out from its locked position (i.e. fully integrated position) on the AO 104 into a fully extended position. In one embodiment, a portion of the track is preferably positioned at an oblique angle, which is, in one embodiment 24 degrees, to the front face and wheel base of the AO 104, allowing the movement of the CC 102 and its connection ports to move forward and left from its fully integrated position.

Second, a translational movement at junction 196 having a range of 0 to 14.5 inches is available to compress and collapse the CC 102 back into AO 104 or extend CC 102 away from AO 104. In addition, the translational movement at junction 196 also results in translational movement at junction 197. Thus, once translated away from AO 104, CC 102 is in a second extended position relative to AO 104.

In addition, the aforementioned rotational and translational movements can be combined, such that CC 102 is in a third extended position relative to AO 104.

It should be evident to those of ordinary skill in the art, that although only a few positions are shown, CC 102 can have a plurality of positions relative to the AO 104. In one embodiment, the workspace point (shown as 297 in FIG. 2A and described in greater detail below) can be accessed by rotating, translating, or both rotating and translating CC 102 away from AO 104.

Figure 2A:
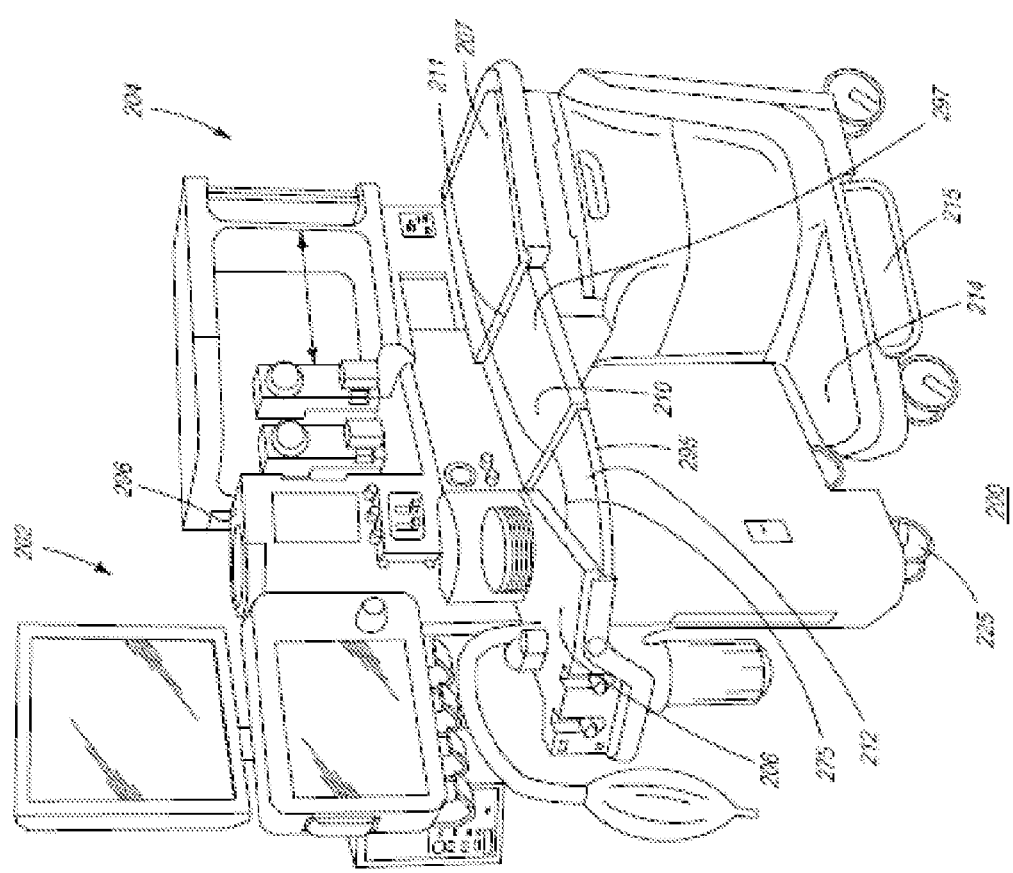
FIG. 2A is an illustration of the anesthesia system of the present specification in a first configuration, fully rotated and telescoped.

FIG. 2A illustrates the CC 202 telescoped outwards and away from the AO 204, creating a clinical workspace area for the clinician's use. By way of comparison, and referring back to FIG. 1A, the anesthesia system 100 of the present specification shown in FIG. 1A is in a fully collapsed position. Referring back to the telescoped system 200 in FIG. 2A, the gap created as the CC 202 moves away from the AO 204 expands and exposes work surface 210 such that it extends out from areas under the main AO work surface 207. These surfaces 210 have close tolerance or flexible seals at their interfaces 211 to avoid having materials sitting on the surfaces being jammed into the gap between surfaces. In an embodiment, the movement of the CC 202 is indexed in order to create a rigid positioning means for the CC 202 relative to the AO 204. In other embodiments a plurality of other locking means not involving indexing could also be utilized, in order to obtain a locking mechanism rigid enough to prevent inadvertent movement of the CC 202 relative to the AO 204, and the dislodging of articles on the expanded work surface 210.

In various embodiments, it is essential to prevent debris, such as waste material, pens, needles, syringes, etc., from being drawn into interior, non-user accessible portions of the anesthesia system. If such debris is allowed to slide under the main AO 204 work surface 207 or work surface 210 of CC 202, it could cause a refraction or extension jam or otherwise clutter and obstruct the internal portions of the anesthesia system. Also, it is essential to ensure that portions of the system that move into the interior during retraction/collapse, such as work surface 210 that moves under the main AO 204 work surface 207 when retracted, do not cause internal microbial contamination that could be a source of recontamination of extendible work surface 210, even if the surfaces have been previously cleaned.

As described above, the surfaces of the anesthesia system which move over or under each other, such as surfaces 210 and 207, have close tolerance or flexible seals at their interfaces 211 to avoid having materials sitting on the surfaces being jammed into the gap or stuck between surfaces. In one embodiment, the flexible seals employed are "bulb seals" such as those well-known to those of ordinary skill in the art. After application and when surface 210 is refracted or collapsed into the system, the bulb type seals flex to completely fill the gap between the top of surface 210 and the bottom of surface 207.

Figure 2B:
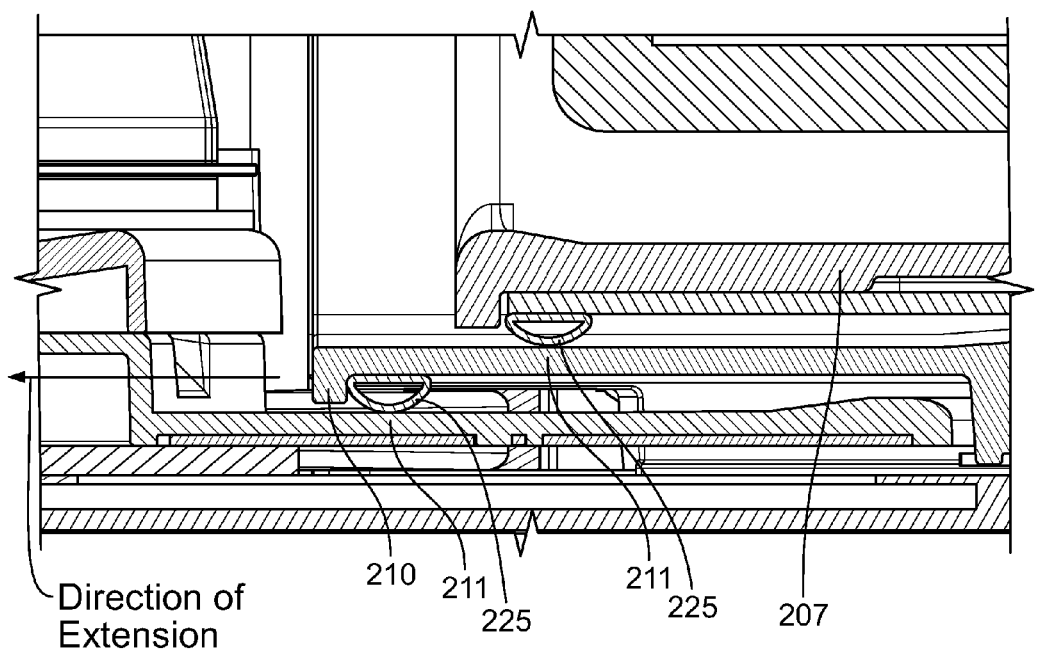
FIG. 2B illustrates a bulb type seal applied to the anesthesia system, in accordance with an embodiment of the present specification.

FIG. 2B illustrates a bulb type seal 225 applied to the anesthesia system of the present specification. As illustrated in FIG. 2B, at least one bulb type seal 225 and preferably a plurality of bulb type seals 225 are provided at interfaces 211 of the surfaces 207 and 210. In various embodiments, other seals commonly known in the art, such as wiper type seals or flexible foam, may be used in the anesthesia system of the present specification.

In an embodiment, the employed seals comprise antimicrobial treatments to ensure that surface 210 is free of microbial contamination as it slides by the flexible seal at interface 211. Such antimicrobial treatments are commonly known in the art. For example, antimicrobial silver ion surface treatments known in the art may be used with the present specification. In another embodiment, the employed seal may be of a foam type that is immersed in an antimicrobial solution before application. Various other antimicrobial seals commonly known in the art may be employed in the anesthesia system.

In order to further reduce the chance of cross-contamination, in an embodiment, the top surface of work surface 210 and the top and bottom surfaces of AO work surface 207, are coated with antimicrobial treatments such as silver ion. In yet another embodiment, the antimicrobial treatment are in the form of treated surface decals which are applied on the top surface of work surface 210 and the top and bottom surfaces of AO work surface 207. A decal (or transfer) is a plastic, cloth, paper or ceramic substrate that can be moved to another surface upon contact, usually with the aid of heat or water. In an embodiment, surface decals are coated with antimicrobial treatments by using any suitable surface coating methods known in the art, before applying the decals on one or more surfaces of the anesthesia system. The antimicrobial treatment coated surface decals may be periodically changed by users of the anesthesia system. Further, as would be apparent to persons of ordinary skill in the art, various other commercially available antimicrobial treatments and coatings may be used for the purposes described above.

In an alternate embodiment, the top surface of work surface 210 and the top and bottom surfaces of AO work surface 207 are rendered permanently sterile by using commercially available antimicrobial treatments. For example, a film-based solution having an intrinsic micro-geometry which, when applied on a surface makes the surface resistant to microbe growth, may also be employed.

Figure 2C:
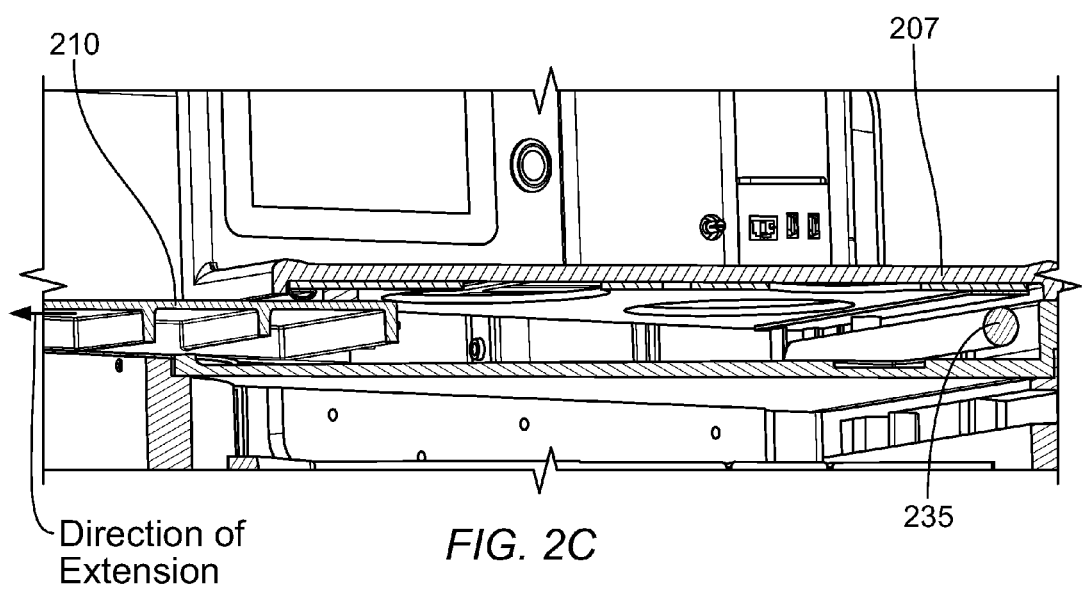
FIG. 2C illustrates an ultraviolet (UV) light source employed in the anesthesia system, in accordance with an embodiment of the present specification.

In an alternate embodiment, in order to prevent contamination, the anesthesia system is further equipped with at least one Ultra-Violet (UV) light source, which is known in the art to have an anti-microbial effect. For example, UV light sources designed to disinfect surfaces, including those used in the medical industry, may be employed. As would be apparent to persons of ordinary skill in the art, any other commonly available UV light sources suitable for the mentioned application may be employed to disinfect the anesthesia system. In an embodiment, a UV light source is arranged at one or more positions in the interior of the anesthesia system and is activated when the anesthesia system's work surfaces 210 are extended or retracted. In another embodiment, the employed UV light source is activated either continuously or periodically for predefined intervals of time. FIG. 2C illustrates a UV light source 235 employed in the anesthesia system, in accordance with an embodiment of the present specification. As illustrated, a UV light source 235 is placed below the main AO work surface 207 for illuminating internal surfaces of the anesthesia system when the CC is extended and the work surface 210 is exposed. The UV light source 235 illuminates and disinfects, among other parts, the gap created under the work surface 207 when the surface 210 extends out.

In another embodiment, a low cost system for disinfecting the anesthesia system, which may be applied to multiple systems employed in a hospital environment, is provided. In the embodiment, instead of having a UV source built into the anesthesia system, a UV light "wand" is provided which is introduced into the interior of the anesthesia (and other) system(s) periodically for disinfecting the system(s). The "wand" is a thin, UV light source element that, in an embodiment, is provided as a specialized service tool for the anesthesia system. The wand may be introduced into interiors of the anesthesia system on a routine basis by a user for the purposes of disinfecting the interiors of the system. In an embodiment, the anesthesia system is provided with access holes for inserting the UV light wand. In another embodiment, one or more pre-determined covers of the anesthesia system may be removed in order to introduce the UV light wand to the interiors of the system.

In yet another embodiment, the interior of the anesthesia system is periodically cleaned by using an antimicrobial pad, or a general purpose pad soaked in antimicrobial cleanser, for disinfection. In this embodiment, an antimicrobial pad is temporarily attached to the work surface 210 and is introduced into the interiors of the anesthesia system under the main AO work surface 207 as the system is refracted. The antimicrobial pad is flexible and rubs on the bottom surface of AO work surface 207 as the work surface 210 is retracted. In an embodiment, the antimicrobial pad is made of flexible cotton material that compresses downward as it is moved into the anesthesia system and provides a "wipe" action as it is moved laterally across the interior surfaces of the system. In an embodiment, the antimicrobial pad is soaked with isopropyl alcohol or any other available disinfectant agent. The antimicrobial pad can provide multiple wipe actions, to ensure anti-microbial treatment, via successive extensions and retractions of the anesthesia system.

Figure 2D:
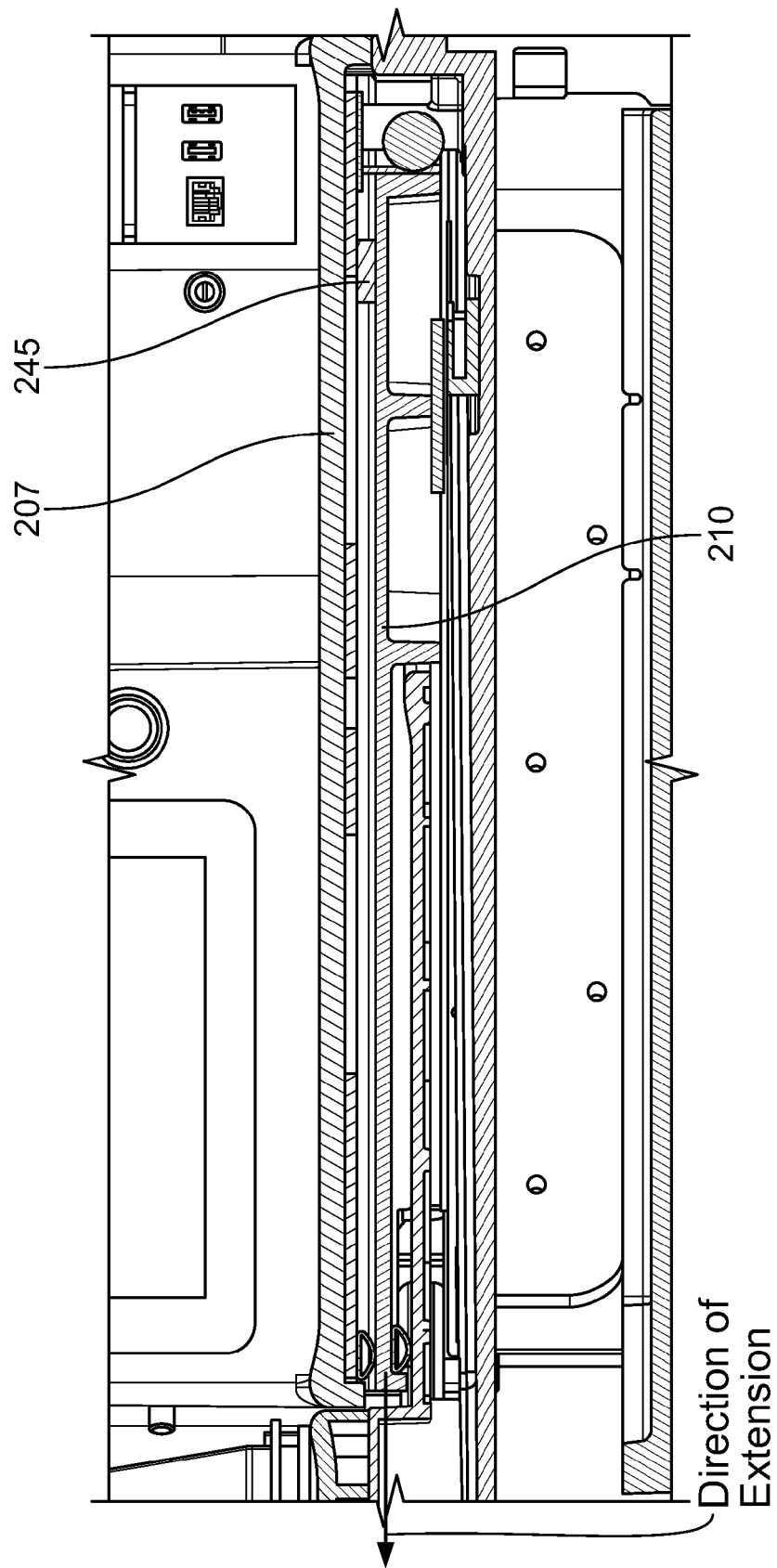
FIG. 2D illustrates an antimicrobial pad permanently attached to the anesthesia system, in accordance with an embodiment of the present specification.

In an alternate embodiment, the pad is permanently installed on an edge of work surface 210 and remains under the AO work surface 207, and is periodically conditioned with commercially available anti-microbial solutions via a wicking action at interface 211. FIG. 2D illustrates an antimicrobial pad permanently attached to the anesthesia system, in accordance with an embodiment of the present specification. As illustrated, an antimicrobial pad 245 is attached to the surface 210 such that the pad 245 wipes an interior surface of the AO main surface 207 when the CC is extended. In an embodiment, users or biomedical service personnel may periodically pour isopropyl alcohol or any other suitable disinfectant solution onto the pad 245 in order to refill the pad 245 and disinfect the internal surfaces of the anesthesia system.

Further, as would be apparent to persons of ordinary skill in the art, alternate embodiments of commercially available surface and material treatments may be used within the spirit of this specification as means to limit microbial growth on the exposed and interior surfaces of the anesthesia system.

In yet another embodiment, the CC's 202 movement relative to the AO 204 is motorized and is actuated electronically by user controls on the anesthesia system 200. In one embodiment, a single user actuation results in a preprogrammed motorized movement of the CC 202 relative to the AO 204. In an embodiment, if the user-actuated motorized movement of the CC 202 encounters an obstruction, the movement of the CC 202 is automatically stopped. In one embodiment, the change in electric current drawn by the movement motor is utilized to detect obstruction. At the same time, in additional or alternative embodiments, obstruction signals in the form of audio alarm and/or visual alarms, such as a flashing light, are used to indicate obstruction and the resulting stalled movement of the CC 202. In one embodiment, existing lights used for illuminating various elements of the anesthesia system are utilized as alarm flashing lights. In one embodiment, the existing lights comprise those in the overhead area near point 196 in FIG. 1A focusing on the vaporizers and/or the work surface that is proximal to point 197 of FIG. 1A.

Further, FIG. 2A illustrates at least one floor contact point 225 at the bottom of the CC 202. As the CC 202 moves a considerable distance away from the AO 204 and the main four wheel trolley base 214, it is not practical to cantilever the CC 202 part of the system from the AO 204, due to tip and strength concerns. Consequently, the CC 202 employs its own ground contact point 225 to allow for load-bearing, which may include one or more users leaning on the CC 202, to be transferred directly to the floor rather than through the AO 204 trolley frame.

In one embodiment, the at least one contact point 225 is capable of providing equal horizontal friction in a full 360 degree pattern and is, but is not limited to, a rotating trackball type or caster wheel type (having multiple rollers) of moveable load transfer mechanism that enables both inline and side to side movement. The use of a moveable contact ensures that the CC 202 and the anesthesia system 200 can be moved or relocated in its entirety and quickly, even in an "open" or fully extended configuration. In an embodiment, the anesthesia system 200 is locked using a central brake system that locks either two or four of the wheels under the AO 204. This central brake system, is, in one embodiment, controlled via a foot pedal 215, known to those of ordinary skill in the art, or may be controlled via a hand lever positioned in one or more locations on the anesthesia system's movement handles, which is described in greater detail below. The hand lever provides a more direct lock/unlock arrangement.

In one embodiment, the at least one contact point 225 is disengaged from the floor when the CC 202 is moved into its base, locking position against the AO 204, leaving just the original, standard four casters in contact with the floor. Alternatively, the contact between the CC 202 and the floor could be maintained even in the locked position. In one embodiment, the contact point 225 is configured with the appropriate geometry to move obstructions on the floor as the contact point 225 is extended, including, but not limited to elements such as a cover or flexible spring that comes in close proximity to the floor and thereby pushes or lifts obstructions prior to these obstructions getting close to the contact points 225 on the floor.

Thus, in various embodiments, the floor contact point and movement mechanisms of the CC allow for load bearing to the workspace area created by its movement away from the AO, with no risk of tipping or damage. The additional usable workspace exposed by the separation of the CC from the AO, described below, may be used by the clinician for their supplies and tools, solving the issue of "limited workspace" on smaller machines. Subliminally, this also allows the anesthesiologist to establish "their space" in what can be a very crowded OR environment containing many people and varieties of equipment. This space allows them to separate their clinical responsibilities and workflow from those that are more documentation and office related.

FIG. 2A illustrates an angular articulation of the breathing circuit connection area 206 away from the AO 204. The breathing circuit connection area 206 is both telescoped and rotated outwards, and a "cockpit" area is generated for the clinician, with the AO 204 on the right hand side and the CC 202 sweeping to the left. In this configuration, the AO 204 can advantageously be positioned well away from the patient and out of the clinical field, but the CC 202, with all the clinical controls, can be positioned in close proximity to the patient. It is observed that the additional angular rotation of the breathing circuit area 206 also exposes additional workspace 212 for the clinician.

In various embodiments of the present specification, the telescopic motion and angular rotation movements of the anesthesia system and its components can be deployed in a variety of configurations allowing the CC 202 to be positioned at a plurality of locations relative to the AO 204. As mentioned above with respect to FIG. 1A, three types of movements are available to position the CC 202 relative to the AO 204 in the anesthesia system of the present specification.

Figure 2E:
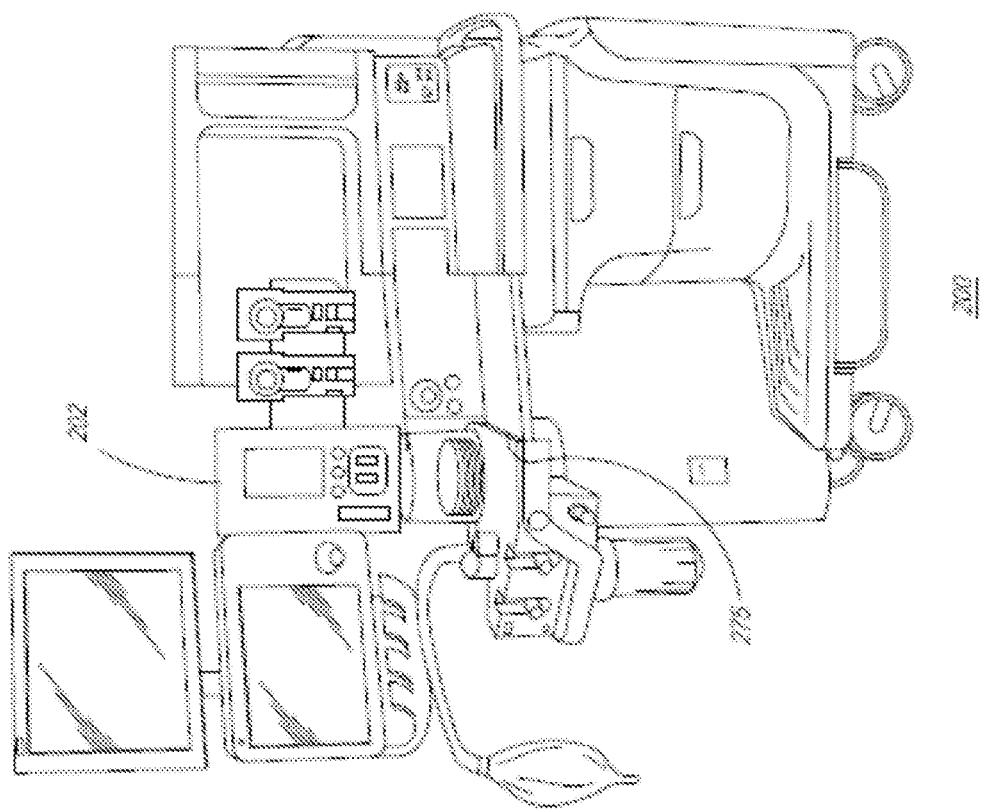
FIG. 2E depicts the anesthesia system of the present specification in a second configuration, fully telescoped, but not rotated.

In one embodiment, a rotational movement can be used to rotate CC 202 away from or towards AO 204 at junction 295, in incremental angles. FIGS. 2A and 2E depict the anesthesia system of the present specification in various configurations. FIG. 2A begins with the anesthesia system 200 of the present specification in a fully extended and rotationally open position, with the rotational angle 275 in a fully open position of 45 degrees. Angle 275 is rotated from a maximum of 45 degrees to a minimum of zero degrees, in increments, until the CC portion 202 of the anesthesia system 200 is in a rotationally closed or collapsed position and is thus rotationally flush with the system, with angle 275 at zero degrees, as shown in FIG. 2E. In one embodiment, the rotational increments are indexed at preset angles, such as at every 5 degrees, or controlled continuously using a friction bearing to be any selected angle. In a preferred embodiment, there is a detent at the zero degree angle (that is, closed or collapsed position of system 200) so that when the system 200 is rotated fully closed it "clicks" shut in a positive manner.

Figure 2F:
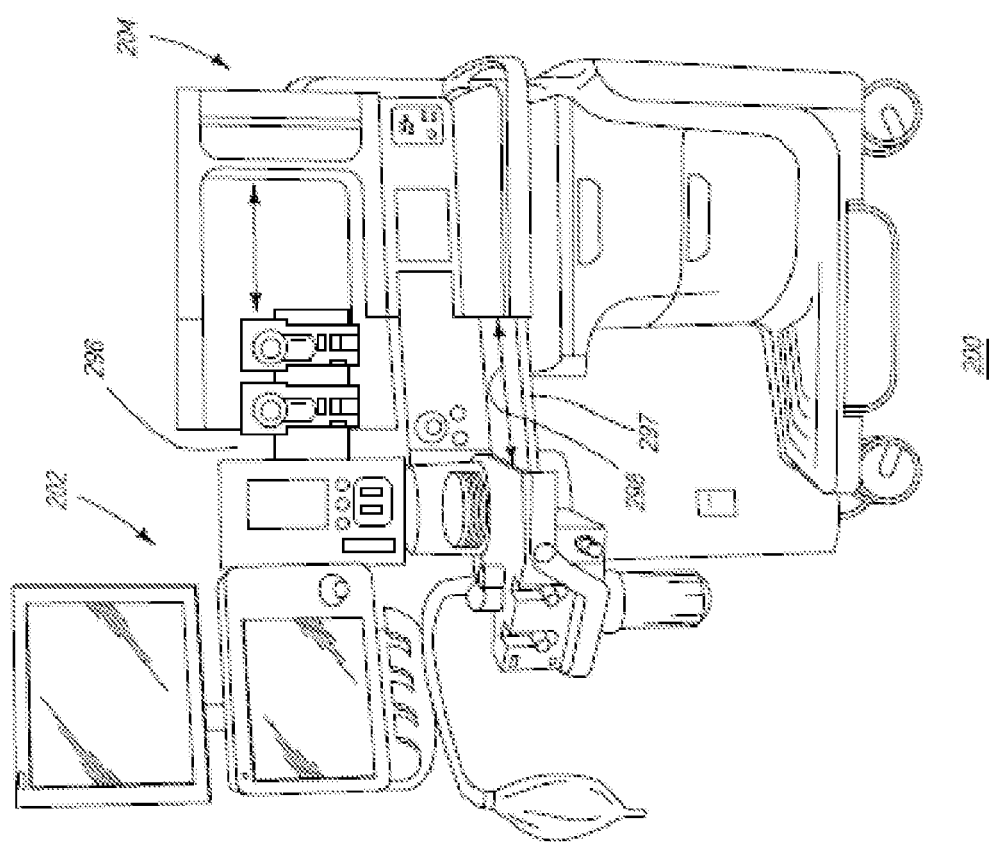
FIG. 2F depicts the movement of anesthesia system of the present specification in a third configuration, as the clinical center (CC) is compressed and collapsed back into the anesthesia office (AO) and thus in a partially telescoped position.
Figure 2G:
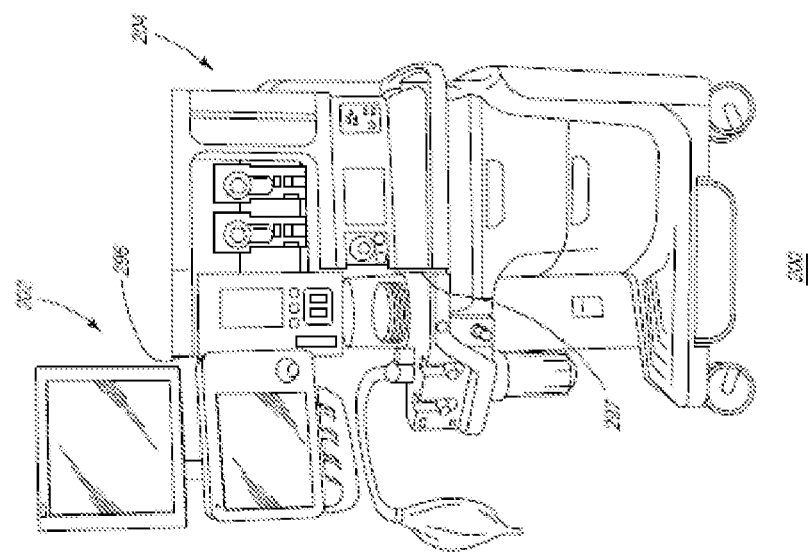
FIG. 2G depicts the movement of anesthesia system of the present specification in a fourth configuration, as the clinical center (CC) is compressed and collapsed back into the anesthesia office (AO) and thus in a fully collapsed position.

In another embodiment, a translational movement at junction 296 is available to telescopically or linearly compress and collapse the CC 202 back into AO 204 or extend CC 202 away from AO 204. FIGS. 2F and 2G depict the range of translational movement of the system 200 at junction 296 as the CC 202 is compressed and collapsed back into the AO 204. In one embodiment, the translational movement range available to compress and collapse CC 202 back into the AO 204 is 14.5 inches. It should be noted herein that a translational movement at point 296 also results in a translational movement 298 at junction 297.

Figure 2H:
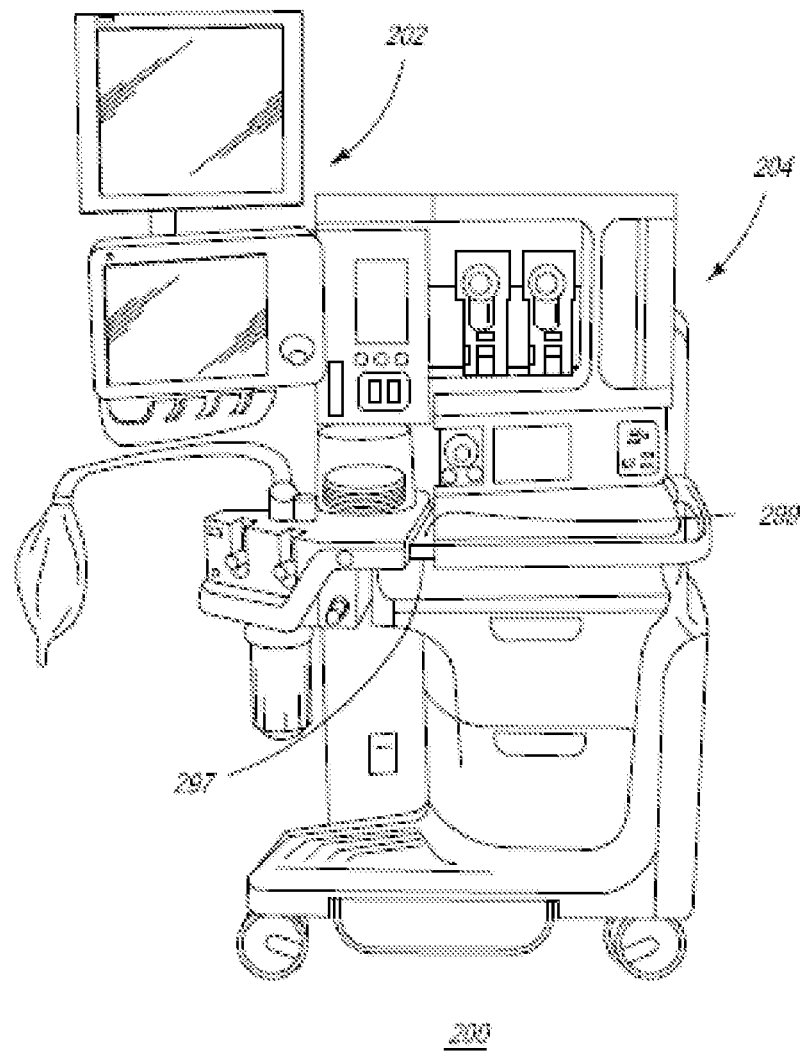
FIG. 2H depicts the incremental angular motion of the clinical center (CC) as it is partially rotated away from the anesthesia office (AO), in a fifth configuration.
Figure 2I:
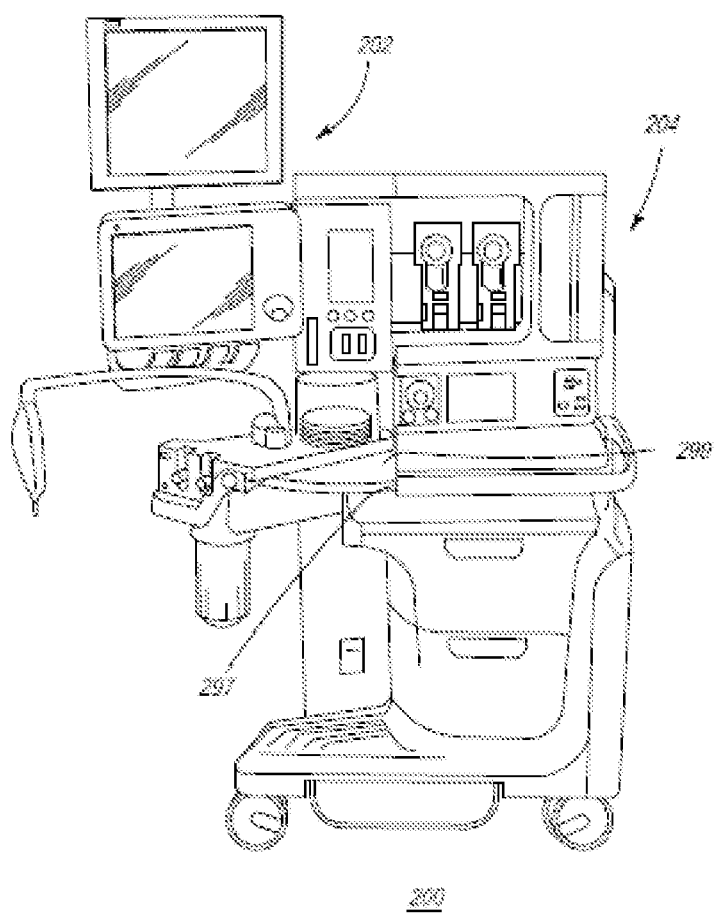
FIG. 2I depicts the incremental angular motion of the clinical center (CC) as it is fully rotated away from the anesthesia office (AO), in a sixth configuration.

It should be appreciated by those of ordinary skill in the art that the rotational and translational movements can be combined to have a plurality of positions of the CC 202 relative to the AO 204. Thus, in one embodiment, a workspace 299 can be accessed by either rotating or translating CC 202 away from AO 204 at junction 297, as shown in FIGS. 2H and 2I. FIG. 2H depicts the angular motion of the CC 202 as it is moved in at least one increment, away from AO 204, at an angle of, for example, 5 degrees. FIG. 2I depicts the angular motion of the CC 202 as it is fully rotated away from AO 204 at an angle of 45 degrees, in accordance with one embodiment, but when the anesthesia system 200 has not been expanded or telescoped for extra workspace. In addition, the CC may be telescoped out from the AO (translational motion), creating or exposing additional workspace, as described above.

Hence, in various embodiments the CC of the anesthesia system of the present specification may be unilaterally moved towards a patient and away from the main trolley apparatus containing the AO, cylinders and pipeline gas connections. Since the CC carries all clinical controls and visual displays necessary for the clinician's direct treatment of the patient, these areas remain within easy reach and sight of the clinician addressing the patient. The resulting system architecture eliminates the need for external connections to the CC and requires only "clean" pneumatic pipeline and power supplies to be provided. In one embodiment, the CC itself could be utilized as a small anesthesia system, utilizing a longer umbilical to electrical and pneumatic sources.

In one embodiment, the anesthesia system includes breathing circuit attachment ports that can be swiveled rotationally and horizontally to enhance breathing circuit tube flexibility for routing in cluttered and physically constrained medical environments. As mentioned above, physical constraints in the operating room (OR), due to, but not limited to, surgery type, OR layout, equipment in use, number of personnel required in room, location of personnel, among other reasons, add demands to the positioning and structure of the anesthesia system, particularly with regard to the breathing tube port attachments. Breathing tube port attachments often limit the movement of a system, and if twisted or torqued in the wrong direction, there is a risk of disconnect and kinking or twisting of the breathing tube.

FIG. 2J is an illustration of one embodiment of at least one swiveling breathing circuit attachment port 232 in a first, default configuration, having a breathing tube connection outlet positioned perpendicular to the front surface 240 of the clinical center (CC).

FIG. 2K is an expanded, front view of the swiveling breathing circuit attachment port of the present invention, shown in FIG. 2J.

FIG. 2L is an expanded, back view of the swiveling breathing circuit attachment port of the present invention, shown in FIGS. 2J and 2K.

Referring simultaneously to FIGS. 2J, 2K, and 2L, breathing circuit attachment port 232 comprises a rotating body having a rotating cap 234 that is embedded within a planar surface 233 on a bottom portion 202b of the clinical center (CC) 202 and a port housing 236 extending downward from the rotating cap 234, where the port housing 236 is, in one embodiment, cylindrical in shape and defines a space for receiving a gas. The rotating body is inset into the CC 102 so that rotating cap 234 is flush with the top planar surface 233 and therefore, in the same plane as the top planar surface 233 of CC 202, while the remainder of the rotating body is positioned beneath the top planar surface 233 of CC 202. The entire rotating body breathing circuit attachment port 232 moves with movement of any portion of the port 232.

Further, breathing circuit attachment port 232 comprises at least one limb, which is inspiratory, expiratory, or a combination thereof. In one embodiment, the at least one limb on breathing circuit attachment port 232 is an inlet connected to an anesthesia gas supply line for receiving gas and an outlet for connecting a proximal end of a breathing tube with the distal end of the breathing tube connected to a patient. In one embodiment, the inlet 239 (shown in FIG. 2L) and outlet 238 (shown in FIG. 2K) are positioned perpendicular to an exterior portion of the port housing 236 such that they are directly opposite one another (positioned 180 degrees from one another) and such that the outlet 238 is positioned perpendicular to the exterior, vertical portion of the port housing 236 such that it protrudes from the front surface 240 of the system while the inlet 239 remains in the interior portion of the system.

In another optional embodiment, the inlet and outlet are positioned on the port housing 236 such that the inlet is directly underneath and connected to an exterior, bottom portion 237 of the port housing 236 and that the outlet is positioned perpendicular to the exterior, vertical portion of the port housing 236 such that it protrudes from the front surface 240 of the system.

It should be noted herein that the inlet and outlet may be positioned anywhere on the port housing 236 such that they do not interfere with tubing connections or the swiveling movement of the breathing circuit attachment port 232.

In one embodiment, the breathing circuit attachment port 232 is rotated using a swiveling mechanism. In one embodiment, the ports are rotated manually and are friction fit. In one embodiment, the ports are spring-controlled and bounce back to default position if not swiveled in an angular increment. In one embodiment, the cylindrical port housing is radially sealed. In one embodiment, conventional O-Rings are used to radially seal the cylindrical port housing. In one embodiment, the radial seal enables the breathing circuit attachment port to rotate with the cylindrical housing.

In one embodiment, the swiveling breathing circuit attachment ports 232 can be rotated in a range of −15 degrees to +15 degrees about an axis 243 normal to (or perpendicular to) the planar surface 233 of the bottom portion 202b and extending through a center point of the port 232, allowing full clearance for breathing circuit filters that are typically used in the anesthesia application. In one embodiment, filters may optionally be used on both inspiratory and expiratory ports. In some cases, available filters may be large, when compared to actual port size. The movement of the ports in opposite angular directions, thus yielding a bidirectional range of motion allows for the use of larger filters.

It should be noted herein that any range of angles may be envisioned for the swiveling breathing circuit ports of the present invention. The range of −15 degrees to +15 degrees is selected to allow the patient circuit tubing to exit from the breathing circuit while avoiding tubing trapment or pinch issues. In some cases, use of larger angles may cause filters to be jammed against the front of the breathing circuit as the ports are rotated, depending upon filter size. As shown in and referring back to FIG. 2J, in a default configuration, swiveling breathing circuit attachment ports 232 are positioned such that the breathing tube connection outlet 238 is perpendicular to the front face 240 of CC 202.

FIG. 2M is an illustration depicting one embodiment of swiveling breathing circuit attachment ports 232 in a second configuration, having a breathing tube connection outlet 238 rotated toward the right side of the clinical center (CC) 202. Thus, in one embodiment, the breathing circuit attachment ports are rotated 15 degrees toward the right side of the CC 202 about a vertical axis through the center of breathing circuit port 232.

Figure 2N:
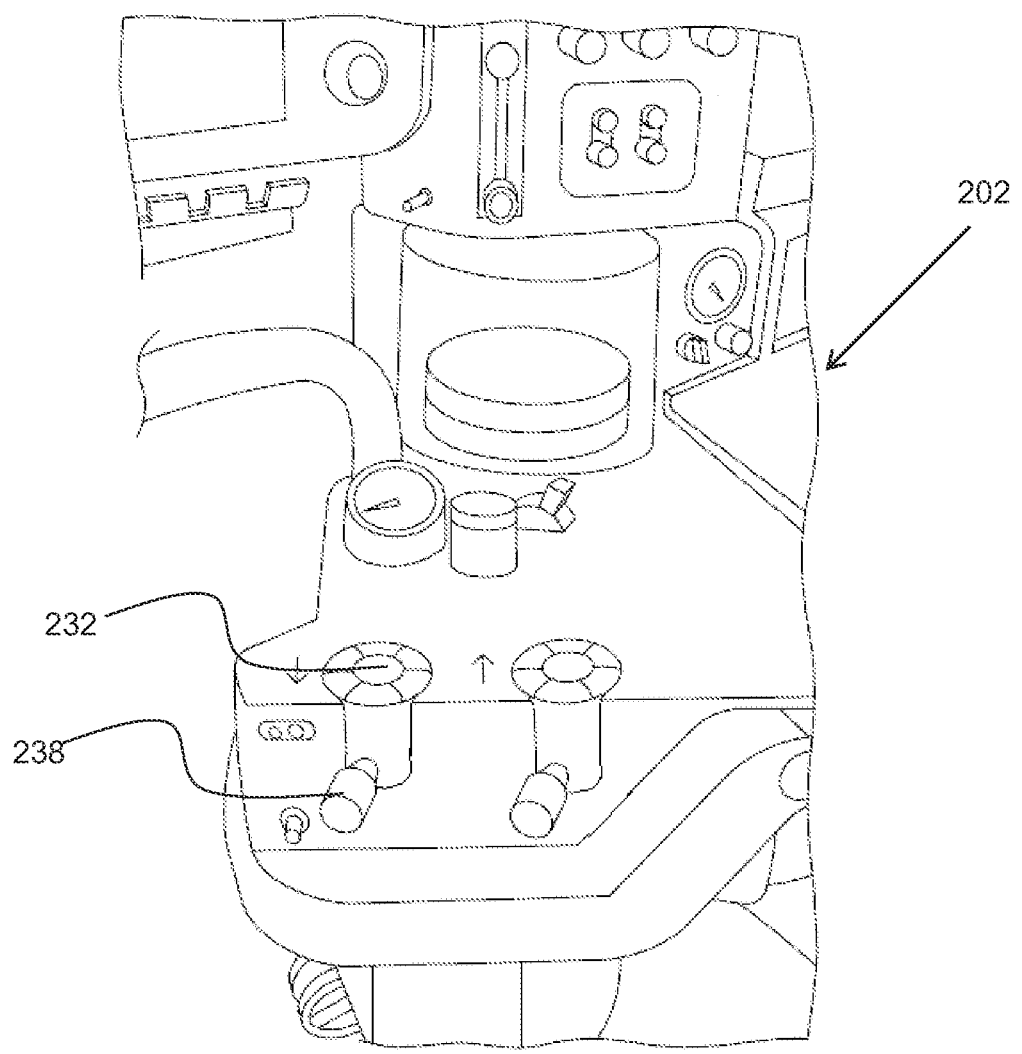
FIG. 2N is an illustration depicting one embodiment of at least one swiveling breathing circuit attachment ports in a third configuration, having a breathing tube connection outlet rotated fully toward the left side of the clinical center (CC)

FIG. 2N is an illustration depicting one embodiment of swiveling breathing circuit attachment ports 232 in a third configuration, having a breathing tube connection outlet 238 rotated toward the left side of the clinical center (CC) 202. Thus, in one embodiment, the breathing circuit attachment ports are rotated 15 degrees toward the left side of the CC 202 about a vertical axis through the center of breathing circuit port 232.

In various embodiments, the swiveling breathing circuit attachment ports 232 can be rotated independently from each other to any point within their range of motion. In one embodiment, the swiveling breathing circuit attachment ports 232 are positioned at a minimum distance from one another to avoid interference on rotation. In one embodiment, the minimum distance is approximately 120 mm.

In one embodiment, the ports rotate in angular increments. In one embodiment, the port rotates in 1 degree increments. In one embodiment, the outer diameter of the port housing 36 ranges from 17-27 mm. In one embodiment, the port housing has an external diameter of 22 mm. In one embodiment, the inner diameter of the port housing 236 is in the range of 10-20 mm. In one embodiment, the port housing 236 has an internal diameter of 15 mm.

In one embodiment, the breathing circuit attachment ports 232 are removable for cleaning. In one embodiment, the top surface or rotating cap 234 of each breathing circuit attachment port is translucent. In one embodiment, the breathing circuit attachment port comprises breathing circuit check valves, which can be observed through the translucent housing of the breathing circuit attachment port. In another attachment, the top surface or rotating cap 234 of the breathing circuit attachment port is translucent and further includes information projection lighting to indicate when flow is moving through the port so that the action of the breathing circuit check valves, described in greater detail below, can be observed by the user.

FIG. 3A is an illustration of a clinician 310 standing near the anesthesia system 300 of the present specification. Thus, in this illustration, one can see the relative dimensions of the system 300 with respect to the clinician 310. FIG. 3B illustrates the clinician 310 using an expandable pull-out shelf 305 located on the system 300. FIG. 3C illustrates the clinician 310 sitting at the anesthesia office (AO) portion 304 of the system 300, when it is in a fully collapsed configuration.

Figure 4A:
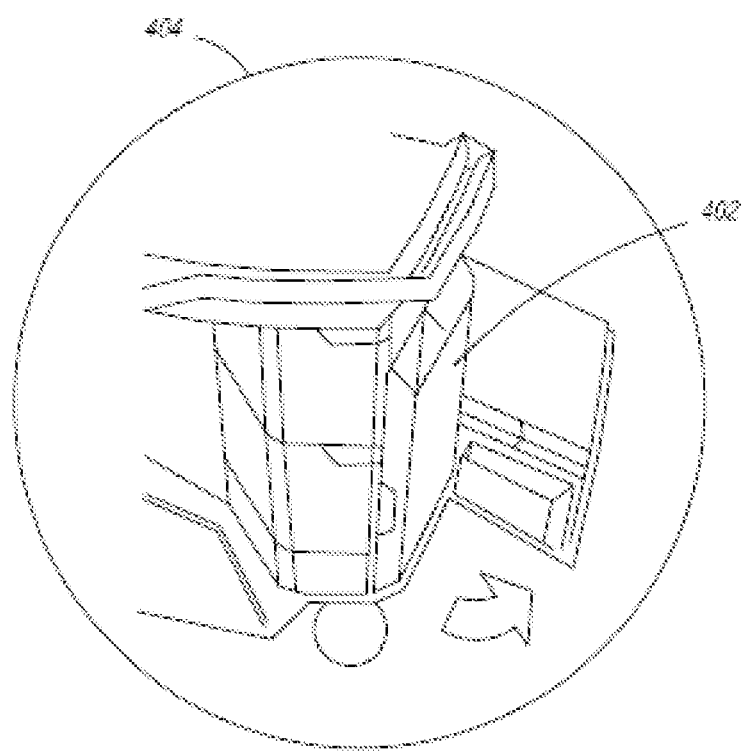
FIG. 4A is a schematic drawing of a side door storage integrated with the anesthesia system of the present specification.
Figure 4B:
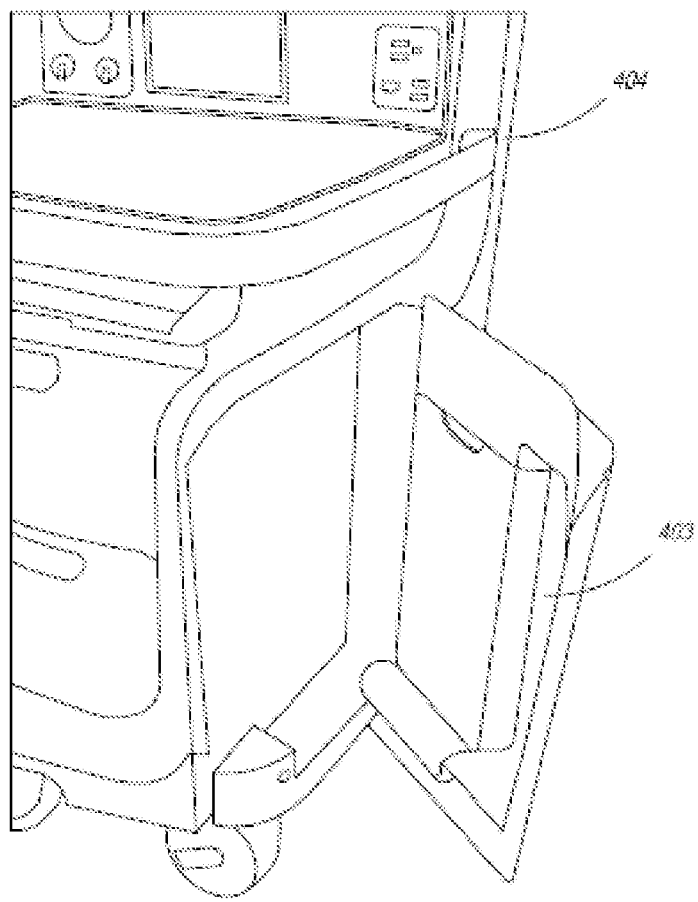
FIG. 4B is an illustration of an open side door storage area of the anesthesia system of the present specification.
Figure 4C:
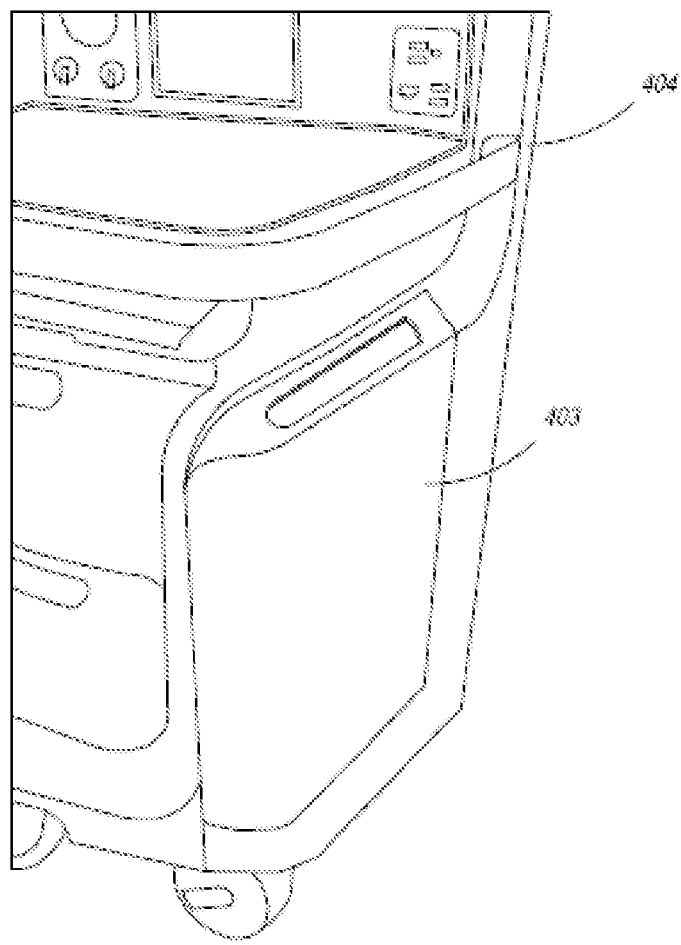
FIG. 4C is an illustration of a closed side door storage area of the anesthesia system of the present specification.

FIG. 4A illustrates the side storage 402 provided in the AO 404 in accordance with an embodiment of the specification. The side storage 402 may be used by a clinician to store odd shaped and longer items that would not typically fit well in storage drawers. FIG. 4B is an illustration of the side storage door 403 of the AO 404 in an open configuration. FIG. 4C is an illustration of the side storage door 403 of the AO 404 in a closed configuration.

Figure 5A:
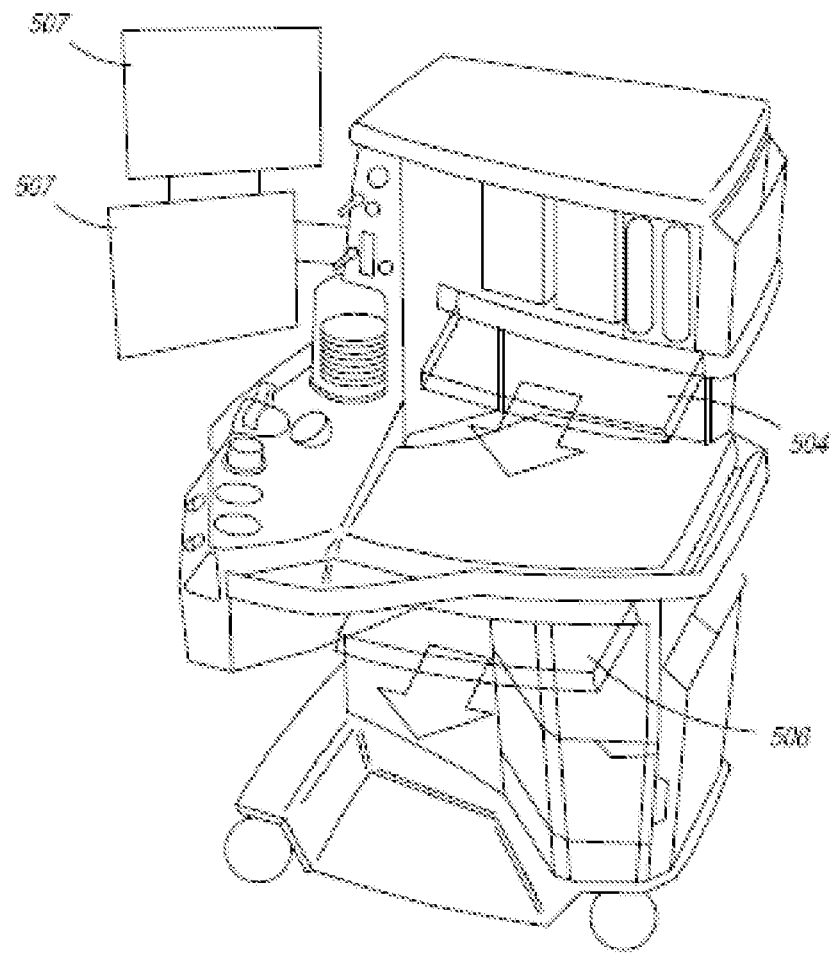
FIG. 5A is a schematic drawing of an upper and lower pull out shelf integrated with the anesthesia office portion of the anesthesia system of the present specification.

FIG. 5A illustrates pull-out shelves in the AO in accordance with an embodiment of the specification. Pull/slide-out shelves/trays 504 and 506 are provided at different heights and can be used for a plurality of purposes such as for placing a computer keyboard. Further, also shown in FIG. 5A is at least one moveable monitor screen or display 507.

Figure 5B:
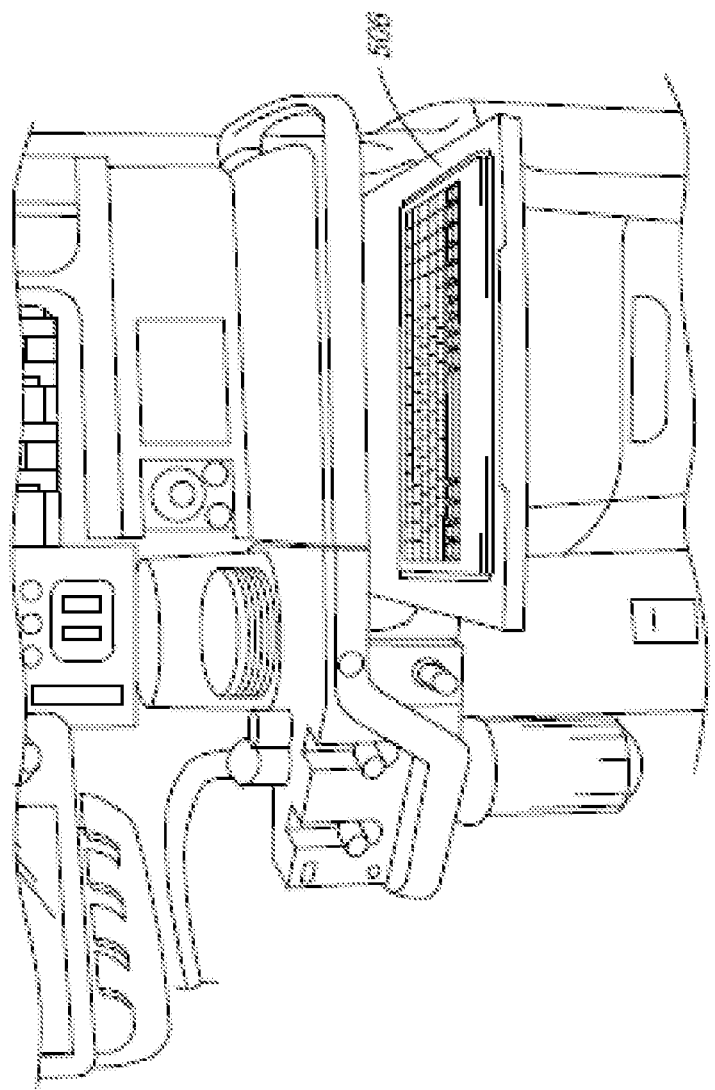
FIG. 5B is an illustration of a lower pull out shelf integrated with the anesthesia office portion of the anesthesia system of the present specification, in an open position.
Figure 5C:
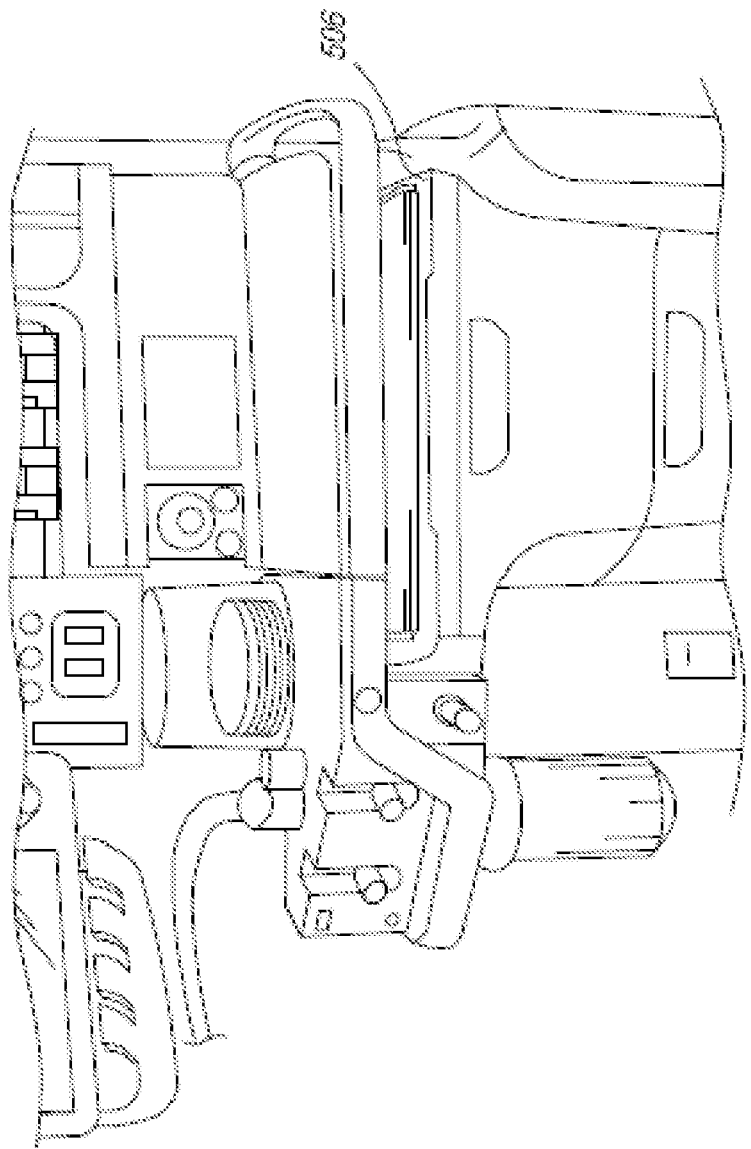
FIG. 5C is an illustration of a lower pull out shelf integrated with the anesthesia office portion of the anesthesia system of the present specification, in a stowed position.

FIG. 5B illustrates lower pull-out shelf 506, when it is pulled out of the AO of the system, further showing a keyboard on the pull-out shelf. FIG. 5C shows the lower pull-out shelf 506 in a hidden configuration, when it is stowed into the AO of the system.

Figure 5D:
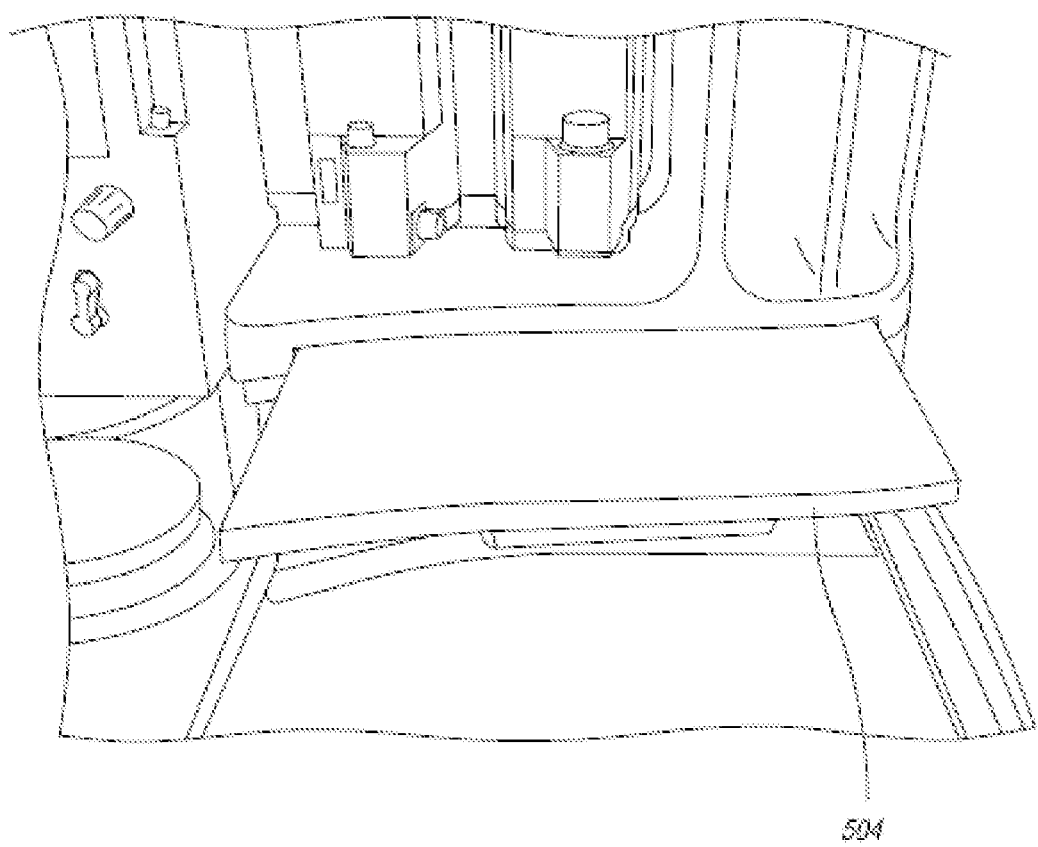
FIG. 5D is an illustration of an upper pull out shelf integrated with the anesthesia office portion of the anesthesia system of the present specification, in an open position.
Figure 5E:
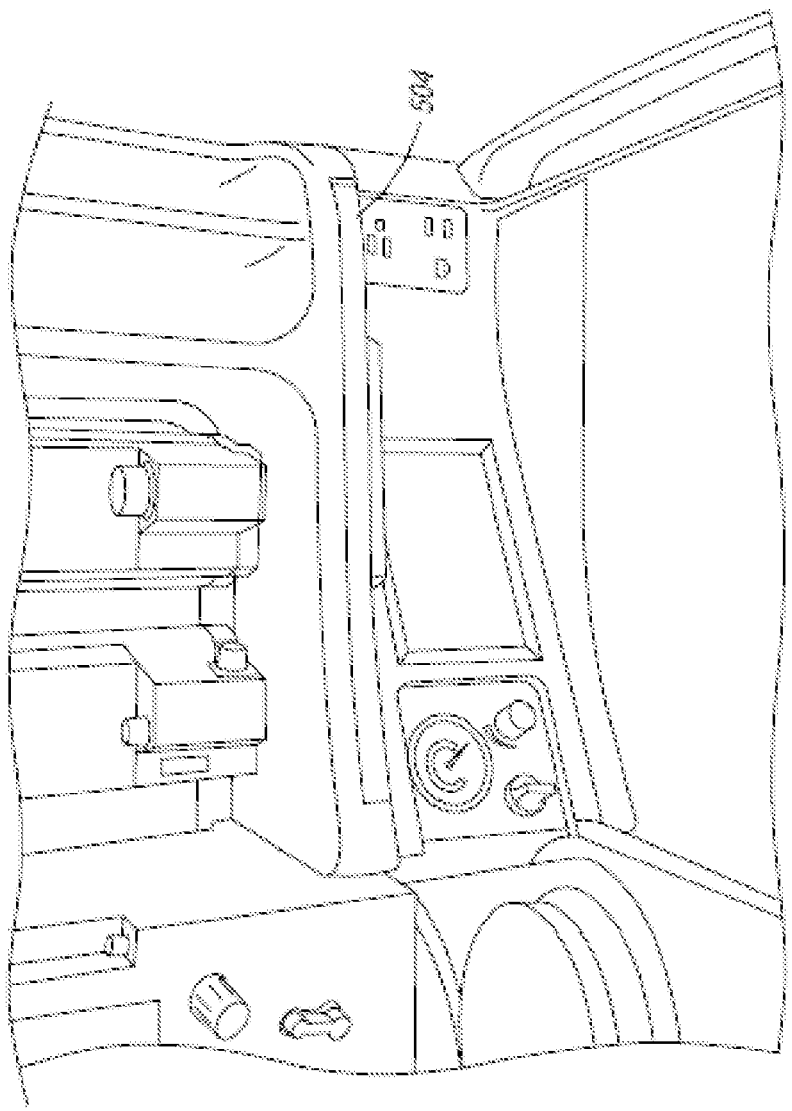
FIG. 5E is an illustration of an upper pull out shelf integrated with the anesthesia office portion of the anesthesia system of the present specification, in a stowed position.

FIG. 5D illustrates upper pull-out shelf 504, when it is pulled out of the AO of the system. In one embodiment, upper pull-out shelf can be used as a writing desk for the clinician to take notes while he or she is standing. FIG. 5E shows upper pull-out shelf 504 in a stowed or hidden configuration.

Figure 6A:
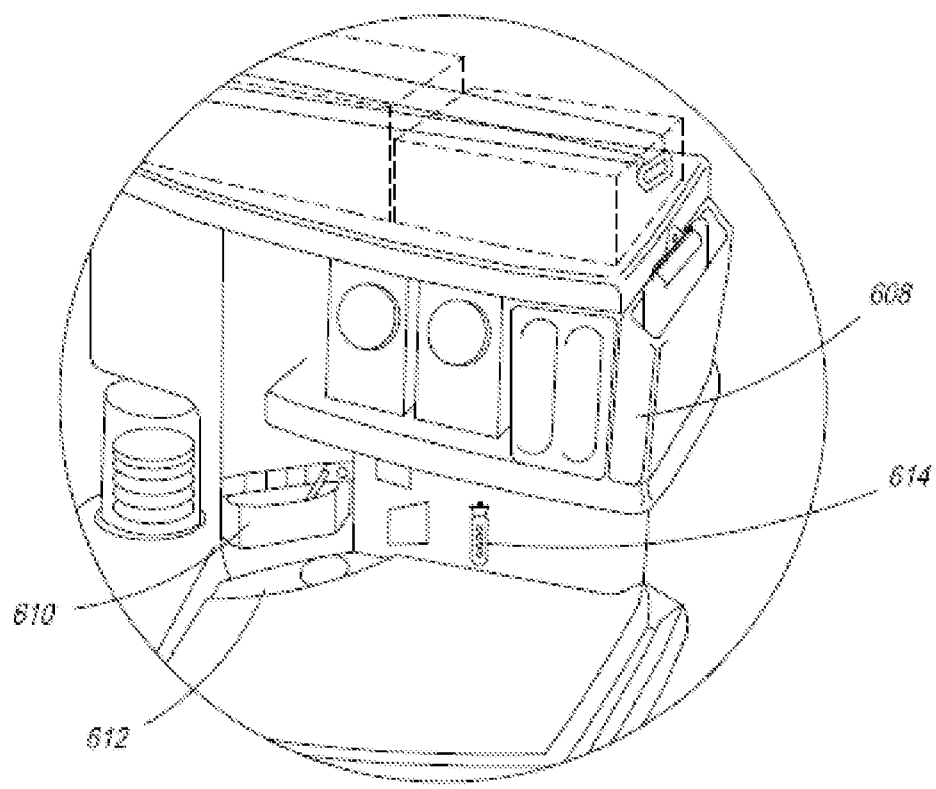
FIG. 6A is a schematic drawing of storage and electrical connection areas integrated with the anesthesia office portion of the anesthesia system of the present specification.
Figure 6B:
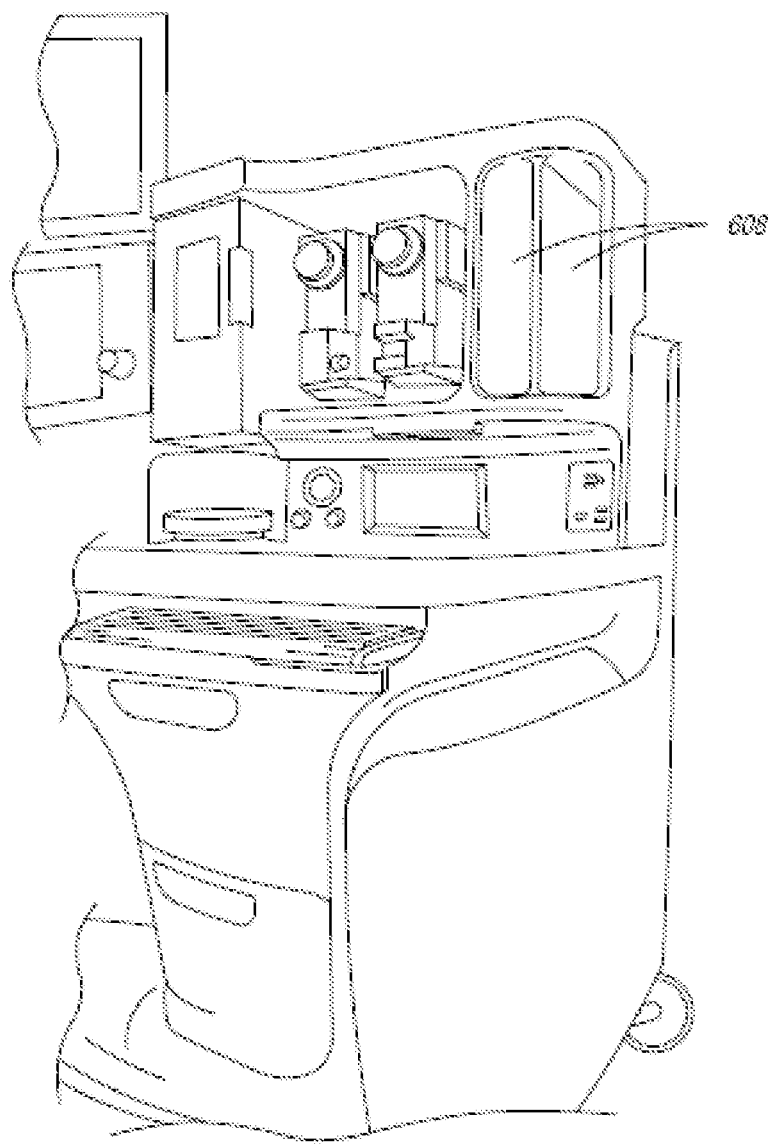
FIG. 6B is an illustration of a storage area integrated with the anesthesia office portion of the anesthesia system of the present specification.
Figure 6C:
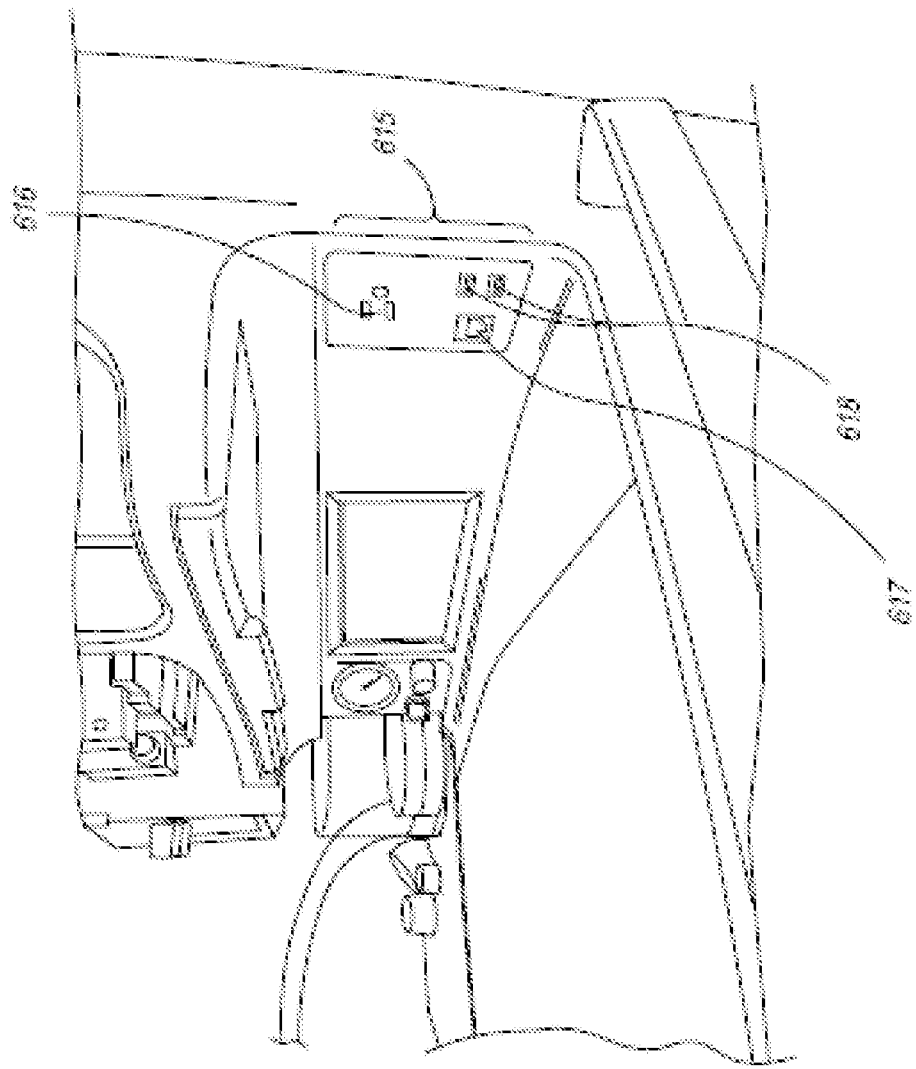
FIG. 6C is an illustration of an electrical connection area integrated with the anesthesia office portion of the anesthesia system of the present specification.

FIG. 6A illustrates space provided for storage and for electrical connections in the AO in accordance with an embodiment of the specification. In one embodiment, storage cubbies 608 and 610 may be used for storage of office items like pens, notes, clipboards, files, etc. The electrical connectors 612 and 614 may be used by clinicians for connecting their personal electronic devices. FIG. 6B is a further illustration of storage cubby 608. FIG. 6C is an illustration of one embodiment of an electrical connection area 615, which may include three-prong outlet 616, Ethernet port 617, and at least one USB port 618.

Figure 7A:
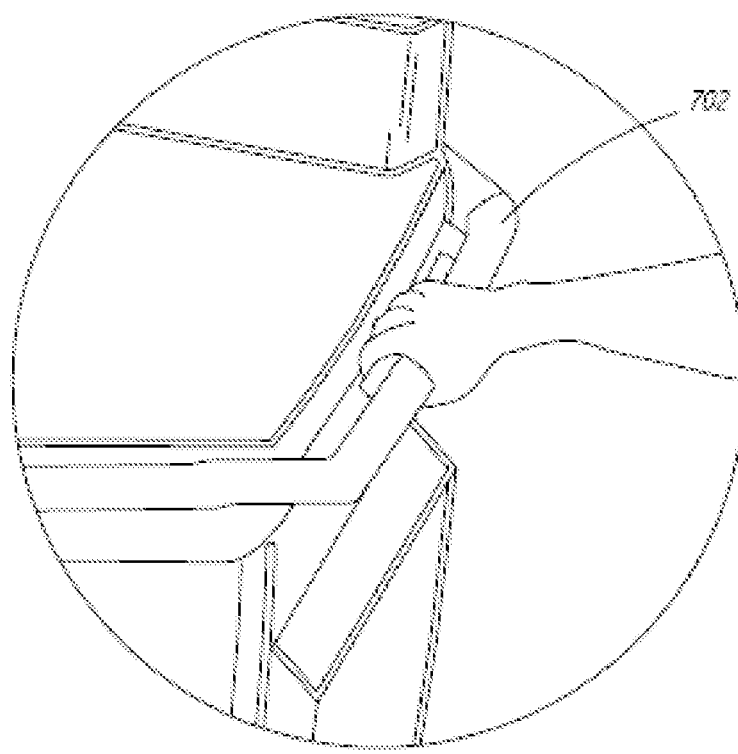
FIG. 7A is a schematic drawing of a handle activated castor lock provided in the anesthesia office (AO) in accordance with an embodiment of the present specification.
Figure 7B:
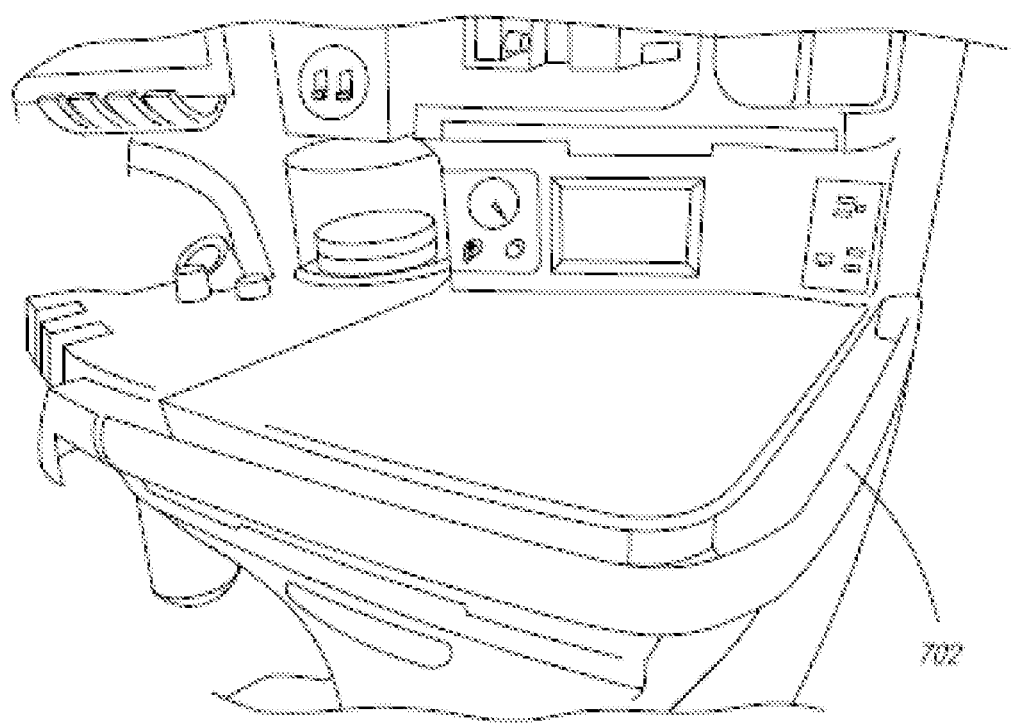
FIG. 7B is an illustration of a handle activated castor lock provided in the anesthesia office (AO) in accordance with an embodiment of the present specification.

FIG. 7A illustrates a handle activated castor lock provided in the AO in accordance with an embodiment of the specification. The handle-based lock 702 allows quick and small adjustments of the position of the anesthesia system. FIG. 7B is a further illustration of handle-based lock 702.

Figure 8:
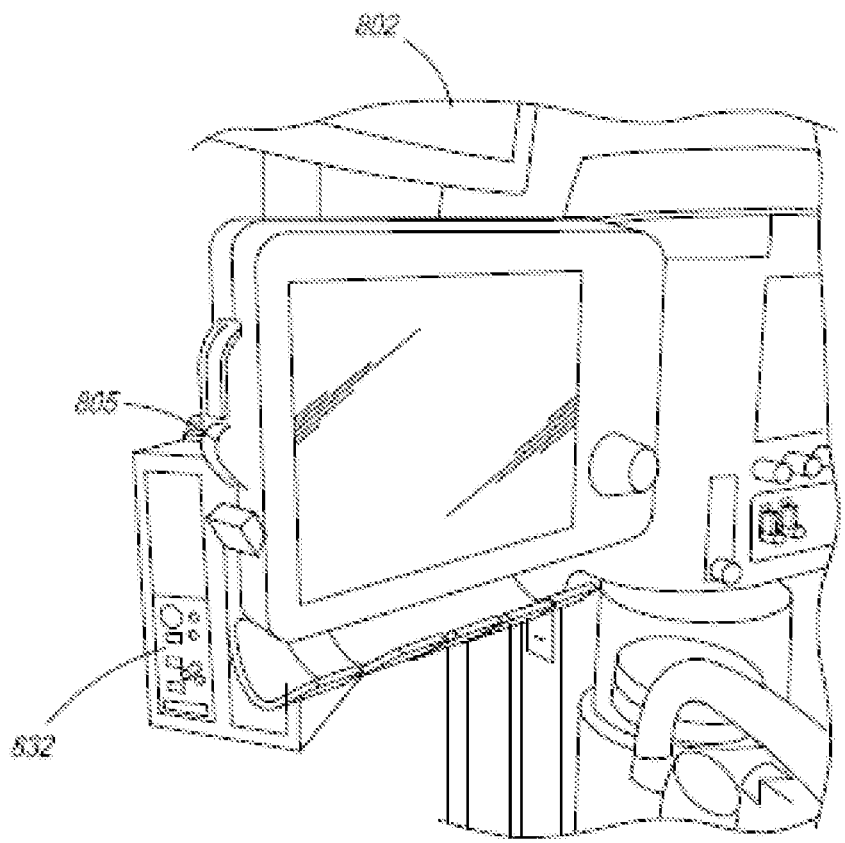
FIG. 8 is an expanded view of a tape dispenser area and physiologic monitor connections provided in the clinical center of the anesthesia system of the present specification.

FIG. 8 illustrates a medical tape dispenser 805 provided on the CC 802 in accordance with an embodiment of the specification. FIG. 8 also shows the physiological monitor (shown as 132 in FIG. 1C) parameter connections 832.

Figure 9A:
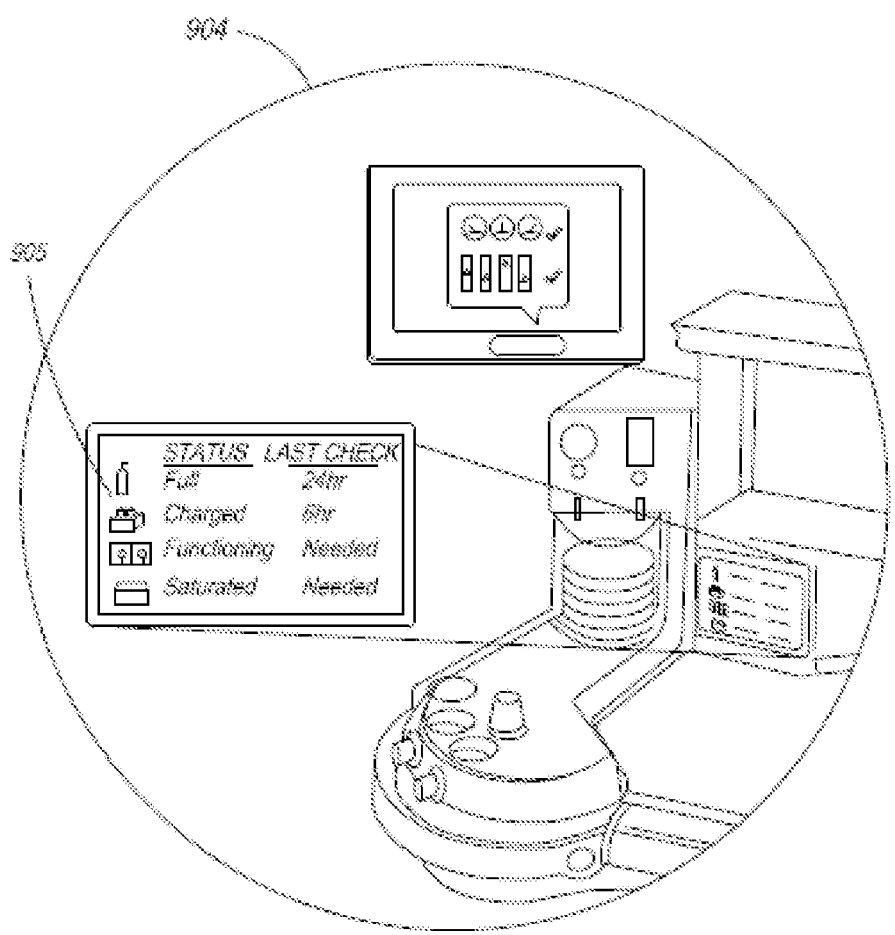
FIG. 9A is a schematic drawing of the system status computer provided with the anesthesia system of the present specification.

As shown in FIG. 9A, in one embodiment, the AO 904 includes a system status computer (SSC) 905 for conveying information to the user concerning the status of the anesthesia system's pneumatic, electrical, software (SW) and communication functions. The SSC 905 collects all information related to the technical status of the anesthesia system into one small display unit.

This provides the user with an intuitive separation of the anesthesia system's operation and functional information, from the clinical information associated with the therapy that the system is providing. The SSC 905 off-loads functions from a main clinical display unit (not shown) and provides an intuitive separation of technical measurements from those used directly for clinical care.

In various embodiments the SSC 905 provides information such as: pipeline pneumatic pressures, cylinder pressures, AC electrical power status, DC electrical power status, backup up electrical power (e.g. battery) status, software version, internal CPU serial numbers and revisions, system time and date, timer and alarm status, unit operation hours, last checkout and status, etc. This information can be conveyed either in a numeric format or graphically via fill bars, or emulation of pressure gauges.

Figure 9B:
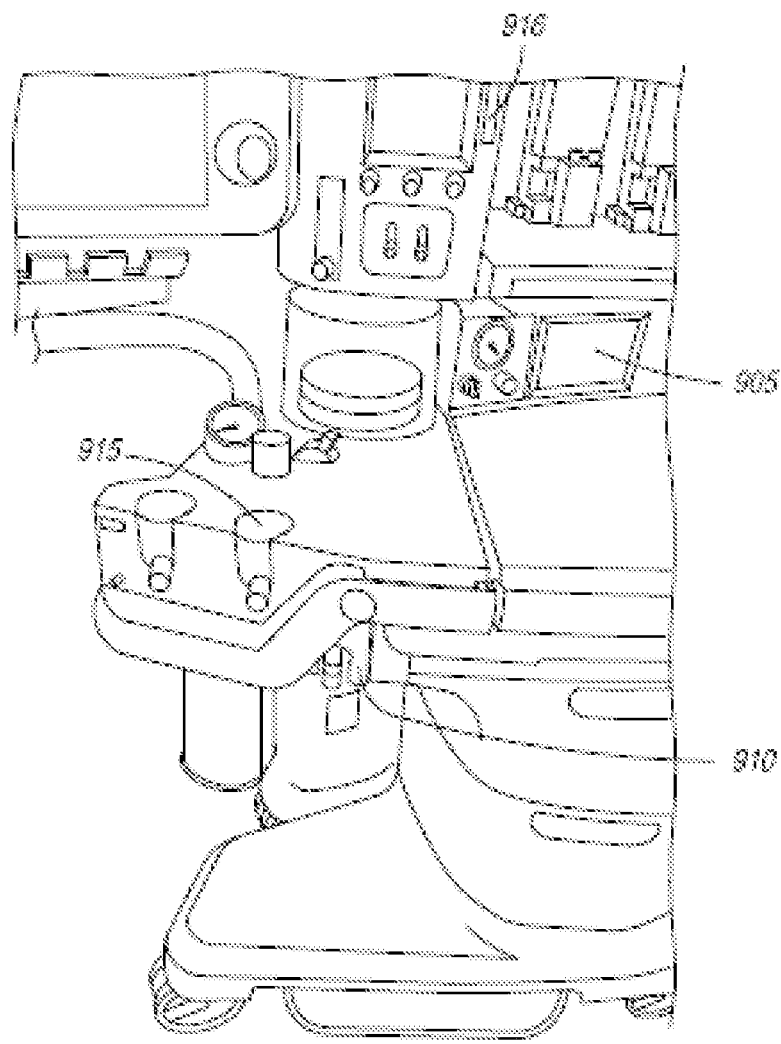
FIG. 9B is an illustration of the information projection lighting feature of the anesthesia system of the present specification.

In one embodiment, the SSC 905 remains powered on, available to present its information, even when the anesthesia system is turned off or disconnected from mains supplies. In this manner, the SSC 905 remains continuously ready to provide all data, but specifically cylinder pressure and pipeline pressure information to the user without activating the main portion of the anesthesia system. The SSC 905 may operate in a sleep/dormant mode when the power of the anesthesia system is turned off in order to conserve power and its display is turned on by a single user touch. The SSC 905 is capable of operating on battery power, allowing observation of system status even if the system is not connected to AC mains. Prior art systems utilize a mix of mechanical gauges and measurements displayed on a clinical display unit in order to convey system status information to the user. In an embodiment, by utilizing flat liquid crystal display (LCD) technology, the SSC 905 can be placed under a transparent surface of the AO, such as a flat work surface. The collection of all relevant system information in an electronic format obviates the need for mechanical gauges that consume significant space on the usable face of the anesthesia system. In the AO, the space normally used for mechanical gauges in conventional systems is freed up and is better utilized for storage or other office type functions. FIG. 9B provides an illustration of SSC 905.

Information Projection Lighting

In one embodiment of the present specification, direct lighting of an area of the system in association with an alarm, for example, any area of the anesthesia system being suspected of undergoing a technical problem, is provided, in order to unambiguously and intuitively guide the user's attention to the likely source of the problem reflected by the alarm. Thus, the information projection lighting of the present specification indicates an anomalous operational condition by illuminating the portion of the anesthesia system causing or likely to cause the anomalous/alarm condition.

For example, in an anesthesia system, a case of "sticking" non-return valves (check valves) may manifest as an inability to ventilate a patient. Even though an alarm message indicating a low ventilation condition may be generated, the direct lighting feature of the present specification causes a red flashing light to emanate from the check valve area, thereby guiding the user's attention to the potential source of the problem. In one embodiment, this lighting may be very dispersive in nature causing the whole check valve dome to light with red or other colors. In various embodiments, if more than one function of the system could be the cause for the alarm, multiple areas will flash light or a user will be guided to step through them in a sequence, for example, most likely to least likely.

In one embodiment, information projection lighting is used for identification of proper attachments and work zones. For example, many known anesthesia systems use a "common gas outlet" (CGO) for induction purposes. This requires a user to select CGO as the source of common gas using the anesthesia system's controls. To eliminate a potential error of having a patient attached to the CGO without it being selected as the source of the common gas, information projection lighting is used to illuminate the concerned port and attached translucent tube. In one embodiment, as shown in FIG. 9B, if the CGO is not selected, the port 910 is illuminated in a first color, such as amber; if the CGO is selected via rotating the port body to a horizontal position, the port lighting is illuminated in a second color, such as green, while the ports of the circle system 915 are simultaneously illuminated in a third color, such as red, indicating that they are not in use.

Figure 10A:
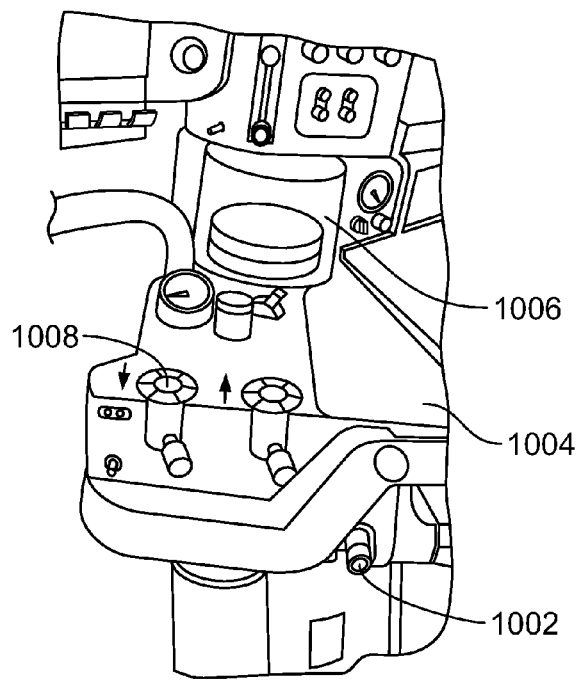
FIG. 10A is an illustration of the common gas outlet (CGO) port provided in the anesthesia system of the present specification, in a horizontal and active position.
Figure 10B:
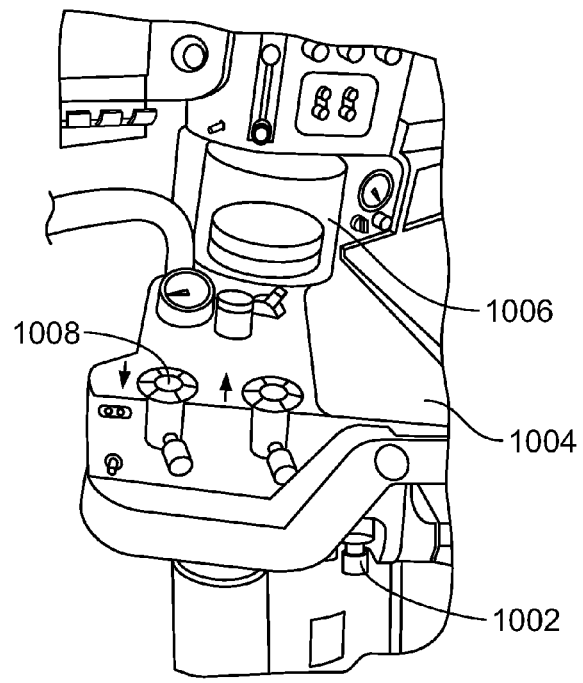
FIG. 10B is an illustration of the CGO port provided in the anesthesia system of the present specification, in a vertical and inactive position.

Referring now to FIGS. 10A and 10B, a switch 1002 is provided as a two position lever for a moveable CGO that is activated when the port is rotated up to a horizontal position. As shown in FIG. 10A, in a first position, switch 1002 is in a horizontal position and activates the CGO port. The first position is preferably parallel to a work surface 1004 of the system. As shown in FIG. 10B, in a second position, switch 1002 is preferably in a vertical position, and orthogonal to a work surface 1004 of the system and deactivates the movable CGO. FIGS. 10A and 10B also show breathing circuit attachment ports 1008, described in detail above with respect to FIGS. 2G, 2H, 2I, 2J and 2K.

A similar use of the information projection lighting may be made in the bag to vent area. In an embodiment, when "vent" operation is selected, the bellows itself could be lit in any color, such as green. FIGS. 10A and 10B show the bellows 1006 lit when ventilation is active. Similarly, the APL valve and circuit pressure gauge are illuminated with a different light color, such as amber, when the ventilator of the anesthesia system is in an inactive off state.

In one embodiment, information projection lighting is used to indicate status (such as, on/off or engage/disengage or active/inactive) of the plurality of controls by direct illumination of the controlled function. By way of example, with reference to FIG. 1A, the arm of bag 153 is illuminated to indicate ventilator inactive/active or off/on state; the $CO_2$ absorbent canister 155 is illuminated if the canister 155 is disengaged from the breathing circuit and/or if there is an alarm for high $CO_2$ in the respiratory gas; the side stream respiratory gas monitor water trap is illuminated if the respiratory gas monitor (housed within physiological monitor 132 of FIG. 1C) is alarming for an obstruction. In various embodiments the information projection lighting may be used for indicating vaporization on/off, circle system ports enabled/disabled depending upon whether the ventilator is in active/inactive state, suction on/off, auxiliary oxygen on/off, carbon dioxide bypass on/off, etc.

Persons of ordinary skill in the art should appreciate that the information projection lighting, of the present specification, is adjustable for color, intensity and/or flashing rate in accordance with a user's needs/preferences.

Hence, the present specification provides a system and method for the identification of problem areas in an anesthesia system in an unambiguous and intuitive manner through the use of subtle lighting of suspected problem areas in association with these alarms. With the present specification, the user will be immediately directed to the area of the system in need of examination or correction and will not incur unnecessary distraction or defocus from patient care. Further, the visual lighting of the affected system area will enable other personnel in the OR to assist in the diagnosis or recognition of the problem. Through information projection visual lighting, operational elements of the system whose function may be engaged or disengaged are clearly identified, decreasing the potential for clinical errors.

User Interface Alarm Lighting

In an embodiment, the present specification is directed toward an anesthesia delivery system which provides a user interface alarm lighting feature. The feature provides a lighting strip on a graphical user interface (GUI) of the anesthesia system to enable a user to quickly determine not only if an alarm is active, but also a priority level of the active alarm. In an embodiment, an illuminated strip of colored light is presented to a user at a top corner of the GUI in order to draw the user's attention to an alarm condition. Further, in an embodiment, the color of the illuminated strip is associated with a priority level of the alarm condition. For example, a yellow color illuminated strip may be displayed to indicate a medium priority alarm whereas a red color illuminated strip may be associated with a high priority alarm. Hence, the user interface alarm lighting feature enables users to quickly determine an alarm condition, and can be especially beneficial when a user, such as an anesthesiologist, is too far from the anesthesia system to actually read an alarm message.

Figure 11A:
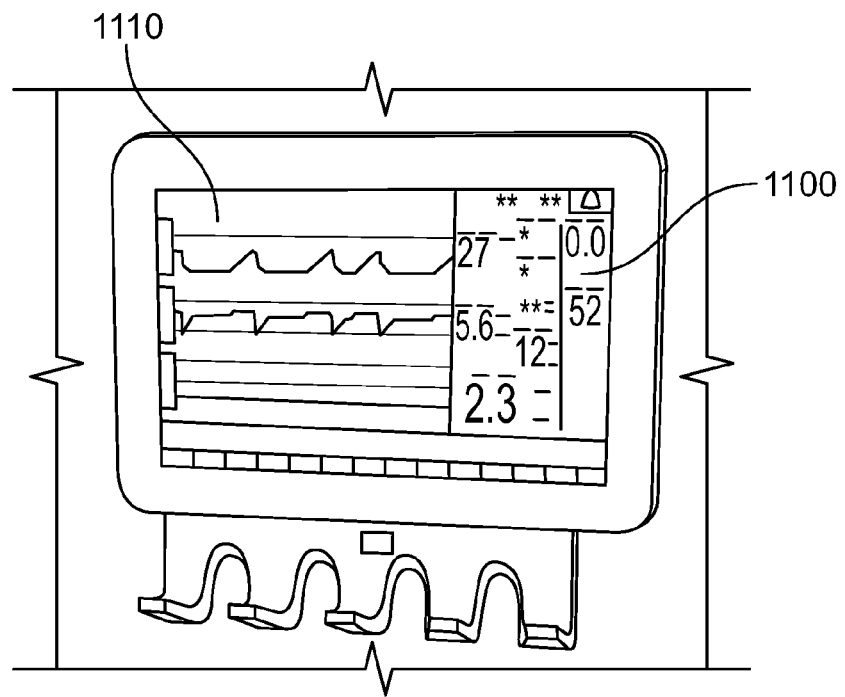
FIG. 11A illustrates an exemplary graphical user interface (GUI) screen of the anesthesia system, in accordance with an embodiment of the present specification.

FIG. 11A illustrates an exemplary GUI screen of the anesthesia system, in accordance with an embodiment of the present specification. In an embodiment, a GUI screen 1100 comprises an alarm block area 1110 at a top left corner. In other embodiments, the alarm block area 1110 is provided at any convenient location on the GUI 1100. As illustrated in FIG. 11A, the alarm block area 1110 has no coloration (appears black), conveying that no alarm condition is present, and hence, there is no alarm message being displayed.

Figure 11B:
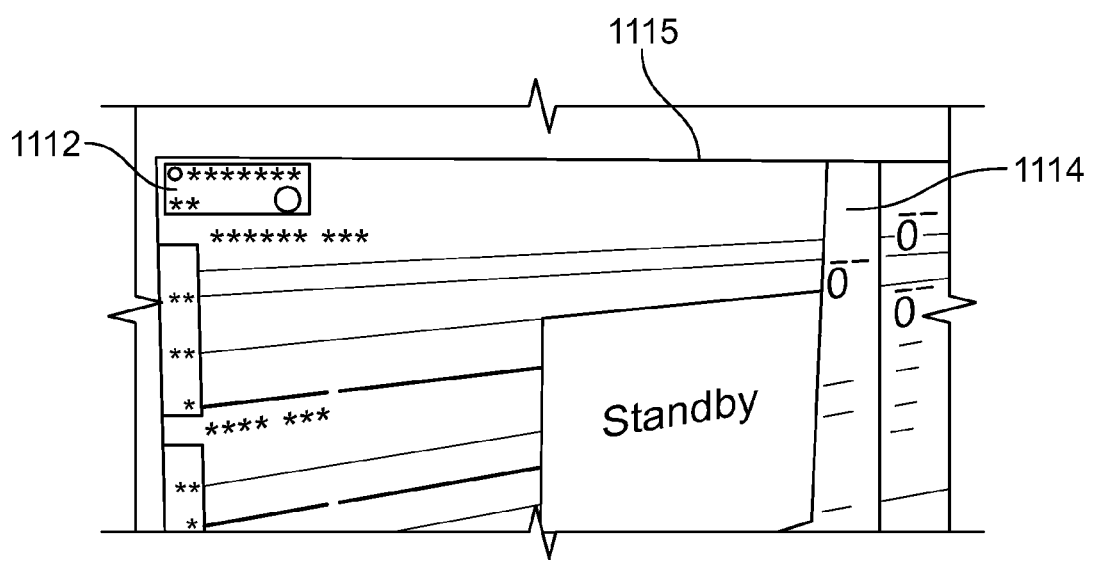
FIG. 11B illustrates another exemplary GUI screen of the anesthesia system, in accordance with an embodiment of the present specification.

FIG. 11B illustrates another exemplary GUI screen of the anesthesia system, in accordance with an embodiment of the present specification. As illustrated in FIG. 11B, an alarm block area 1112 of a GUI screen 1114 displays a colored (yellow) alarm line and an alarm message stating "Check Sample Line". In an embodiment, the displayed yellow alarm line conveys a medium priority alarm. Further, in an embodiment, the displayed alarm line fades out after a predetermined interval of time, whereas in another embodiment, the alarm line is displayed intermittently at predetermined intervals. In yet another embodiment, the alarm line is displayed as a solid line until a corresponding alarm condition passes or a predefined action is taken by a user. Also depicted in FIG. 11B, across the top center portion of the screen 1114, is a colored alarm bar 1115. In one embodiment, the alarm bar 1115 matches the color (i.e. yellow) of the alarm line in the alarm block area 1112. The alarm bar 1115 occupies a greater area of the screen 1114 and is more prominently displayed than the alarm line of the alarm block 1112, thereby assisting in visualization by caregivers.

Figure 11C:
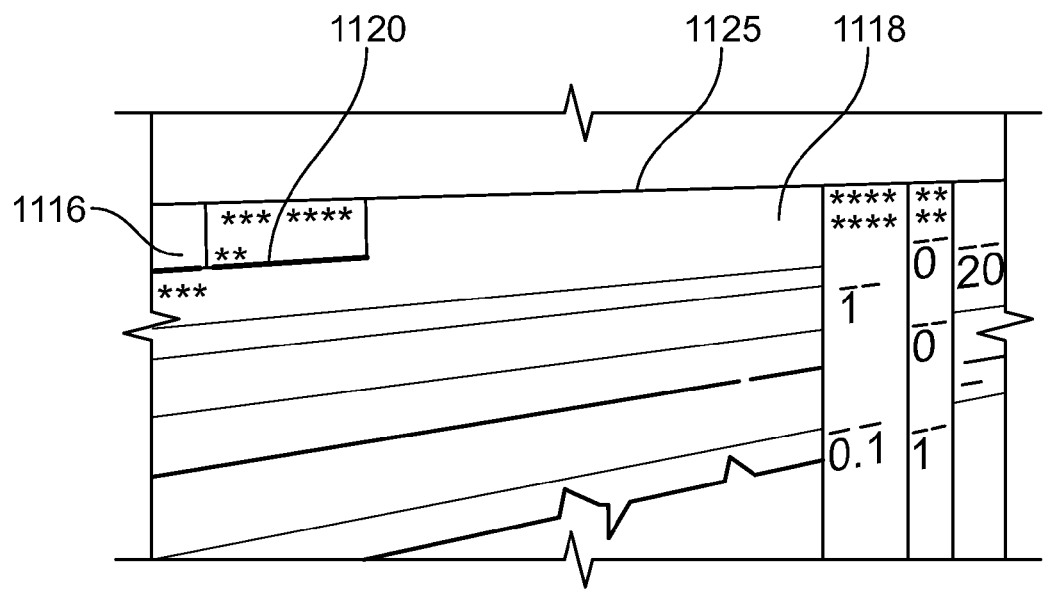
FIG. 11C illustrates yet another exemplary GUI screen of the anesthesia system, in accordance with an embodiment of the present specification.

FIG. 11C illustrates yet another exemplary GUI screen of the anesthesia system, in accordance with an embodiment of the present specification. As illustrated in FIG. 11C, a first colored (red) alarm line is displayed in a first alarm block area 1116 (displayed partially) of a GUI screen 1118. In an embodiment, the displayed red alarm line is associated with a high priority alarm condition. FIG. 11C also illustrates a second colored (yellow) alarm displayed in a second alarm block area 1120. In one embodiment, the color of the alarm bar 1125 is associated with the highest priority of alarms currently occurring. According to this embodiment, in FIG. 11C, the alarm line is red and is associated with a high priority alarm since both high and medium priority alarms are active. In various embodiments, a plurality of alarm lines conveying the same or different alarm priority levels may be displayed simultaneously on a GUI screen of the anesthesia system.

Revert from Auto Alarm Limits

As is commonly known in the art, when using anesthesia delivery systems that employ alarms, it is desirable to have an "auto-limits" function that automatically adjusts the system's alarm limits around currently monitored values based on a predefined algorithm. This function aids a clinician by enabling a rapid setting of all alarms to appropriate levels and eliminates the need for the clinician to individually and tediously adjust high and low values for each alarmed parameter. Thus, it is also desirable to have an "undo" or "revert" function available, in order to put the alarms back to a state in which they were prior to the auto-limit activation to allow for situations in which, for example, the alarm auto-limit values are inadvertently activated, the clinician does not want to hold the limits that were generated automatically, and/or the clinician desires to manually set alarm limits.

Figure 12A:
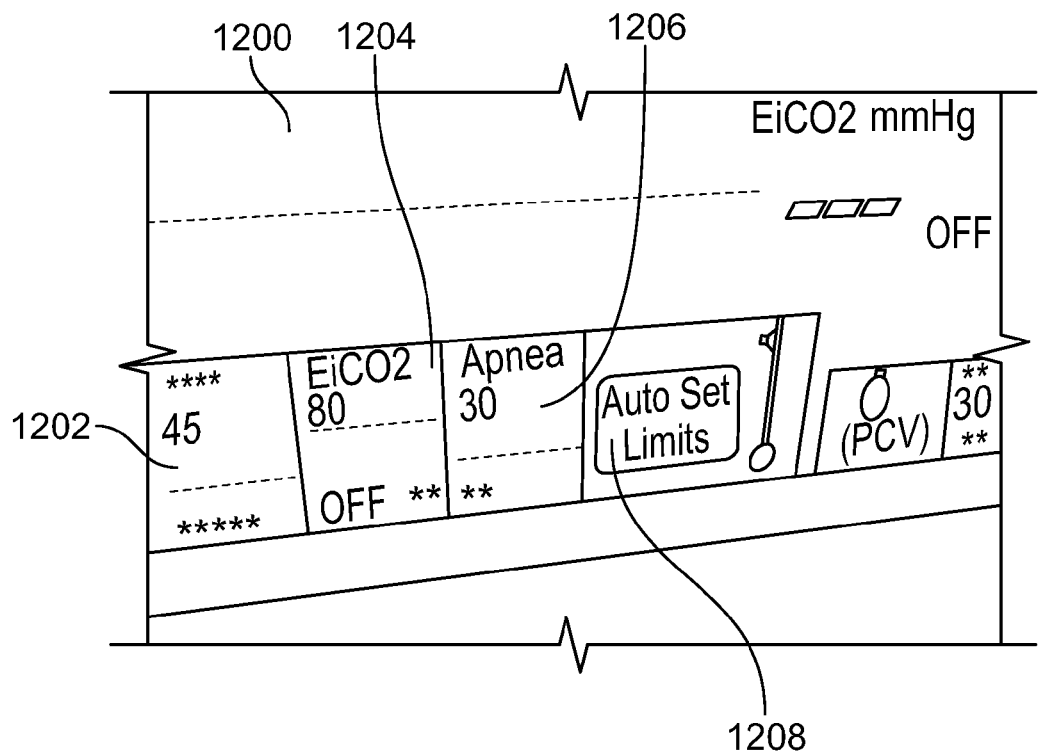
FIG. 12A illustrates a monitor screen displaying a plurality of icons for setting alarms, in accordance with an embodiment of the present specification.

The present specification provides a 'revert from auto limits' functionality incorporated in the anesthesia system which may be used in an intuitive and predictable fashion, thereby increasing the usability of 'auto-limits' and 'revert from auto-limit' functions as compared to prior art anesthesia systems. FIG. 12A illustrates a monitor screen 1200 displaying a plurality of icons for setting alarms, in accordance with an embodiment of the present specification. As illustrated, the monitor screen 1200 displays icons for individually setting alarm limits corresponding to a plurality of medical functions, including but not limited to 'pressure (plimit)' 1202, 'end tidal $CO_2$ ($EtCO_2$)' 1204, and 'apnea' 1206. The monitor screen 1200 also displays an icon 'auto-set limits' 1208 for automatically setting alarm limits. By clicking on icons 1202, 1204, or 1206, a user can set alarm limits for individual parameters and by clicking on the 'auto-set limits' icon 1208, the user can cause automatic adjustment of a plurality of predefined parameters.

Figure 12B:
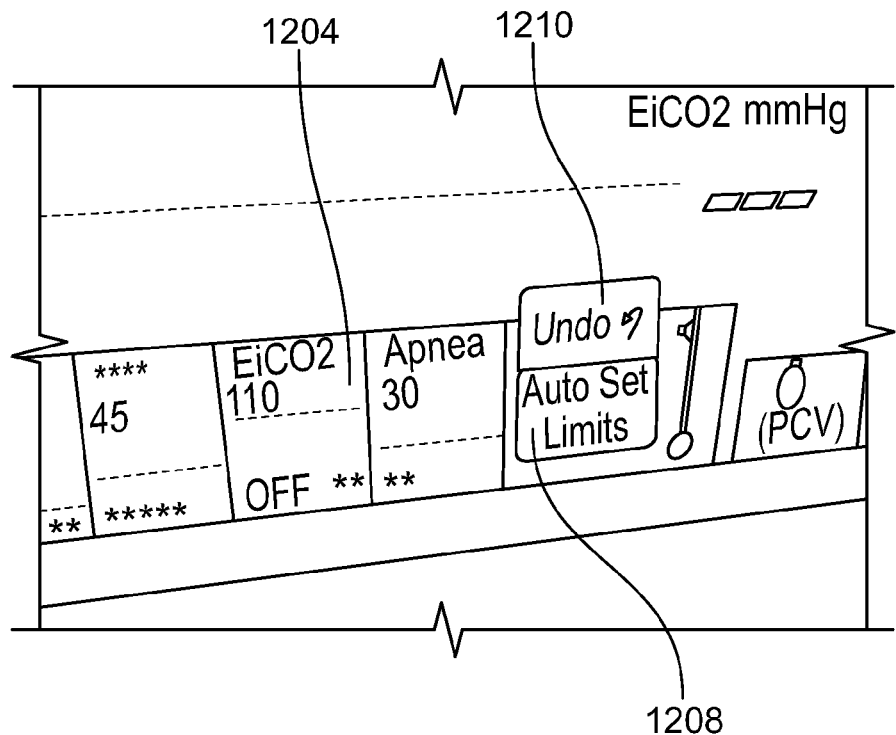
FIG. 12B illustrates another exemplary monitor screen displaying a plurality of icons for setting alarms, in accordance with an embodiment of the present specification.

FIG. 12B illustrates another instance of a monitor screen displaying a plurality of icons for setting alarms, in accordance with an embodiment of the present specification. Once the 'auto-set limits' icon 1208 is clicked, a plurality of predefined alarm parameters are automatically adjusted. In an embodiment, clicking of the 'auto-set limits' icon 1208 causes a change in the EtCO2 1204 parameter which is illustrated as having a limit of 80 in FIG. 12A to having a limit of 110 as illustrated in FIG. 12B. Once the 'auto-set limits' icon 1208 is clicked, an undo icon 1210 is displayed. A user may click on the undo icon 1210 in order to revert to the values of the plurality of alarm parameters that existed before the 'auto-set limits' icon 1208 was clicked. The undo icon 1210 may be clicked by a user to undo the effects of 'auto-set limits' function in cases where the function causes one or more alarm parameters to change in an undesired manner. The undo function increases the usability of the 'auto-set limits' function as a user is not required to individually adjust the value of one or more alarm parameters to their original values. A user may click on the 'auto-set limits' icon 1208 in order to observe the adjusted alarm parameter values and in case said values are undesirable, may click the undo icon 1210 to revert to the original values easily. If the undo icon 1210 is not clicked, the adjusted alarm parameter values continue to be used as the existing alarm limits. Once the alarm menu is exited, the undo icon 1210 is removed and a future return to the alarm menu would display a screen similar to that in FIG. 12A, without an undo icon but with the EtCO2 set to a value of 110 mmHg.

Figure 12C:
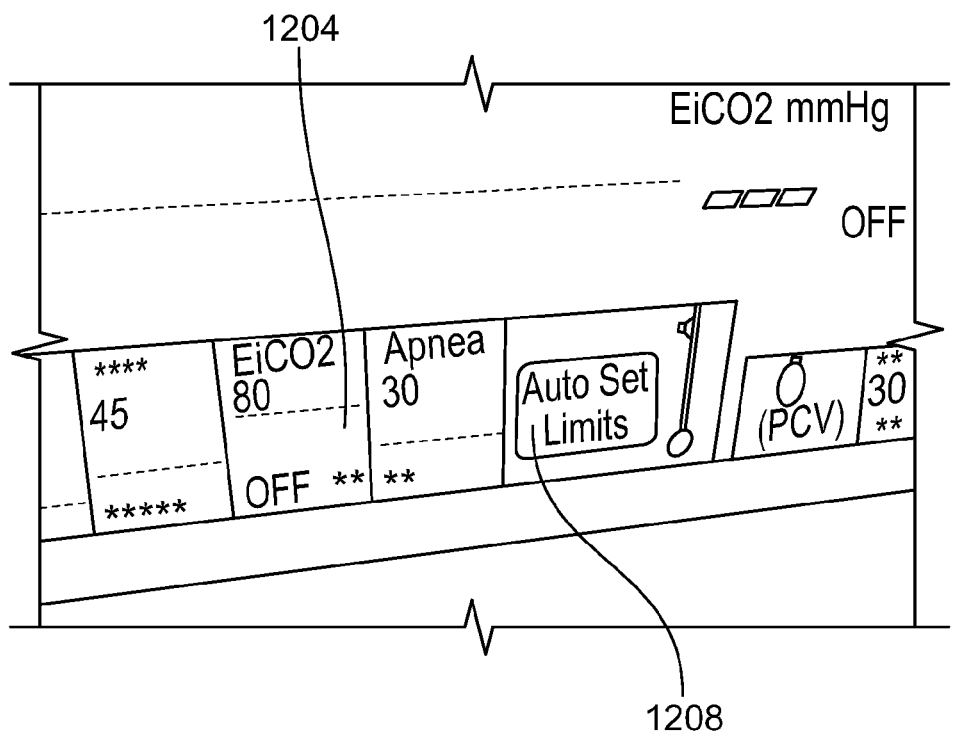
FIG. 12C illustrates yet another exemplary monitor screen displaying a plurality of icons for setting alarms, in accordance with an embodiment of the present specification.

FIG. 12C illustrates yet another instance of a monitor screen displaying a plurality of icons for setting alarms, in accordance with an embodiment of the present specification. As illustrated in FIG. 12C, once the undo icon 1210 is clicked the values of alarm parameters adjusted by the clicking of the 'auto-set limits' icon 1208 revert to their original state. In an embodiment, clicking of the undo icon 1210 causes the EtCO2 1204 parameter, which is illustrated as 110 in FIG. 12B, to revert back to its original value of 80 as illustrated in FIG. 12C.

Enhanced Flow Tube Visualization

In conventional anesthesia delivery and ventilation systems, flow tubes are commonly used to serve as a simple, clear, and reliable mechanical method to ensure proper operation of a device—often in the event of an electronic failure or as a cross check of the electronic flow readings. As shown in FIG. 9B, the present specification optionally includes an improved visualization method for a flow tube 916 used as a backup to electronic fresh gas flow measurement. An exemplary flow tube is described in U.S. patent application Ser. No. 12/775,719, entitled "Light Enhanced Flow Tube", filed on May 7, 2010 and assigned to the applicant of the present specification, and is herein incorporated by reference in its entirety.

Wireless Proximal Sensor(s)

In an embodiment, the present specification provides a single, small sensor solution for proximal placement without tubes or connections back to the anesthesia system. Using small sensors positioned directly at the airway provides optimal flow and pressure measurement signals. The integral docking station for the wireless sensor not only provides power recharge and signal connection, but also provides a physical storage location for the sensor between cases or when it is not in use. In an embodiment, the anesthesia system of the present specification provides an autoclavable flow sensor with a wireless chipset, including CPU power to perform wireless function, sensor sampling and processing.

In an embodiment, the wireless proximal sensor provides reliable communications in an operating room environment up to a distance of 30 feet. In various embodiments, wireless technologies such as 802.15.4 (low-level IEEE spec for Zigbee), SynkroRF (developed by Freescale), RF4CE (Industry Consortium), ANT and/or ANT+, Bluetooth, Low Power Bluetooth, etc. may be employed. In various embodiments the wireless proximal sensor fits within a battery based power budget and its design is tolerant to high humidity environments.

In one embodiment, an airway pressure sensor having the following characteristics is employed:
Dynamic range: −20 to 120 $cmH_2O$
Resolution: 0.01 $cmH_2O$ (calculates to about 14-bit resolution)
Bandwidth: 60 Hz (guidance for on board analog and digital filtering)
Output (decimated) sample rate: 250 Hz (4 msec period)

In one embodiment, a differential pressure sensor is employed having the following characteristics:
Dynamic range: ±2.5 $cmH_2O$
Resolution: 0.0004 $cmH_2O$ (calculates to about 14-bit resolution)
Bandwidth: 60 Hz (guidance for on board analog and digital filtering)
Output (decimated) sample rate: 250 Hz (4 msec period)

The use of a wireless sensor requires detection of loss of proper signal such as a data dropout for more than 12 to 50 msec, thereby causing the system's internal sensors to be used. Additionally, wireless battery monitoring predicts loss of signal, and a seamless use of backup sensor systems. The anesthesia system of the present specification is provided with this backup means via fresh gas flow sensors and a drive gas flow sensor. These sensors form a redundant network of flow information to be used for error checking the proximal sensor and continuity of ventilation delivery if the wireless proximal sensor becomes disabled.

Figure 9C:
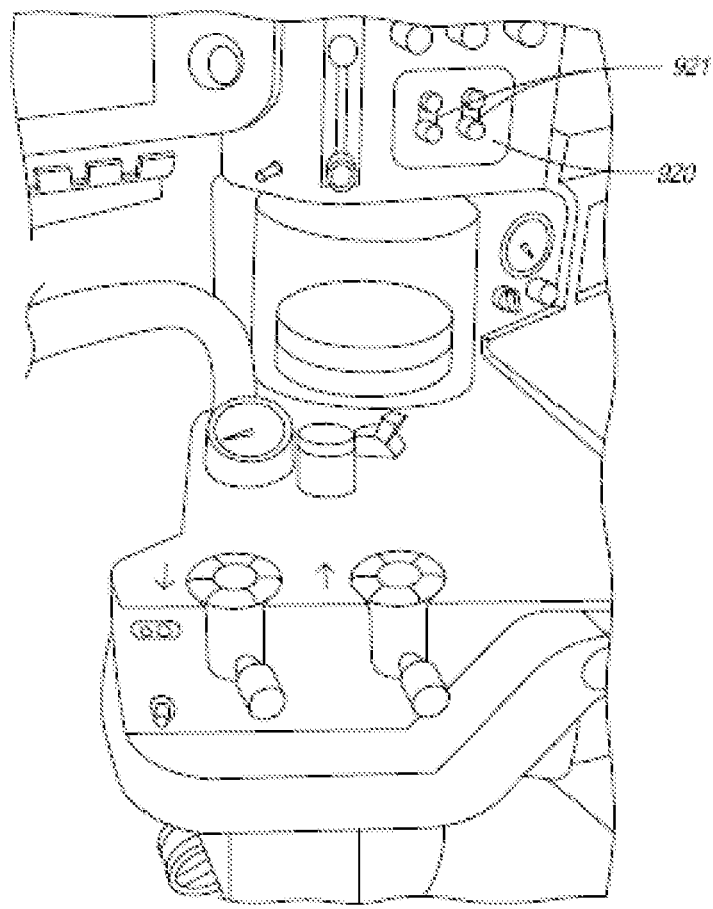
FIG. 9C is an illustration of the wireless sensor and sensor docking feature of the anesthesia system of the present specification.

In an embodiment, as shown in FIG. 9C, an integral "docking" station 920 for the wireless proximal sensors 921 is provided on the anesthesia system that provides a coded data communication channel as well as power for recharging the wireless sensor batteries. The wireless proximal sensor establishes a communication link to the anesthesia system only while physically sitting in the docking station. A user is required to remove the sensor from the docking station 920 and place it at the proximal airway. In an embodiment, the use of information projection lighting as described above provides information that the sensor channel is active.

In one embodiment, the wireless sensor is separated into two parts, a wireless communication pod and a sensor pod that is coupled to the wireless communication pod. Only the wireless communication pod, which provides communication to the anesthesia system, is placed into the docking station. For example, the wireless communication "pod" is attached to a "pitot" type flow sensor, in one embodiment.

Circle-Less Breathing Circuit

In one optional embodiment, the anesthesia system of the present specification provides a circle-less breathing circuit for patients. Most current anesthesia systems employ a 'circle circuit' that contains a $CO_2$ absorbent for recycling some amount of breathing gas which is then conveyed back to the patient. Conventional anesthesia systems also typically employ 'mixers' that combine oxygen, air and nitrogen gases prior to introduction into the circle circuit as 'fresh gas'.

Figure 13A:
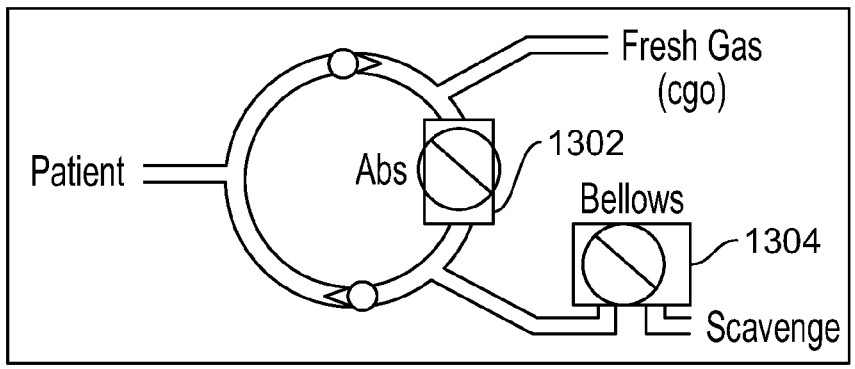
FIG. 13A is a diagram showing some basic elements of a conventional circle breathing circuit indicating which major elements have been eliminated, or are not required, in the circle-less breathing circuit of the anesthesia system of the present specification.

FIG. 13A illustrates some basic elements of a conventional circle breathing circuit indicating which major elements have been eliminated, or are not required, in the circle-less breathing circuit of the present specification. Absorber element 1302 and bellows 1304 have been eliminated in the circle-less breathing circuit provided by the present specification. Further, check valves used in the circuit illustrated in FIG. 13A are also replaced with active valves such as those used in typical, flow valve controlled ICU ventilators.

Figure 13B:
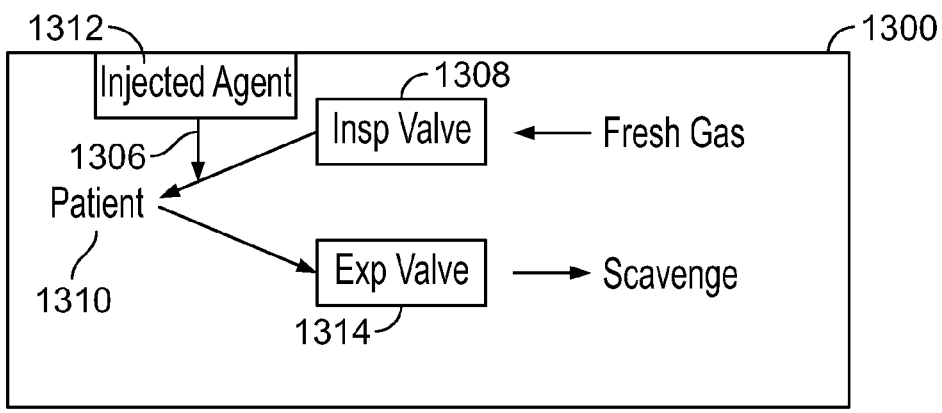
FIG. 13B illustrates a circle-less breathing circuit, in accordance with an embodiment of the anesthesia system of the present specification.

FIG. 13B illustrates a circle-less breathing circuit 1300, in accordance with an embodiment of the present specification. As shown, fresh gas is injected through an inspiratory valve 1308, mixed with an injected agent 1312, delivered to a patient 1310 and then led out via an expiratory valve 1314. In an embodiment, the fresh gas can be oxygen or air, thus requiring only a single control valve for inspiration. In another embodiment, the inspiratory valve 1308 comprises multiple control valves designed to blend oxygen, air and nitrous oxide directly into the circuit. In an embodiment, the source of the fresh gas may be a high pressure pipeline or cylinder supply and the function of the inspiratory valve 1308 may be accomplished with proportional solenoid valves such as those used on conventional ICU ventilators. Alternatively, a low pressure fresh gas source such as room air or oxygen concentrator may be employed and the inspiratory valve 1308 function may be accomplished by employing a turbine or piston device to generate the necessary patient circuit pressures.

In one embodiment the injected agent device 1312 utilizes gaseous anesthetic agent and is designed to control the injection of the agent to just the portions of the gas being delivered to the patient's lungs, since the circle-less circuit does not cause the gas provided through the inspiratory valve to be re-breathed. In an alternate embodiment, the agent is metered as a liquid and is vaporized into the gas stream utilizing a wick arrangement within the inspiratory portion of the breathing circuit tubing 1306.

Using the circle-less breathing circuit 1300, a pulse train of anesthetic gas may be injected in real-time into the inspiratory flow stream of a patient. The goal is to "phase" the pulse train of agent so that a required portion of the pulse lands in the patient's lung and the dead-space receives no agent. In accordance with an embodiment of the present specification, an optional technique to minimize agent usage is to shape the anesthetic gas pulse so the dead-space receives no agent. Typically, dead-space comprises about 20% of the tidal volume. At the end of inspiration, the dead-space is filled with fresh gas; "phasing" the pulse train of the agent can help ensure that this trailing gas contains no anesthetic agent.

Figure 13C:
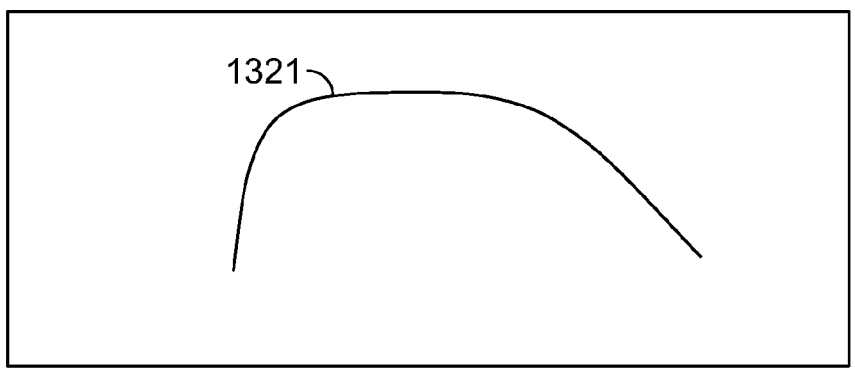
FIG. 13C illustrates an optimally shaped anesthetic gas pulse so that a pulse train of anesthetic gas may be injected in real-time into the inspiratory flow stream of a patient.

Also, since the patient is lying down, most of the posterior portion of the lung is perfused while the anterior portion is relatively less perfused. Hence, an optimal shape of the pulse 1321 is square with some taper towards the end, as illustrated in FIG. 13C. In an embodiment, a gas monitor is employed to help with the dead-space and pulse phasing. Thus, the volume of patient-generated carbon dioxide ($VCO_2$) and end-tidal carbon dioxide ($EtCO_2$) can be used to determine the dead-space which is about equal to the volume of the endotracheal tube (ETT).

The agent injection is then linked to the delivery of an inspiration breath and the end of agent delivery is phased to the inspiratory gas volume that is projected to enter the dead space.

Hence, the anesthesia system of the present specification provides a circle-less breathing system at a lower cost than conventional circular breathing circuits as a plurality of elements of conventional circuit such as bellows, absorber, replaceable absorber canister, mixer and conventional vaporizer have been eliminated. Further, by using the present circle-less breathing circuit 1300, soda lime (or substitutes) are removed from the environmental waste streams, and drive gas (or another form of energy) is not necessarily required, thereby making the use of an oscillating pump for air and an oxygen concentrator unnecessary as less power is required to run the circuit. Since, in the present circuit, the inspired gas is always clean, the circuit is optimal as far as infection control is concerned and is also easier to maintain, resulting in a lower cost of ownership. Further, it has been observed that clinicians are frequently confused regarding the dilution effects of the circle circuit, thereby resorting to inspired gas control (IGC) or expired gas control (EGC) systems. The present circle-less breathing circuit 1300 provides IGC automatically, since there is no dilution effect. In an embodiment, the inspiratory valve feature can be implemented entirely in software and flows much higher than those provided by a traditional mixer can be achieved.

Bypass Oxygen Control and Actuation

As is commonly known in the art, anesthesia systems with electronic mixing control usually also comprise an emergency bypass valve system that enables a user to set a flow of oxygen in the event of a mixer failure. Some prior art anesthesia systems employ dedicated needle valves to provide the bypass functionality, while others use dedicated mechanical-pneumatic switches to turn on a bypass valve or to revert to an electronic mixer control.

In one embodiment, the present specification is directed toward an anesthesia delivery system comprising a dual position knob which, in a first position, corresponds to an active electronic mixing control and, in a second position, corresponds to an active emergency bypass valve. In the second position, the dual position knob "pops out" and simultaneously engages a mechanical needle valve when an emergency bypass valve is activated while the flow from the electronic mixer is discontinued. The dual position knob provides a single point of oxygen adjustment which enables a user to quickly adjust oxygen flow in case of failure of the electronic mixing control of the anesthesia system and, also in cases where the user is unaware of the type of failure occurring in the anesthesia system. Further, by pushing the dual position knob back into the first position, the electronic mixing control of the anesthesia system is re-engaged. The present specification also provides for pre-setting a predetermined amount of oxygen flow from the bypass needle valve when the emergency bypass is activated, causing a known amount of oxygen flow to occur automatically in the event of electronic mixer control failure, without requiring any user interaction.

Figure 14A:
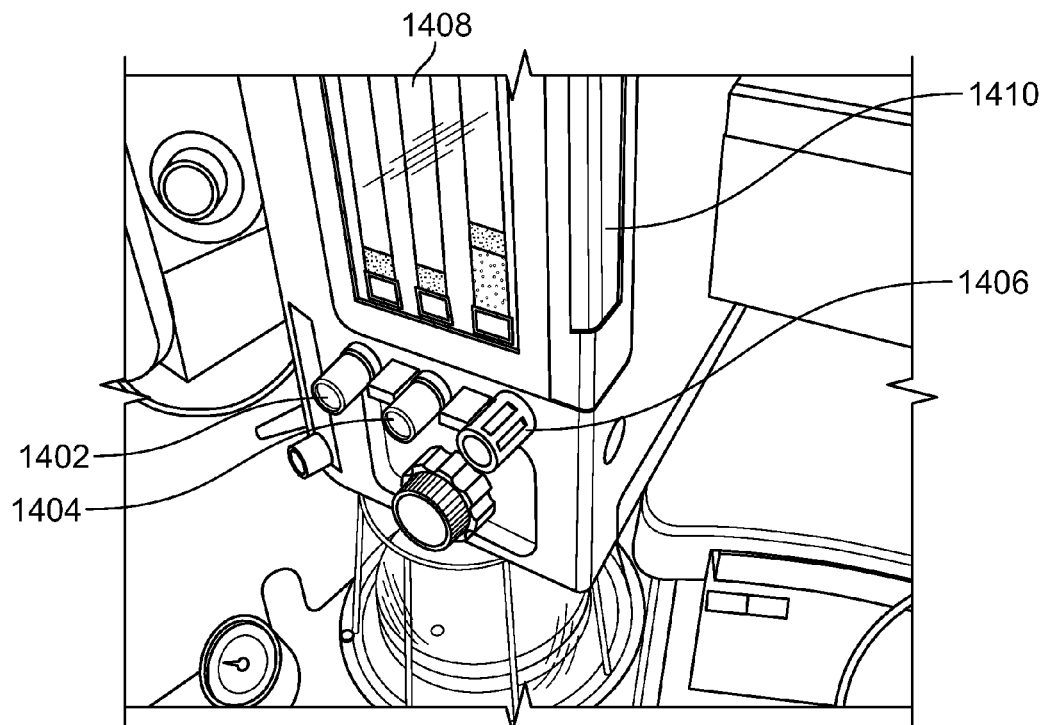
FIG. 14A illustrates a first position of a bypass actuation knob of the anesthesia system in accordance with an embodiment of the present specification.

FIG. 14A illustrates a first position of a bypass actuation knob 1406 of the anesthesia system in accordance with an embodiment of the present specification. The anesthesia system comprises gas control knobs 1402, 1404 and a dual position bypass actuation knob 1406. The knobs 1402, 1404 and 1406 engage with an electronic encoder (not shown in FIG. 14A) and are used to electronically control gas flow rates in the anesthesia system. The flow of gases in the anesthesia system is displayed graphically on an electronic screen 1408 and via a floating ball type flow meter 1410. As illustrated in FIG. 14A, the bypass actuation dual position knob 1406 is in a first position being flush with a side surface of the anesthesia system, indicating that electronic mixing control of the anesthesia system is engaged.

Figure 14B:
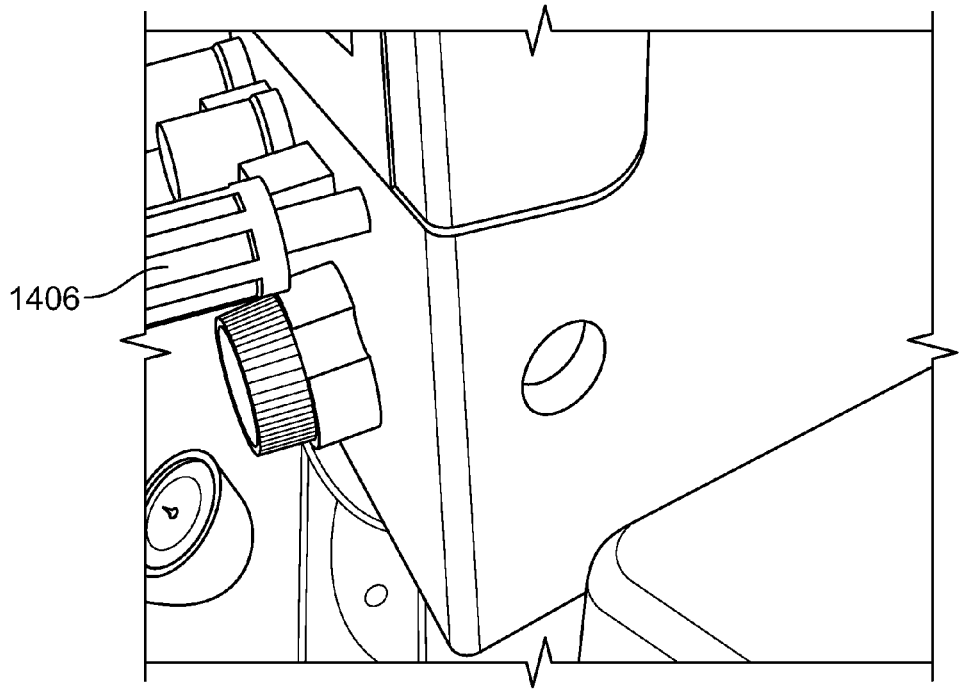
FIG. 14B illustrates a second position of a bypass actuation knob of the anesthesia system, in accordance with an embodiment of the present specification.

FIG. 14B illustrates a second position of a bypass actuation knob 1406 of the anesthesia system, in accordance with an embodiment of the present specification. As illustrated in FIG. 14B, the bypass actuation dual position knob 1406 is in a second "popped out" active position, indicating an activated emergency oxygen bypass function in the anesthesia system. In the active position, the knob 1406 is directly engaged with a needle valve (not shown in FIG. 14B) that controls the flow of oxygen directly, bypassing the electronic mixer control of the anesthesia system.

Figure 14C:
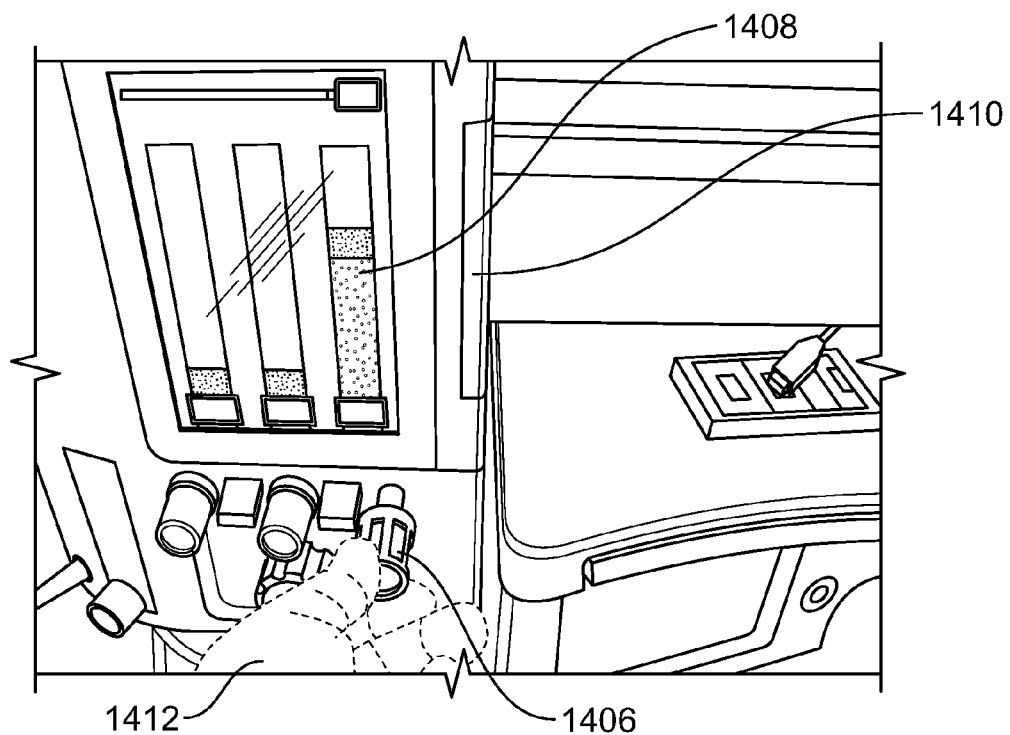
FIG. 14C illustrates a user adjusting a bypass actuation knob of the anesthesia system, in accordance with an embodiment of the present specification.

FIG. 14C illustrates a user adjusting a bypass actuation knob 1406 of the anesthesia system, in accordance with an embodiment of the present specification. As illustrated in FIG. 14C, a user 1412 may adjust the flow of oxygen in the anesthesia system by adjusting the bypass actuation dual position knob 1406 manually based on the oxygen flow being depicted graphically on electronic screen 1408. Hence, the present specification enables a user to adjust the bypass oxygen flow by observing a graphical display 1408 of the flow values. Further, the floating ball type flow meter 1410 also registers all the gas flow being provided to a patient.

Figure 14D:
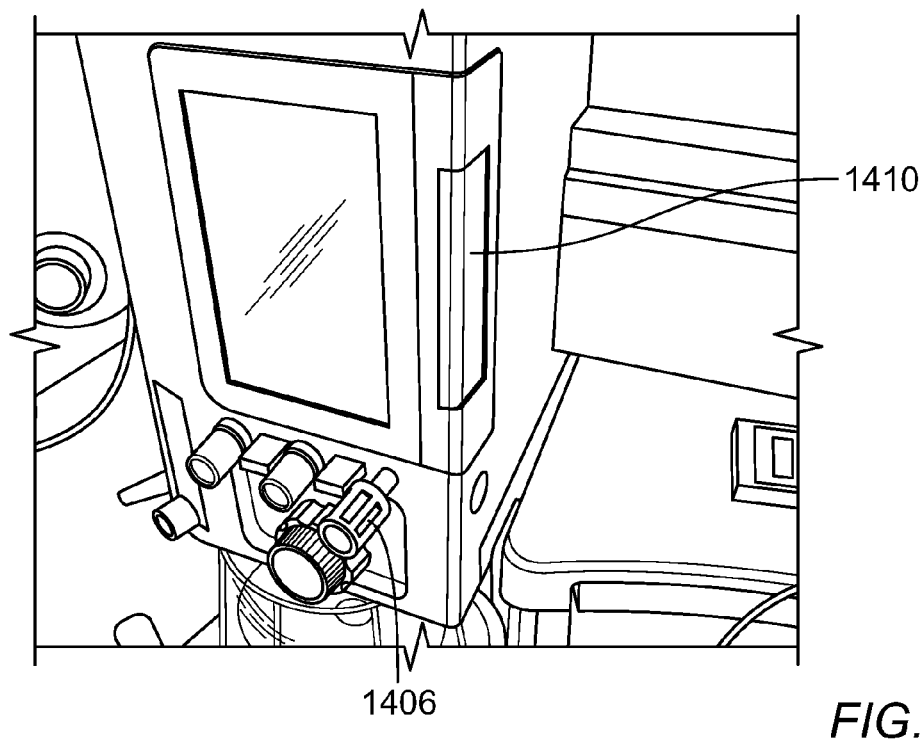
FIG. 14D illustrates an active bypass actuation knob of the anesthesia system when the anesthesia system is in an 'off' state, in accordance with an embodiment of the present specification.

FIG. 14D illustrates an active bypass actuation knob 1406 of the anesthesia system even when the anesthesia system is in an 'off' state, in accordance with an embodiment of the present specification. In an embodiment, even when the anesthesia system's electronics are in a state simulating an electronic failure, the bypass actuation dual position knob 1406 remains in an active state as illustrated in FIG. 14D and causes a continuous flow of oxygen to be delivered to a patient. The flow of oxygen may be manually adjusted in such a situation by observing a representation of the flow values on the floating ball type flow meter 1410.

ACGO Flip-Up Selector

Conventional anesthesia systems are typically equipped with an auxiliary common gas outlet (ACGO) that enables mixed "fresh gas flow" (FGF) to be diverted from a circle system to an external circuit, which is typically of a non-rebreathing type anesthesia system. In prior art anesthesia systems, the ACGO is typically a horizontal 22 mm port that is activated through a mechanical lever or via an electrical control provided on a user interface. Prior art anesthesia systems do not provide a clear indication of an active ACGO, thereby causing confusion regarding whether the ACGO is active or not and in some cases, even causing the ACGO to be activated inadvertently by a user.

In one embodiment, the present specification is directed toward an anesthesia delivery system which provides an ACGO as a 22 mm port such that the port itself may be used for activation. In an embodiment, the ACGO is turned off by rotating the port downwards such that the port rests vertically and the port opening faces the floor and its plane is parallel with the floor. This positioning reduces significantly the chances of the ACGO port being mistakenly treated as a source of fresh gas flow by a user. In this position, the FGF is automatically directed to an internal fresh gas flow port within the system's circle breathing circuit. The AGCO is activated by rotating the port upwards by 90 degrees such that the port rests horizontally and the port opening faces the user and its plane is perpendicular with the floor. This positioning enables attachment of tubes to the port. In an embodiment, the AGCO port is provided as a bi-stable switch that can either be turned upwards or downwards corresponding to an active or inactive state, respectively. The port cannot be set in an intermediate position. Also, in an embodiment, the information projection lighting feature of the present specification is incorporated into the AGCO port which is illuminated with a green pulsing light when the port is up and active.

Figure 15A:
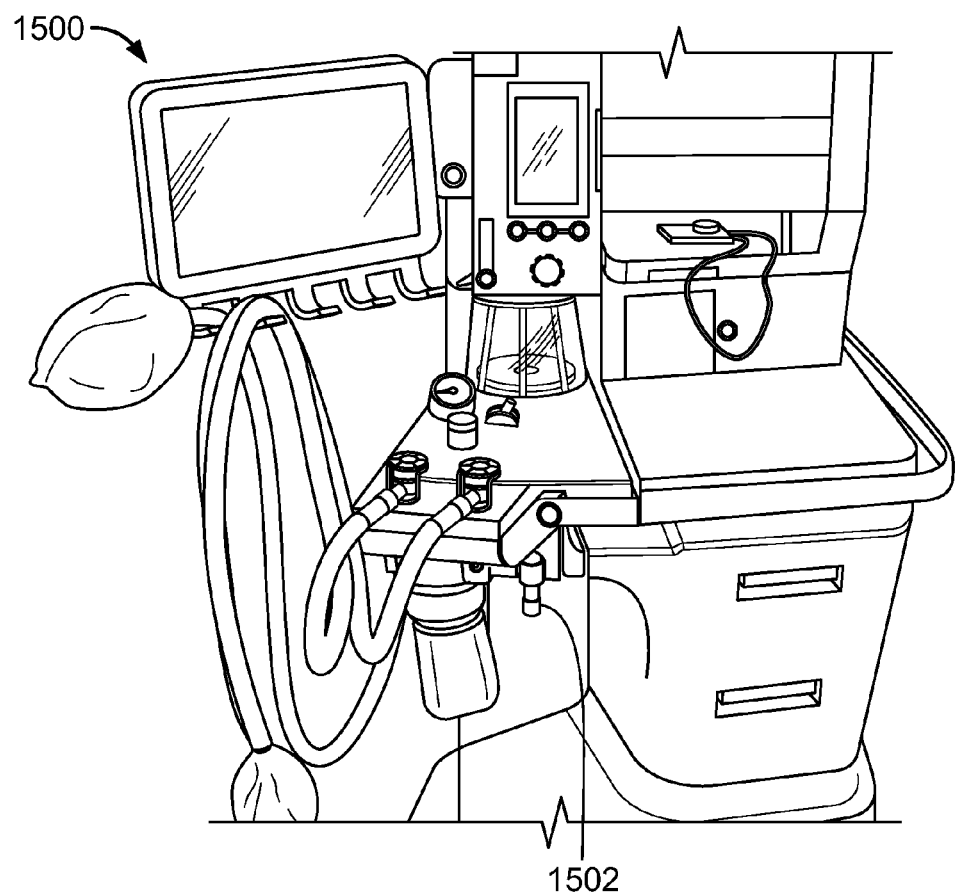
FIG. 15A illustrates an auxiliary common gas outlet (ACGO) port of the anesthesia system, in accordance with an embodiment of the present specification.
Figure 15B:
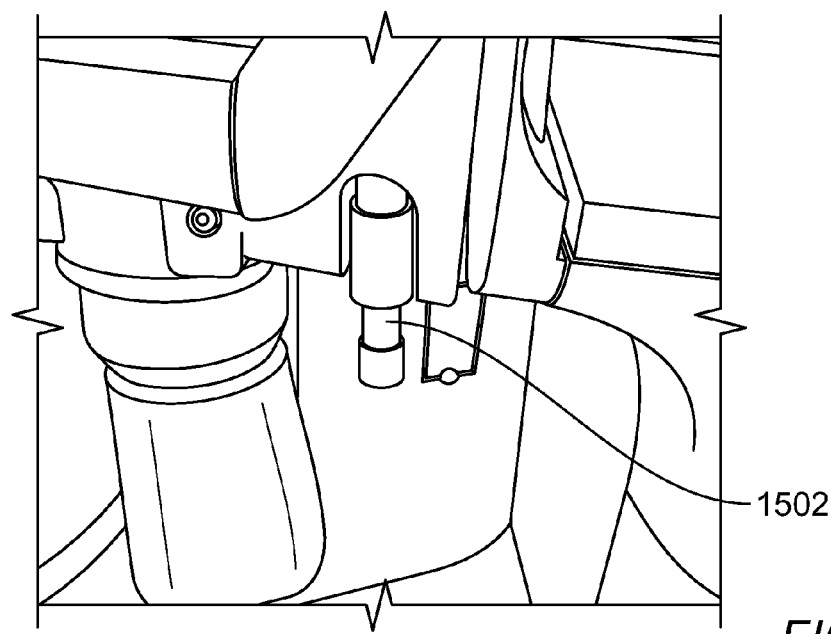
FIG. 15B illustrates an inactive position of the auxiliary common gas outlet (ACGO) port of the anesthesia system, in accordance with an embodiment of the present specification.
Figure 15C:
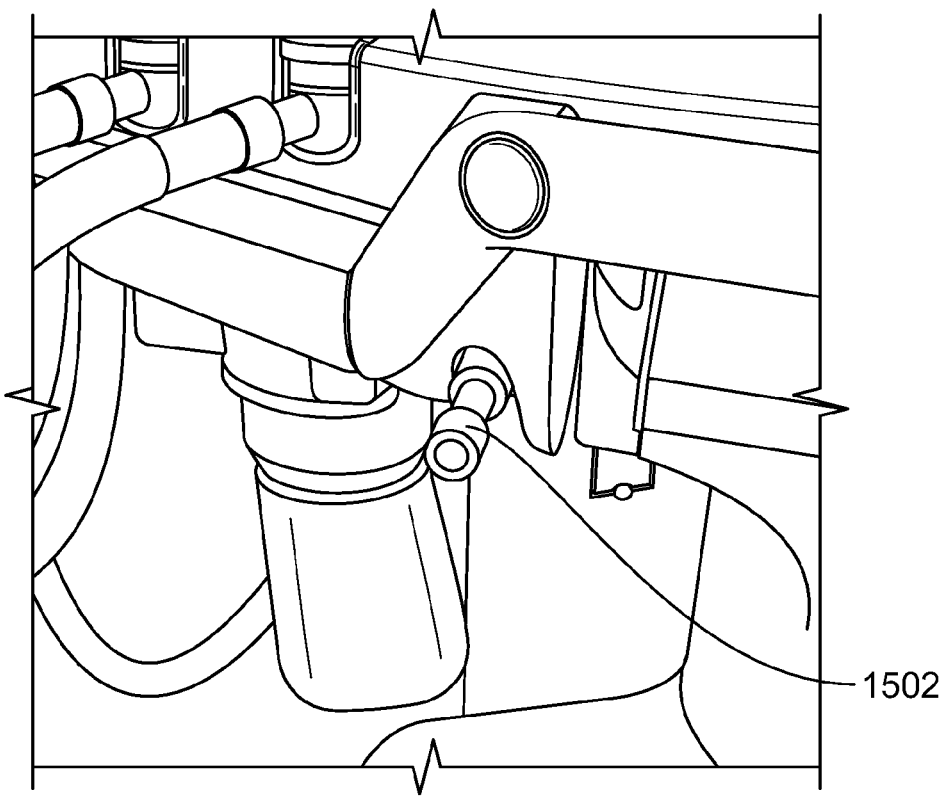
FIG. 15C illustrates an active position of the auxiliary common gas outlet (ACGO) port of the anesthesia system, in accordance with an embodiment of the present specification.

FIG. 15A illustrates an auxiliary common gas outlet (ACGO) port 1502 of the anesthesia system 1500, in accordance with an embodiment of the present specification. FIG. 15B illustrates an inactive position of the auxiliary common gas outlet (ACGO) port 1502 of the anesthesia system 1500, in accordance with an embodiment of the present specification. As illustrated, the AGCO 1502 is in an inactive state as it is turned vertically downwards. FIG. 15C illustrates an active position of the auxiliary common gas outlet (ACGO) port 1502 of the anesthesia system 1500, in accordance with an embodiment of the present specification. As illustrated in FIG. 15C, the AGCO 1502 is in an active state as it is turned upwards in a horizontal position. When the AGCO port 1502 is active, fresh gas, from a gas mixing system of the anesthesia system 1500, flows out from the AGCO port 1502.

Figure 15D:
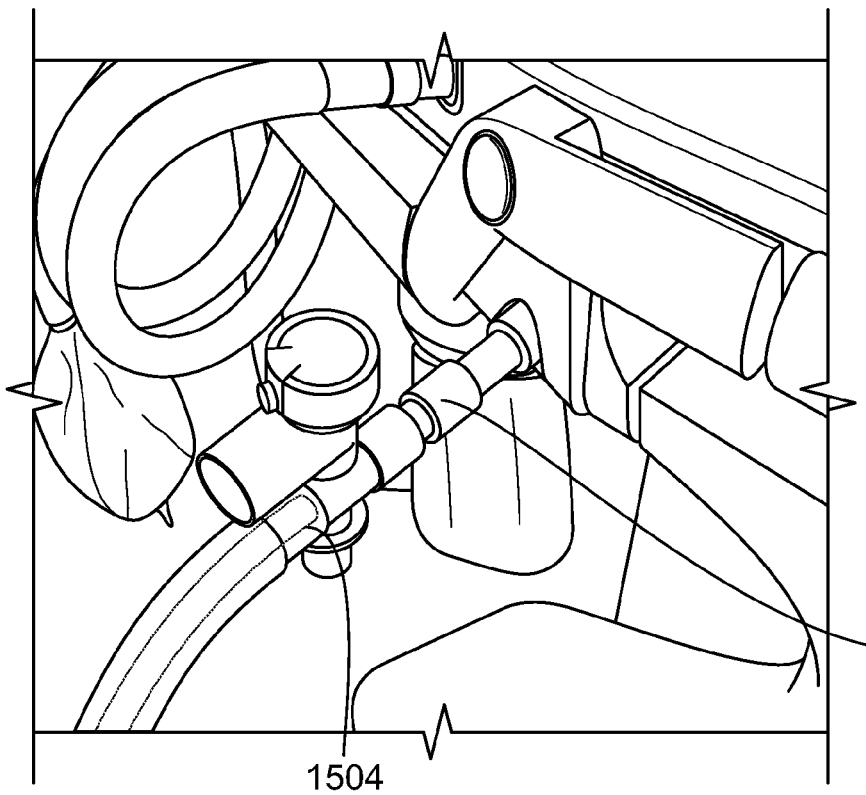
FIG. 15D illustrates an active position of the auxiliary common gas outlet (ACGO) port with a breathing circuit attached, in accordance with an embodiment of the present specification.

FIG. 15D illustrates an active position of the auxiliary common gas outlet (ACGO) port 1502 with a breathing circuit attached, in accordance with an embodiment of the present specification. As illustrated in FIG. 15D, a breathing circuit 1504 may be attached to the AGCO port 1502 when the port 1502 is in an active horizontal position. In an embodiment, the breathing circuit 1504 is used for hand ventilating patients (bag is not shown for clarity) using the fresh gas flow from the ACGO port 1502. In an embodiment, the AGCO port 1502 in its active upwards horizontal position may support a load of a 5 lb breathing circuit.

Electronic Vaporization

Contemporary anesthetic vaporizer systems contain valves and/or wick systems for transitioning liquid anesthetic agent into a gaseous form. Typically, these systems provide an agent concentration level of 0-10% (although sometimes higher for Suprane) of the gas being used as "fresh gas" or "make-up" gas in a circle breathing system. Contemporary devices are rather complex and require precision mechanical components or flow control systems to operate, creating a relatively high cost device. A new type of vaporizer element has been described in U.S. Pat. No. 6,155,255, assigned to Louis Gibeck AB, which utilizes direct liquid injection into a low cost "wick" arrangement.

The present specification provides a method by which vaporizer elements, similar to those described in U.S. Pat. No. 6,155,255, may be integrated into an anesthesia system for practical use as an electronic vaporizer. In an embodiment, a micro piezo pump is used for pumping the liquid to be vaporized. Injection of the liquid is measured in a supply line supplying liquid to the vaporizer and control is accomplished using a feedback loop. Measurement of liquid flow into the evaporator (i.e. wick) and measurement of gas flow either into or out of the evaporator (difference being anesthetic vapor) is used in order to determine concentration of anesthetic agent. This step is performed alternative to or in conjunction with anesthetic agent concentration measurement at the patient site. Further, pulsing (i.e. increasing or decreasing) of liquid flow in conjunction with gas flow changes through the evaporator may be performed. The evaporator is placed in the main flow stream of a circle-less breathing circuit anesthesia system, such as the one described in the preceding section. A control unit controlling the liquid flow into the evaporator is connected to the display of an anesthesia system, integrating the vaporizer subsystem as a component of a broader anesthesia system of the present specification. This allows agent data to be presented with fresh gas flow rates and patient tidal volumes.

In one embodiment, a valve is added to a known electronic vaporizer, similar to the one described in U.S. Pat. No. 6,155,255, and is controlled to provide an immediate gas flow bypass of the evaporator. This is used for an oxygen flush of the system or for immediately turning off the vaporizer. Proportional control of this bypass may also be used to quickly reduce the amount of vapor being added without entirely ceasing the vapor addition, as is the case with a complete bypass. Further, a component of the fresh gas flow (e.g. oxygen) may be selectively passed through the evaporator in order to obtain a consistent uptake of anesthetic agent vapor. In an embodiment, a liquid type agent detection means is added to either a pump connected to an external container of the liquid anesthetic (from which the liquid anesthetic is pumped into the vaporizer) or the container itself for determining the anesthetic type. Further, the container may comprise a plurality of reservoirs, the operation of each being controlled by a pump controller unit, thereby allowing for multiple anesthetic agent types to be present on a single anesthesia machine. The reservoir(s) containing the anesthetic agents may be cooled to maintain anesthetic agents in liquid form for injection by the liquid injection means of a pump connected to the vaporizer. In various embodiments, various protection and elimination of liquid cavitation means are employed. Examples of such means comprise: cooling of one or more pumps to prevent cavitation as the anesthetic liquid is pumped through the system; pressurizing of anesthetic agent reservoirs into a connected pump to prevent cavitation; employing cavitation detection means in the pump or a supply line connecting the reservoirs to the pump; employing specific known design features in the supply line or pump to prevent cavitation; and, adding resistance to the supply line, thereby creating backpressure in order to prevent cavitation.

In one embodiment, the present specification allows for selection of different evaporator sizes based on the amount of fresh gas flow. For example, an anesthesia control means (such as a knob or switch) could select either a high flow or a low flow evaporator depending on the amount of fresh gas flow being used. Also, an on/off valve can be employed in the anesthetic agent supply line as a safety control to immediately stop liquid injection into the evaporator. In an embodiment, a sensor element is positioned at the patient airway for reading the optical absorption of the gas being inspired by the patient at different light wavelengths, and the signals sensed at that point are used for performing either inspired gas control or expired gas control using the vaporizer as a subsystem of an anesthesia machine. Further, in an embodiment, two liquid flow sensors are used in series, one for high flow and one for low flow, to sense the full range of liquid flow rates at sufficient accuracy.

The above examples are merely illustrative of the many applications of the system of the present invention. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

We claim:

1. An anesthesia delivery system, wherein the anesthesia delivery system monitors a plurality of patient parameters, comprising:
   a first section comprising housing for at least one clinical control and at least one patient connection for providing therapy to a patient, wherein said at least one patient connection includes a breathing circuit connection, comprising at least one limb;
   a second section, comprising a base portion for supporting the first section, a planar workspace surface, at least one pneumatic connection and at least one electrical connection, wherein the second section is pneumatically connected to the first section by a suction supply line and at least one anesthesia gas supply line and wherein the first section is movable relative to the second section;
   a self-activating auxiliary common gas outlet (ACGO) port, wherein said self-activating auxiliary common gas outlet (ACGO) port has a first position and a second position, wherein, in said first position, the self-activating auxiliary common gas outlet (ACGO) port is in an inactive state, wherein, in said second position, the self-activating auxiliary common gas outlet (ACGO) port is in an active state, wherein said self-activating auxiliary common gas outlet (ACGO) port is activated by a rotation of said auxiliary common gas outlet (ACGO) port from the first position to the second position, and wherein, in said active state, gas flows out of said self-activating auxiliary common gas outlet (ACGO) port; and
   a display comprising:
      an alarm;
      a first icon, wherein, when activated, said first icon causes the anesthesia delivery system to set a predefined alarm limit for at least one of said plurality of parameters and wherein said alarm is configured to be activated when a value of the at least one of said plurality of parameters is above or below a predefined threshold;
      a second icon, wherein, when activated, said second icon causes the anesthesia delivery system to revert from the predefined alarm limit to an alarm limit existing just before the predefined alarm limit was set for the at least one of said plurality of parameters and wherein said alarm is configured to be activated when a value of the at least one of said plurality of parameters is above or below a second threshold, said second threshold being different than the predefined threshold;
      a graphical user interface in data communication with said anesthesia delivery system; and
      a lighting strip provided on said graphical user interface and configured to communicate to a user when the alarm is active and a priority level of said alarm, further wherein a location and color of said lighting strip is indicative of said priority level of said alarm.

2. The anesthesia delivery system of claim 1, further comprising an emergency bypass valve system which enables a user to set a flow of oxygen in case of a mixer failure, wherein said emergency bypass valve system comprises a dual position knob, which, in a first position, corresponds to an active electronic mixing control and, in a second position, corresponds to an active emergency bypass valve, further wherein a pre-determined amount of oxygen flow is provided when said dual position knob is moved into said second position.

3. The anesthesia delivery system of claim 1, wherein said self-activating auxiliary common gas outlet (ACGO) port measures in a range of 17 to 27 mm in external diameter.

4. The anesthesia delivery system of claim 1, wherein said self-activating auxiliary common gas outlet (ACGO) port measures in a range of 10 to 20 mm in internal diameter.

5. The anesthesia delivery system of claim 1, wherein said self-activating auxiliary common gas outlet (AGCO) port is illuminated when said auxiliary common gas outlet (ACGO) port is in said second position.

6. An anesthesia delivery system, wherein the anesthesia delivery system monitors a plurality of patient parameters, comprising:
   a first section comprising a housing for at least one patient connection, wherein said at least one patient connection includes a breathing circuit connection, comprising at least one limb;
   a second section, comprising a planar workspace surface, at least one pneumatic connection and at least one electrical connection, wherein the second section is pneumatically connected to the first section by a suction supply line and at least one anesthesia gas supply line;
   a self-activating auxiliary common gas outlet (ACGO) port, wherein said self-activating auxiliary common gas outlet (ACGO) port has a first position and a second position, wherein, in said first position, the self-activating auxiliary common gas outlet (ACGO) port is in an inactive state, wherein, in said second position, the self-activating auxiliary common gas outlet (ACGO) port is in an active state, wherein said self-activating auxiliary common gas outlet (ACGO) port is activated by a rotation of said auxiliary common gas outlet (ACGO) port from the first position to the second position, and wherein, in said active state, gas flows out of said self-activating auxiliary common gas outlet (ACGO) port; and a display comprising:

an alarm;

a first icon, wherein, when activated, said first icon causes the anesthesia delivery system to set a predefined alarm limit for at least one of said plurality of parameters and wherein the alarm is configured to be activated when a value of the at least one of said plurality of parameters is above or below a predefined threshold; and a second icon, wherein, when activated, said second icon causes the anesthesia delivery system to revert from the predefined alarm limit to an alarm limit existing just before the predefined alarm was set for the at least one of said plurality of parameters and wherein the alarm is configured to be activated when a value of the at least one of said plurality of parameters is above or below a second threshold, said second threshold being different than the predefined threshold.

* * * * *